(12) United States Patent
Barbour et al.

(10) Patent No.: US 10,105,090 B2
(45) Date of Patent: Oct. 23, 2018

(54) METHOD FOR REPRESENTATIONS OF NETWORK-DEPENDENT FEATURES OF THE HEMOGLOBIN SIGNAL IN LIVING TISSUES FOR DETECTION OF BREAST CANCER AND OTHER APPLICATIONS

(71) Applicants: Photon Migration Technologies Corp., Glen Head, NY (US); SLB Innovations Group, LLC, Glen Head, NY (US)

(72) Inventors: Randall L. Barbour, Glen Head, NY (US); Harry L. Graber, New York, NY (US); San-Lian S. Barbour, Glen Head, NY (US)

(73) Assignees: Photon Migration Technologies Corp., Glen Head, NY (US); SLB Innovations Group, LLC, Glen Head, NY (US)

( * ) Notice: Subject to any disclaimer, the term of this patent is extended or adjusted under 35 U.S.C. 154(b) by 0 days.

(21) Appl. No.: 15/783,723

(22) Filed: Oct. 13, 2017

(65) Prior Publication Data

US 2018/0110458 A1    Apr. 26, 2018

Related U.S. Application Data

(60) Provisional application No. 62/407,883, filed on Oct. 13, 2016.

(51) Int. Cl.
*A61B 5/00* (2006.01)
*A61B 5/145* (2006.01)
*A61B 5/1455* (2006.01)

(52) U.S. Cl.
CPC ........ *A61B 5/4312* (2013.01); *A61B 5/14546* (2013.01); *A61B 5/14552* (2013.01);
(Continued)

(58) Field of Classification Search
CPC ... A61B 5/0205; A61B 5/0059; A61B 5/0073; A61B 5/1455; A61B 5/14551;
(Continued)

(56) References Cited

U.S. PATENT DOCUMENTS 6,516,209 B2 *  2/2003  Cheng ................ A61B 5/14551
                                                      600/323
6,937,884 B1 *  8/2005  Barbour ............. G01N 21/4795
                                                      600/323

(Continued)

OTHER PUBLICATIONS

Sheppard, Analysis of a Single Time Series, Enders (2004), Hamilton (1994).

(Continued)

*Primary Examiner* — Eric Winakur
*Assistant Examiner* — Chu Chuan (J J) Liu
(74) *Attorney, Agent, or Firm* — Kane Kessler, P.C.; Barry E. Negrin

(57) ABSTRACT

A non-invasive method of detecting anomalous tissue, such as cancerous or injured tissue, in a patient. At least two hemoglobin signal components of hemoglobin levels in at least one segment of tissue of the patient are non-invasively measured over time. Time varying changes of at least a first of the hemoglobin signal components are measured with respect to at least time varying changes of a second of the hemoglobin signal components. A co-varying coordinate system of the time varying changes is generated. Any anomalous tissue in the measured segment of tissue is detected from a signature of the measured segment of tissue in the co-varying coordinate system which differs from a signature of non-anomalous tissue in the co-varying coordinate system. Preferably, five hemoglobin signal components are measured: oxyHb, deoxyHb, total Hb (totalHb=oxyHb+deoxy Hb), Hb oxygen saturation
(Continued)

($HbO_2Sat=(oxyHb/totalHb)*100$), and tissue-hemoglobin oxygen exchange $HbO_2Exc$ (deoxyHb−oxyHb).

16 Claims, 16 Drawing Sheets
(9 of 16 Drawing Sheet(s) Filed in Color)

(52) U.S. Cl.
CPC .......... *A61B 5/7225* (2013.01); *A61B 5/7282* (2013.01); *A61B 2562/0233* (2013.01); *A61B 2576/02* (2013.01)

(58) Field of Classification Search
CPC ............ A61B 5/14552; A61B 5/14553; A61B 5/4312; A61B 5/14546
See application file for complete search history.

(56) References Cited

U.S. PATENT DOCUMENTS

| | | | |
|---|---|---|---|
| 8,406,838 B2 | 3/2013 | Kato | |
| 9,700,248 B2* | 7/2017 | Ozaki | A61B 5/1455 |
| 2005/0080323 A1* | 4/2005 | Kato | A61B 5/14553 600/323 |
| 2013/0109950 A1 | 5/2013 | Herzog et al. | |
| 2013/0144140 A1 | 6/2013 | Frederick et al. | |
| 2015/0119665 A1 | 4/2015 | Barbour et al. | |

OTHER PUBLICATIONS

Charles E. Metz, Basic Principles of ROC Analysis, Seminars in Nuclear Medicine, vol. VIII, No. 4 Oct. 1978.
Shinji Umeyama, An Eigendecomposition Approach to Weighted Graph Matching Problems, IEEE Transactions on Pattern Analysis and Machine Intelligence, vol. 10, No. 5, Sep. 1988.
David Weininger, SMILES, a Chemical Language and Information System, J. Chemical Information and Computer Sciences 28, 31-36 (1988).
Lawrence R. Rabiner, A Tutorial on Hidden Markov Models and Selected Applications in Speech Recognition, Proceedings of the IEEE, vol. 77, No. 2, Feb. 1989.
Jain et al., Artificial Neural Networks: A Tutorial, IEEE Computer, Mar. 1996.
Schilling et al., The underlying pathway structure of biochemical reaction networks, Proc. Natl. Acad. Sci. USA, vol. 95, pp. 4193-4198, Apr. 1998, Biochemistry, Engineering.
Barabási et al., Emergence of Scaling in Random Networks, www.sciencemag.org; Science, vol. 286, Oct. 15, 1999.
Schuster et al., Detection of elementary flux modes in biochemical networks: a promising tool for pathway analysis and metabolic engineering, TIBTECH, Feb. 1999 (vol. 17).
Albert et al., Error and attack tolerance of complex networks, Nature, vol. 406, Jul. 27, 2000, www.nature.com.
Schilling et al., Theory for the Systemic Definition of Metabolic Pathways and their use in Interpreting Metabolic Function from a Pathway-Oriented Perspective, J. theor. Biol. (2000) 203, 229-248, doi: 10.1006/jtbi.2000.1073.
Vaupel et al., "Oxygenation of Human Tumors," in Blood Perfusion and Microenvironment of Human Tumors: Implications for Clinical Radiooncology, edited by M. Molls and P. Vaupel (Springer, Berlin, 2000), pp. 63-72.
P. Vaupel, "Tumor blood flow," in Blood Perfusion and Microenvironment of Human Tumors: Implications for Clinical Radiooncology, edited by M. Molls and P. Vaupel (Springer, Berlin, 2000), pp. 41-45.
Wang et al., "Photoacoustic Tomography," Chapter 12 in L.-V. Wang and H. Wu, Biomedical Optics: Principles and Imaging (Wiley-Interscience, 2007), pp. 283-317).
PCT Application No. PCT/US2017/056643—International Search Report and Written Opinion dated Dec. 14, 2017.
Pei et al., Influence of systematic errors in reference states on image quality and on stability of derived information for dc optical imaging, vol. 40, No. 31, Applied Optics, Nov. 1, 2001.
Graber et al., Imaging of Spatiotemporal Coincident States by DC Optical Tomography, IEEE Transactions on Medical Imaging, vol. 21, No. 8, Aug. 2002.
Gheorghe et al., A formal language-based approach on biology, Comparative and Functional Genomics, Comp Funct Genom 2004; 5: 91-94. Published online in Wiley InterScience (www.interscience.wiley.com). DOI: 10.1002/cfg.364.
Schmitz et al., Design and implementation of dynamic near-infrared optical tomographic imaging instrumentation for simultaneous dual-breast measurements, Applied Optics, vol. 44, No. 11, Apr. 10, 2005.
Tony R. Kuphaldt, Lessons in Electric Circuits, vol. I-DC, Fifth Edition, last update Oct. 18, 2006.
Barbour et al., Functional Imaging of Autoregulation (no date).
Wang et al., Electochemical Sensors for Clinic Analysis, State Key Laboratory of Industrial Control Technology, Institute of Advanced Process Control, Zheijiang University, Hangzhou 310027, P.R. China, Sensors 2008, 8, 2043-2081, ISSN 1424-8220, © 2008 by MDPI, www.mdpi.org/sensors.
Lancashire et al., An introduction to artificial neural networks in bioformatics—application to complex microarray and mass spectometry datasets in cancer studies, Briefings in Bioformatics, vol. 10 No. 3. 315-329, Advance Access publication Mar. 23, 2009.
Moulakakis et al., Hyperperfusion syndrome after carotid revascularization, Journal of Vascular Surgery, Apr. 2009.
Stephan et al., Bayesian model selection for group studies, Elsevier, Neuroimage, journal homepage:www.elsevier.com/locate/ynimg, Neuroimage 46 (2009) 1004-1017.
Wylie et al., Using co-variations in the Hb signal to detect visual activation: A near infrared spectroscopic imaging study, Elsevier, Neuroimage, journal homepage:www.elsevier.com/locate/ynimg, Neuroimage 47 (2009) 473-481.
Ahmad et al., Theory, Instrumentation, and Applications of EPR Oximetry, NIH Public Access Author Manuscript, Chem. Rev. May 12, 2010; 110(5): 3212-3236. doi:10.1021/cr900396q.
Arlot et al., A survey of cross-validation procedures for model selection, Statistics Surveys, vol. 4 (2010) 40-79, ISSN: 1935-7516, DOI: 10.1214/09-SS054.
Bélanger et al., Real-time diffuse optical tomography based on structured illumination, Journal of Biomedical Optics 15(1), 016006 (Jan./Feb. 2010).
Mazhar et al., Structured Illumination enhances resolution and contrast in thick tissue fluorescence imaging, Journal of Biomedical Optics, 010506-1, Jan./Feb. 2010, Vo. 15(1).
Al Abdi et al., Optomechanical imaging system for breast cancer detection, Optical Society of America, vol. 28, No. 12, Dec. 2011, J. Opt. Soc. Am. A.
Pavlopoulos et al., Using graph theory to analyze biological networks, BioData Mining 2011, 4:10, http://biodatamining.org/content/4/1/10.
Fitch et al., Artificial grammar learning meets formal language theory: an overview, Phil. Trans. R. Soc. B (2012) 367, 1933-1955 doi:10.1098/rstb.2012-0103.
Jäger et al., Formal language theory: refining the Chomsky hierarchy, Phil. Trans. R. Soc. B. (2012) 367, 1956-1970 doi:10.1098/rstb.2012.0077.
Komjáthy et al., Lecture Notes for Markov Chains: Mixing Times, Hitting Times, and Cover Times, in Saint Petersburg Summer School, 2012.
Sarti et al., Cytochrome c oxidase and nitric oxide in action: Molecular mechanisms and pathophysiological implications, Elsevier, Biochimica et Biophysica Acta, journal homepage: www.elsevier.com/locate/bbabio, Biochimica et Biophysica Acta 1817 (2012) 610-619.
Wang et al., Photoacoustic Tomography: In Vivo Imaging from Organelles to Organs, Mar. 23, 2012, vol. 335, Science, www.sciencemag.org.
Yoshino et al., Vector-based phase classification of initial dips during word listening using near-infrared spectroscopy, NeuroReport 2012, 23:947-951, vol. 23, No. 16.

(56) References Cited

OTHER PUBLICATIONS

Busch et al., Toward Noninvasive Characterization of Breast Cancer and Cancer Metabolism with Diffuse Optics, pet.theclinics.com, PET Clin 8 (2013) 345-365, http://dx.doi.org/10.1016/j.cpet.2013.04.004.

Pereda et al., Gap junction-mediated electrical transmission: Regulatory mechanisms and plasticity, Elsevier, Biochimica et Biophysica Acta, journal homepage: www.elsevier.com/locate/bbamem, Biochimica et Biophysica Acta 1828 (2013) 134-146.

Barquero et al. (2014) Neuroimaging of Reading Intervention: A Systematic Review and Activation Likelihood Estimate Meta-Analysis. PLoS ONE 9(1):e83668. doi:10.1371/journal.pone.0083668.

Mario Beuregard, PhD., Functional neuroimaging studies of the effects of psychotherapy, www.dialogues-cns.org, Dialogues in Clinical Neuroscience—vol. 16, No. 1, 2014.

Sergio Fantini, Dynamic model for the tissue concentration and oxygen saturation of hemoglobin in relation to blood volume, flow velocity, and oxygen consumption: Implications for functional neuroimaging and coherent hemodynamics spectroscopy (CHS), Elsevier, NeuroImage, journal homepage: www.elsevier.com/locate/ynimg, NeuroImage 85 (2014) 202-221.

Piper et al., A wearable multi-channel fNIRS system for brain imaging in freely moving subjects, Elsevier, Neuroimage, journal homepage: www.elsevier.com/locate/ynimg, Neuroimage 85 (2014) 64-71.

Somvanshi et al., A conceptual review on systems biology in health and diseases: from biological networks to modern therapeutics, Syst Synth Biol (2014) 8:99-116, DOI 10.1007/s11693-013-9125-3.

Graber et al., Enhanced resting-state dynamics of the hemoglobin signal as a novel biomarker for detection of breast cancer, Medical Physics, 42, 6406 (2015); doi: 101118/1.4932220.

Taroni et al., (2015) Breast Tissue Composition and its Dependence on Demographic Risk Factors for Breast Cancer: Non-Invasive Assessment by Time Domain Diffuse Optical Spectroscopy. PLoS ONE 10(6):e0128941. doi: 10.1371/journal.pone.0128941.

Vaquero et al., Positron Emission Tomography: Current Challenges and Opportunities for Technological Advances in Clinical and Preclinical Imaging Systems, Annu. Rev. Biomed. Eng. 2015.17:385-414.

Zhan et al., A Window into the Brain: Advances in Psychiatric fMRI, Hindawi Publishing Corporation, BioMed Research International, vol. 2015, Article ID 542467, 12 pages, http://dx.doi.org/10.1155/2015/542467.

Barbour et al., Charaterization of Hemoglobin Dynamics as a Co-varying System in the Resting State: Evidence of Functional Bias of Preferred States and Sensitivity to Disease.

Calderoni et al., (2016) Rehabilitative Interventions and Brain Plasticity in Autism Spectrum Disorders: Focus on MRI-Based Studies. Front. Neurosci. 10:139. doi: 10.3389/fnins.2016.00139.

Hengen et al., Neuronal Firing Rate Homeostasis is Inhibited by Sleep and Promoted by Wake, 2016, Cell 165, 180-191, Mar. 24, 2016 © 2016 Elsevier Inc., http://dx.doi.org/10.1016/j.cell.2016.01.046.

Hong et al, Reduction of Delay in Detecting Initial Dips from Functional Near-Infrared Spectroscopy Signals Using Vector-Based Phase Analysis, International Journal of Neural Systems, vol. 26, No. 3 (2016) 1650012 (16 pages), © World Scientific Publishing Company, DOI: 10.1142/S012906571650012X.

Jayachandran et al., Critical Review of Noninvasive Optical Technologies for Wound Imaging, Advances in Hound Care, vol. 5, No. 8, DOI: 10.1089/wound.2015.0678.

Saliba et al., Functional near-infrared spectroscopy for neuroimaging in cochlear implant recipients, Elsevier, Hearing Research, journal homepage: www.elsevier.com/locate/heares, Hearing Research 338(2016) 64-75.

Tromberg et al., Predicting Responses to Neoadjuvant Chemotherapy in Breast Cancer: ACRIN 6691 Trial of Diffuse Optical Spectroscopic Imaging, downloaded from cancerrres.aacrjournals.org on May 12, 2017. Published OnlineFirst Aug. 15, 2016; DOI: 10.1158/0008-5472.CAN-16/0346.

Balardin et al., (2017) Imaging Brain Function with Functional Near-Infrared Spectroscopy in Unconstrained Environments, Front. Hum. Neurosci. 11:258. doi: 10.3389/fnhum.2017.00258.

Curtin et al., Evaluation of evoked responses to pulse-matched high frequency and intermittent theta burst transcranial magnetic stimulation using simultaneous functional near-infrared spectroscopy, Neurophoton. 4(4), 041405 (2017), doi: 10.1117/1.NPh.4.4.041405.

Ikebata et al., Bayesian molecular design with a chemical language model, J Comput Aided Mol Des (2017) 31:379-391, DOI 10.1007/s10822-016-008-z.

Schuh et al., Imaging Blood Vessel Morphology in Skin: Dynamic Optical Coherence Tomography as a Novel Potential Diagnostic Tool in Dermatology, Dermatol Ther (Heidelb) (2017) 7:187-202, DOI 10.1007/s13555-017-0175-4.

Sitaram et al., Closed-loop brain training: the science of neurofeedback, Nature Reviews, Neuroscience, Feb. 2017, vol. 18.

Eliza Strickland, Why Mary Lou Jepsen Left Facebook: To Transform Health Care and Invent Consumer Telepathy—IEEE Spectrum, https://spectrum.ieee.org/the-human-os/biomedical/imaging/why-mary-lou-jepsen-left-facebook-to-transform-heath-care-and-invent-consumer-telepathy.

Taroni et al., Non-invasive optical estimate of tissue composition to differentiate malignant from benign breast lesions: A pilot study, www.nature.com/scientificreports, 7:40683, DOI: 10.1038/srep40683.

Yoshihara et al., Oxygen imaging of living cells and tissues using luminescent molecular probes, Elsevier, Journal of Biochemistry and Photobiology C: Photochemistry Reviews 30 (2017) 71-95, journal homepage: www.elsevier.com/locate/jphotochemrev.

* cited by examiner

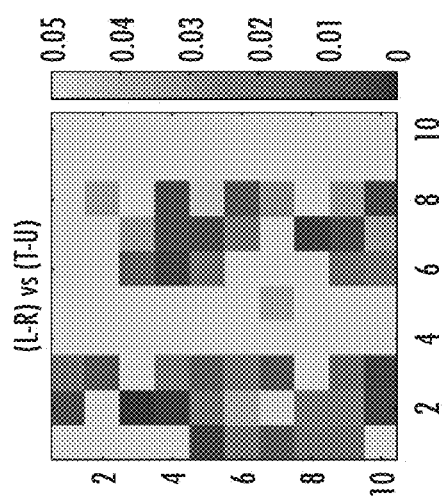
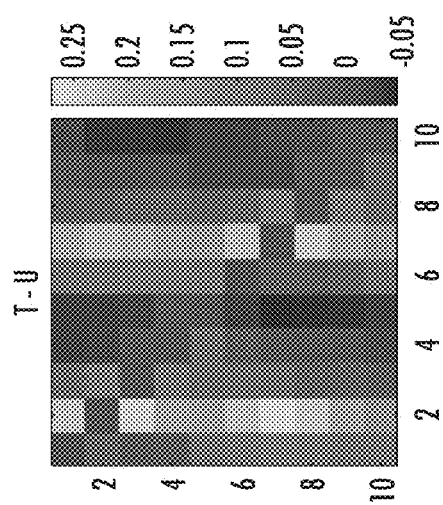
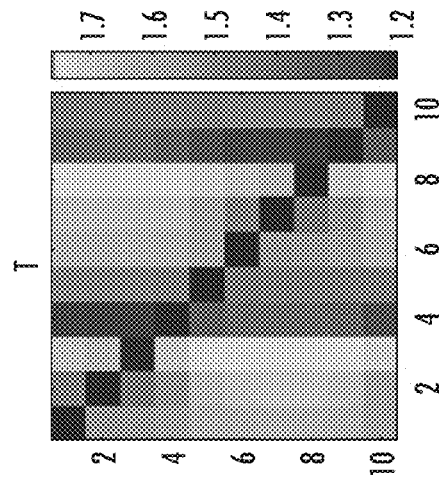
FIG. 5C
FIG. 5B
FIG. 5A

METHOD FOR REPRESENTATIONS OF NETWORK-DEPENDENT FEATURES OF THE HEMOGLOBIN SIGNAL IN LIVING TISSUES FOR DETECTION OF BREAST CANCER AND OTHER APPLICATIONS

RELATED APPLICATIONS

Priority is claimed from US Provisional Patent Application No. 62/407,883, filed Oct. 13, 2016, and entitled "Systems and Methods for Improved Examination of the Information Content of Hb Signal Dynamics by Moment Analysis of Co-varying Components", the entirety of which is incorporated by reference herein.

BACKGROUND OF THE INVENTION

Technical Field

The present invention employs near infrared optical sensing methods applied to living tissue for the purpose of measuring the time-varying features of the hemoglobin signal acquired from reemitted light that has been diffusely transmitted or back-reflected and has been evaluated by a finite-state representation of co-varying signals comprising oxyhemoglobin, deoxyhemoglobin, total hemoglobin, hemoglobin oxygen saturation and tissue-hemoglobin oxygen exchange from measures acquired substantially under the resting state, as a basis for disease detection and in support of other applications.

Description of Related Art

1. Background: Molecular oxygen serves as the end-terminal electron acceptor in the mitochondrial cytochrome chain. This process, which drives ATP formation with the reduction of oxygen to form water, is the principal mechanism responsible for cellular energy production in aerobic organisms. Being highly reactive, oxygen, unlike other essential nutrients, is not stored in the body in any appreciable quantity. Instead, it is made continuously available to body tissues through a tightly regulated process that involves its uptake and binding to hemoglobin (Hb) in the lungs and its delivery to tissue via the circulatory system. Delivery of oxygen to cells is accomplished by diffusion from the vascular space at the level of the microvascular bed. The metabolic needs of tissue vary and can change suddenly (e.g., in response to exercise), and in order to maintain homeostasis it is essential that oxygen availability be responsive to these varying demands. This need is met by local and central feedback mechanisms that can adjust blood flow at the level of the microvascular bed and hence oxygen availability. Accompanying these changes are variations to blood volume that includes the infusion of arterialized blood causing a relative hyperemia (e.g., neurovascular coupling), and hence changes in blood oxygenation.

These adjustments have the effect of producing changes in the levels of the two principal forms of Hb, oxyhemoglobin (oxyHb) and deoxyhemoglobin (deoxyHb). Available from measures of these quantities are three other computed quantities, namely total Hb, (totalHb=oxyHb+deoxy Hb), Hb oxygen saturation (HbO$_2$Sat=(oxyHb/totalHb)*100), and a related quantity referred to as tissue-hemoglobin oxygen exchange (HbO$_2$Exc=deoxyHb−oxyHb), which reflects the fact that separate from temporal variations in oxygen delivery, the rate of oxygen utilization by tissue can also vary due to modulatory influences of feedback mechanisms on the vascular bed.

Factors Affecting Oxygen Delivery to Tissue:

Disruption of oxygen homeostasis can lead to serious and life-threatening conditions, such as occurs during a heart attack or stroke. Similarly, acute trauma, causing either blood loss or crushing injury, can produce severe disruptions in oxygen availability that can also be life threatening. These understandings also extend to a host of disease states and other manipulations in response to specific maneuvers or actions of drugs that may adversely affect oxygen delivery to tissue.

For instance, in many forms of cancer, commonly seen is the phenotype of enhanced angiogenesis. However, the vessels that are formed do not have a normal architecture. Instead they are often distended, tortuous and are leaky, leading to increased interstitial pressures. The combined effect is that, despite the presence of abnormally high vascular densities, oxygen availability is often insufficient, leading to hypoxia. Also commonly seen in cancer is a sustained inflammatory response. A recent report by Graber et al. [H. L. Graber, R. M. Al abdi, Y. Xu, A. P. Asarian, P. J. Pappas, L. Dresner, N. Patel, K. Jagarlamudi, W. B. Solomon, and R. L. Barbour, "Enhanced resting-state dynamics of the hemoglobin signal as a novel biomarker for detection of breast cancer," *Medical Physics* 42, 6406 (2015)] has shown evidence that this feature can be detected using near infrared spectroscopy (NIRS), that it can serve as a biomarker for the presence of cancer, and that it can be identified under resting-state conditions, with good diagnostic performance.

Similar outcomes are also seen in other forms of chronic disease, although for different reasons. For instance, vasculo-occlusive disease, such as occurs in late-stage diabetes, reduces oxygen availability as a consequence of occlusion of small vessels, and also impedes vascular endothelia cell function, thereby reducing the effectiveness of the feedback mechanisms. The net effect is a generalized state of hypoxia in affected tissues, with reduced organ function.

Acting as a stressor, the state of hypoxia can trigger compensatory mechanisms that themselves can lead to added morbidity. Commonly seen is an inflammatory response. While acute inflammatory responses, for example to fight off a local infection, are normal and resolve without lasting effects, chronic inflammation can trigger other disorders. Among these are the secondary influences associated with autoimmune diseases, such as occurs in multiple sclerosis. Sustained inflammation can also adversely affect the delivery of pharmaceutical agents to tissue, making them less effective due to increased diffusion lengths. It also can lead to conditions of hypoxia as a consequence of increased interstitial pressures. This has important implications for the effectiveness of radiotherapy treatments.

Beyond concerns arising from disease that can affect oxygen delivery to tissue, a variety of clinical interventions can affect this process in ways that lead to added morbidity, or that serves as evidence that the applied intervention is not having the intended effect. For instance, a rare but serious complication of carotid revascularization following carotid endarterectomy or carotid stent placement is hyperperfusion syndrome. Believed to result from either baroreceptor reflex failure or impairment to microvascular autoregulation, excessive reperfusion leads to severe headache, seizures, and in some cases intracranial hemorrhage [K. G. Moulakakis et al., "Hyperperfusion syndrome after carotid revascularization," *J. Vascular Surg.* 49, 1060-1068 (2009)]. Also of general concern are the initial occult effects that can lead to compartment syndrome following injury to soft tissues. When present and untreated, the ensuing tissue ischemia caused by excessive interstitial pressures can rapidly lead to non-viability of a limb requiring amputation and, in some instances, renal failure and death.

Yet another commonly encountered concern is the unintended side effects of drugs. Depending on the drug, the concern presented can be excessive toxicity (e.g., chemotherapy treatments) resulting from induced metabolic imbalances that affect liver, renal or lung function, unexpected changes in blood pressure, or psychiatric effects, among others. In many such instances, a secondary consequence of these influences is disturbances in oxygen delivery or its utilization in key organs. In other instances, the aim of the drug can be to modify oxygen utilization, such as occurs with Meldomium, a banned drug used to enhance athletic performance, whose action is thought to favor carbohydrate metabolism over the more oxygen-consuming effects of fat metabolism.

Understandings gained from appreciation of the importance that changes in oxygen delivery have on tissue function have also played a key role in optimizing the performance of neural implants and guiding diagnosis of various neuropsychiatric disorders. A common strategy to guide such efforts is measures of the hemodynamic response that accompanies neuroactivation. Being strongly coupled through the action of astrocytes, activation of neurons in response to, for example, sensory inputs, motor activation or cognition, leads to release of vasodilatory agents that triggers a local and transient hyperemia. When measured using magnetic resonance techniques (fMRI), this signal, known as the Blood Oxygen Level Dependent (BOLD) response, has been used to characterize the spatiotemporal behavior of the brain to a wide range of stimuli. While such measures have been applied to appreciate responses linked to psychiatric disorders [X. Zhan and R. Yu, "A window into the brain: Advances in psychiatric fMRI," *BioMed Research International* 2015, Article 542567 (2015)] and to various treatment interventions [M. Beauregard, "Functional neuroimaging studies of the effects of psychotherapy," *Dialogues in Clinical Neuroscience* 16, 75-81 (2014); L. A. Barquero, N. Davis, and L. E. Cutting, "Neuroimaging of reading intervention: A systematic review and activation likelihood estimate meta-analysis," *PLoS ONE* 9, Article e83668 (2014); S. Calderoni, L. Billeci, A. Narzisi, P. Brambilla, A. Retico, and F. Muratori, "Rehabilitative Interventions and brain plasticity in autism spectrum disorders: Focus on MRI-based studies," *Frontiers in Neuroscience* 10, Article 139 (2016)] this method is generally considered unsuitable for evaluation of neural implants. Instead, expected event-related changes in oxygen utilization following, for example, cochlear implantation can be assessed by noninvasive optical methods such as NIRS [J. Saliba, H. Bortfeld, D. J. Levitin, and J. S. Oghalai, "Functional near-infrared spectroscopy for neuroimaging in cochlear implant recipients," *Hearing Research* 338, 64-75 (2016)].

Still other classes of applications being developed from measures sensitive to changes in oxygen utilization by the brain are those based on biofeedback or responses to neuromodulation [R. Sitaram, T. Ros, L. Stoeckel, S. Haller, F. Scharnowski, J. Lewis-Peacock, N. Weiskopf, M. L. Blefari, M. Rana, E. Oblak, N. Birbaumer, and J. Sulzer, "Closed-loop brain training: The science of neurofeedback," *Nature Reviews: Neuroscience* 18, 86-100 (2017)]. One form of neuromodulation is the changes produced to the short- and long-term synaptic profiles of the brain in response to neural activation caused by applied pulsed magnetic fields [aka, transcranial magnetic stimulation (TMS)]. This strategy is used in the clinical management of depression and other psychiatric diseases, in recognition that these disorders are causally affected by factors leading to aberrant synaptic profiles. However, while such treatments can be effective, there is a need for more individualized treatment protocols because their effectiveness is sensitive to a host of details intrinsic to an individual's brain anatomy as well as the unseen connectivity properties of the brain. To minimize the impact of these uncertainties, measures of the TMS-induced coupled hemodynamic response to neuroactivation seen during treatment sessions, or shortly afterwards, have been proposed as a guide to treatment protocols under the hypothesis that the effectiveness of these treatments varies with the amplitude of this induced response [A. Curtin, J. Sun, H. Ayaz, Z. Qian, B. Onaral, J. Wang, and S. Tong, "Evaluation of evoked responses to pulse-matched high frequency and intermittent theta burst transcranial magnetic stimulation using simultaneous functional near-infrared spectroscopy," *Neurophotonics* 4, Article 041405 (2017)]. Another form of neuromodulation that can potentially benefit from guidance to applied protocols is treatments involving electrical stimulation of the brain, such as can be achieved by applying transcranial direct-current stimulation (tDCS). Similar to the TMS response, real-time access to induced responses provides a basis for implementing biofeedback-dependent protocols that support understandings of the effects being produced by the applied treatments.

In summary, the critical interdependence of tissue function and oxygen homeostasis predisposes tissues of various types towards multiple forms of sensitivity to disease and to respond to a wide range of manipulations, some of which may serve to guide treatments or to improve the performance of assistive devices.

Technologies and their Uses for Evaluating Factors Affecting Oxygen Delivery to Tissue:

Appreciation of the importance of oxygen delivery to tissue in these varied situations and environments has prompted the development of a variety of sensing methods to serve as guides to the detection and monitoring of conditions that warrant clinical attention. Among these are the methods of positron emission tomography (PET) [J. J. Vaquero and P. Kinahan, "Positron emission tomography: Current challenges and opportunities for technological advances in clinical and preclinical imaging systems," *Annual Review of Biomedical Engineering* 17, 385-414 (2015)], electron paramagnetic resonance (EPR) oximetry [R. Ahmad and P. Kuppusamy, "Theory, instrumentation, and applications of EPR oximetry," *Chemical Reviews* 110, 3212-3236 (2010)], and electrochemical electrode methods [Y. Wang, H. Xu, J. Zhang, and G. Li, "Electrochemical sensors for clinic analysis," *Sensors* 8, 2043-2081 (2008)], as well as the mentioned MM-BOLD technique and a variety of optical methods, including oximetry-based techniques (pulse oximetry and tissue oximetry) that may include additional signal transduction, as occurs in luminescence [T. Yoshihara, Y. Harakawa, M. Hosaka, and M. Nangake, "Oxygen imaging of living cells and tissue using luminescent molecular probes," *J. Photochem and Photobiol. C: Photochem. Rev.* 30, 71-95 (2017)] or in the photoacoustic effect [L. Wang and S. Hu, "Photoacoustic tomography: In vivo imaging from organelles to organs," *Science* 335, 1458-1462 (2012)]. Separate from these are techniques sensitive to blood flow. While these measures often are useful in themselves, they do not, however, directly support measures of oxygen delivery or its utilization. Also, while understandings provided can aid in the interpretation of measures that directly assess tissue oxygen levels or features of the hemoglobin signal, their use can be affected by added attenuation of acoustic signals from bone (cranium), limited sensitivity to the microvascular bed, or the added cost associated with the requirement for more complex sensing resources (Diffuse Correlation Spectroscopy) than those used by continuous-wave NIRS methods.

Among these methods, the MR-BOLD technique and various forms of optical sensing methods have shown the greatest promise. However, significantly limiting the former are its high cost, unsuitability for examining vulnerable populations (e.g., infants, individuals with embedded metal, subjects who are claustrophobic), and sensitivity to only a limited portion of the information that defines the principal phenomenology responsible for modulation of oxygen delivery. Being sensitive to only changes in deoxyhemoglobin, it is frequently unclear whether changes in the BOLD signal are due to changes in blood volume or in blood oxygenation. In contrast, optical-based oximetry methods, which include various implementations of near-infrared sensing techniques, are sensitive to the principal forms of Hb, thus yielding a total of five components (i.e., oxyHb, deoxyHb, totalHb, $HbO_2Sat$ and $HbO_2Exc$).

Having the longest history of clinical experience is the method of pulse oximetry. Diffuse transmission measurements are acquired from small appendages (e.g., fingers, toes), from which are reported measures of $HbO_2Sat$. Typically employed are sources that emit two wavelengths of light whose wavelengths are on either side of the 805 nm isosbestic point in the hemoglobin spectrum. Conversion of light intensity to measures of the relative change in hemoglobin levels is achieved using a modified Beer-Lambert equation that includes a differential pathlength factor to account for pathlength increases caused by scattering. Alternatively, this conversion can be accomplished by computing solutions to an inverse problem based on operators derived from solutions to the radiative transport equation or suitable approximations of it.

While pulse oximetry measures are typically accomplished using continuous wave (CW) techniques, equivalent measures can be accomplished using illumination-detection methods sensitive to expected time delays of light propagation in tissue caused by scattering (achieved using frequency-domain techniques), or to the time-dependent intensity profile observable with ultrafast optical methods. The presence of other intrinsic factors in tissue that influence light attenuation in the NIR spectral region can motivate use of additional wavelengths of light. These factors include absorption by water, lipid, melanin and mitochondrial cytochrome c oxidase, and the scattering of light by tissue.

Similar to the method of pulse oximetry are measures involving similar sensors but applied to bulk tissues, for example, measures of relative changes in brain oxygenation. An example here is the INVOS monitor offered by Coviden, which samples back-reflected light. Its primary difference from pulse oximeters is its incorporation of a correction factor intended to account for contributions from more superficial tissues.

In principle, roughly similar measures can also be achieved from strategies that measure the fate of light absorbed by tissue, which results in its conversion to heat, thereby generating a propagating pressure wave that can be measured using acoustic sensing methods. Referred to as the photoacoustic effect, this technique supports similar types of optical inspection of tissues, while offering the advantages of deeper signal penetration and improved resolution, if required, of recovered images. Also capable of assessing the different forms of the hemoglobin signal are recently described holographic methods that discriminate features of diffused light [E. Strickland, "Why Mary Lou Jepsen left Facebook: To transform health care and invent consumer telepathy," IEEE Spectrum—The Human OS, posted 15 Mar 2017. Available online at https://spectrum.ieee.org/the-human-os/biomedical/imaging/why-mary-lou-jepsen-left-facebook-to-transform-heath-care-and-invent-consumer-telepathy.]. Likewise, the methods of the present invention could be used for analysis of time-series data recorded in dynamic optical coherence tomography applications [S. Schuh, J. Holmes, M. Ulrich, L. Themstrup, G. B. E. Jemec, N. De Carvalho, G. Pellacani, and J. Welzel, "Imaging blood vessel morphology in skin: Dynamic optical coherence tomography as a novel potential diagnostic tool in dermatology," *Dermatologic Therapy* 7, 187-202 (2017)], provided that the technique is modified to illuminate the target tissue with two or more wavelengths of light (i.e., to permit recovery of deoxyHb and oxyHb time series) instead of the commonly employed single-wavelength approach [S. Schuh et al., *Dermatologic Therapy*]. Provided that time-series data are collected, the methods of the present invention also could be applied to analyze data recorded in structured illumination (aka, spatial frequency domain) measurements [S. Belanger, M. Abran, X. Intes, C. Casanova, and F. Lesage, "Real time diffuse optical tomography based on structured illumination," *J. Biomedical Optics* 15, Article 016006 (2010)], which has been shown to have promising utility for clinical problems such as assessing the severity of burn wounds [M. Jayachandran, S. Rodriguez, E. Solis, J. Lei, and A. Godavarty, "Critical review of noninvasive optical technologies for wound imaging," *Advances in Wound Care* 5, 349-359 (2016)].

Also considered by the NIRS technique, but involving use of arrays of optical sensors, are measures intended to explore the phenomenon of neurovascular coupling and the connectivity properties of the brain. These measures have captured growing attention by the experimental psychology community, in part because of their added promise to extend this class of measures to include investigations in unconstrained environments [S. K. Piper, A. Krueger, S. P. Koch, J. Mehnert, C. Habermehl, J. Steinbrink, H. Obrig, and C. H. Schmitz, "A wearable multi-channel fNIRS system for brain imaging in freely moving subjects," *NeuroImage* 85, 64-71 (2014); J. B. Balardin, G. A. Zimeo Morais, R. A. Furucho., L. Trambaiolli, P. Vanzella, C. Biazoli Jr., and J. R. Sato, "Imaging brain function with functional near-infrared spectroscopy in unconstrained environments," *Frontiers in Human Neuroscience* 11, Article 258 (2017)].

The capture of the time-evolving Hb response of the brain to behavioral tasks, or of coordinated behaviors that arise from its connectome properties, is typically accomplished using an array of optical sources and detectors that are configured in some defined alternating pattern and are placed in direct contact with body tissues. Typically, sensing hardware is introduced into a conforming fabric cap that is mechanically supported by added stabilizers or by use of more rigid support structures. Recognizing that the maximum penetration depth of light emerging from tissue varies with distance from a source, often considered are back-reflection measures wherein a detector is placed at a distance of approximately 3-4 cm from a source. Additional short-distance-detector measures intended to isolate contributions from more superficial tissues (e.g., scalp) also can be considered.

Related measures that also involve the use of arrays of optical sensors on bulk tissues are NIRS-based measures of the breast and other peripheral tissues (e.g., skeletal muscle, bladder). In such cases, the sensing arrays may comprise a low-profile pad containing light emitters (e.g., LEDs, laser diodes or vertical cavity lasers) and receivers [e.g., silicon photodiodes (SiPD), avalanche photodiodes (APD) and photomultipler tubes (PMT)]. Because breast tissue is, owing to its relatively low heme-protein content, less absorbing to near infrared light than, for example, skeletal muscle and the brain, full transmission and intermediate illumination-detection arrangements are feasible. Indeed, as shown by Al abdi et al. [R. Al abdi, H. L. Graber, Y. Xu, and R. L. Barbour, "Optomechanical imaging system for breast cancer detection," *J. Optical Society of America A*, 28, 2473-2493 (2011)], capture of full tomographic 3D image time series measures are feasible.

To capture a time series measurement, sensing arrays can be operated by employing schemes that range from full source-multiplexing, in which each source location is illuminated sequentially, to full frequency encoding, which allows for simultaneous detection of light from multiple sources for each detector position. The driving electronics needed to support these arrays can be housed locally in the form of a compact wireless amplifier, or be supported by a tether that transmits and receives electrical and timing signals from a desktop amplifier. Also feasible are non-contact measures wherein the target tissue is illuminated by a collimated source or with broad-area structured-illumination methods [A. Mazhar, D. J. Cuccia, S. Gioux, A. J. Durkin, J. V. Frangioni and B. J. Tromberg, "Structured illumination enhances resolution and contrast in thick fluorescence imaging," *J. Biomed. Opt.* 15, Article 0150506 (2010)]. Non-contact, broad-area illumination methods can also be applied with the aim of employing holographic techniques [E. Strickland, IEEE *Spectrum—The Human OS*]. Non-contact optical sensors can include discrete sensors (e.g., SiPD, ADP, PMT) or area arrays (e.g., CCD).

A principal focus of breast studies with NIRS has been the exploration of its potential utility for early diagnosis of breast cancer [D. R. Busch, R. Choe, T. Durduran, and A. G. Yohd, "Towards non-invasive characterization of breast cancer and cancer metabolism with diffuse optics," *PET Clinics* 8, 345-365 (2013)]or, alternatively, to serve as a confirmatory method [P. Taroni, A. M. Paganoni, F. Ieva, A. Pifferi, G. Quarto, F. Abbate, E. Cassano, and R. Cubeddu, "Non-invasive optical estimate of tissue composition to differentiate malignant from benign breast lesions: A pilot study," *Scientific Reports* 7, Article 40683 (2017)], and to provide guidance in determining the effectiveness neoadjuvant therapies [B. J. Tromberg, Z. Zhang, A. Leproux, T. D. O'Sullivan, A. E. Cerussi, P. M. Carpenter, R. S. Mehta, D. Roblyer, W. Yang, K. D. Paulsen, B. W. Pogue, S. Jiang, P. A. Kaufman, A. G. Yodh, S. H. Chung, M. Schnall, B. S. Snyder, N. Hylton, D. A. Boas, S. A. Carp, S. J. Isakoff, and D. Mankoff, "Predicting responses to neoadjuvant chemotherapy in breast cancer: ACRIN 6691 trial of diffuse optical spectroscopic imaging," *Cancer Research* 76, 5933-5944 (2016)]. Experience has shown that while the optical method is promising for detection of larger tumors, reliable detection of small tumors is notably more challenging. In an effort to overcome this, and recognizing that tumors are often more stiff than surrounding tissue, one strategy considered has been to employ the Valsalva maneuver [C. H. Schmitz et al., "Design and implementation of dynamic near-infrared optical tomographic imaging instrumentation for simultaneous dual-breast measurements," *Applied Optics* 44, 2140-2153 (2005)], or applied force [Al abdi et al., *JOSA-A*], or applied force, with the expectation that the response from affected tissue will differ in some discernible way from that of healthy tissue.

In summary, techniques are available that are sensitive either directly to tissue oxygen or to surrogate measures that include properties of hemoglobin and blood flow measures. Several implementations of NIRS—in particular, CW arrangements—have favorable flexibility, cost, and form-factor features, and can be applied either to small appendages or to bulk tissues of various types using sensing arrays. Analysis Methods and Experimental Techniques Applied to Evaluate Features Linked to Oxygen Delivery to Tissue:

Independent of the details of the sensing techniques used to explore features of the Hb signal is the various analysis methods employed to isolate features of interest. Motivating a particular strategy is the expectation that selected features are recoverable with sufficient fidelity to allow for their useful detection, often with the goal of monitoring how values may change in response to treatment or whether measured values exceed expected limits. However, in many instances, target features can be obscured by the impact of artifact or by the presence of other signals that can overlap with the features of interest but are not considered to originate from the tissue target of interest. The origin of these overlapping signals can be traced to contributions from spatial features of tissue, or from intrinsic dynamic behaviors that overlap with the target feature.

An example of the former is the use of near-distance detector measures, employed in cerebral oximetry studies, that preferentially sample light confined to the superficial elements of tissue (e.g., scalp), thereby allowing for regression of these signals from those sampled by detectors positioned at longer distances, which unavoidably include contributions from near-surface and deeper-lying tissues. Roughly equivalent outcomes can be achieved in the cases where high-density arrangements of sensors are applied and acquired measures are processed using tomographic reconstruction methods. The advantage of these is their ability to spatially resolve signal features that have been spatially convolved.

In situations where signal convolution is due to overlapping temporal features, target features may be resolvable if background signals exhibit different frequency structure, or if the temporal profile of background signals is substantially uncorrelated with or independent of target behaviors. Recognizing that neither of these conditions is prominent in the cases where the aim is to detect neuroactivation in response to stimuli, attention to details of the experimental protocol has shown that effective strategies can be found. Because the timing of stimuli can be made mainly independent of the roughly periodic intrinsic vascular signals, use of simple event averaging serves to suppress these contributions. Also, because the details of the protocol are known, its timing information can be used to synchronize response measures to applied regression methods. A common strategy is the method known as statistical parametric mapping (SPM), which employs the general linear model to determine whether goodness of fits of a defined function (usually a form of a gamma variate function) to the measured response exceeds statistical expectations.

Other methods have the aim of appreciating whether intrinsic temporal features may be correlated with others, but are spatially distinct. Simply applied are computations of time correlation, which reveal the correlation value as a function of the time lag. Recognizing that the propagation of neural signals produces a network of signaling whose features are spatially distinct and often directed, other methods can be applied that are sensitive to this property. Notable here is the method of Granger Causality, which can reveal these features in instances where that are directly observable, and the method of Dynamic Causal Modeling, which can additionally recognize these in cases where some network features are hidden.

Another experimental method used to appreciate properties of the hemoglobin in tissue is the use of perturbation methods. When employed, the aim of these techniques typically is to extract some measure(s) of system response that serves to differentiate behaviors attributable to different subject groups or types or details of applied perturbation. The form of the perturbation can vary significantly and includes exploring the response to actions of drugs, to various stimuli or to physical maneuvers such as inflation of a pressure cuff, and respiratory challenges, among others. This class of maneuvers can be applied over a wide range of tissue types. For instance, because diabetes affects the vascular endothelium, hyperemia in response to cuff inflation is often attenuated. In the case of behavioral studies intended to explore brain function, perturbations methods frequently involve measuring responses to specific stimuli.

A particular advantage of this approach is the expectation that often it is not necessary to have prior knowledge of the details governing system behavior; instead, it is sufficient to consider only the response. In many instances the expected response is some change in signal amplitude tied to the applied perturbation, which often can be easily discerned. In other situations, where the effect seen is either not acute or is more subtle, detection of response can be more challenging. Useful strategies here include the above-mentioned methods for resolving overlapping temporal behaviors, in particular those that may be uncorrelated and independent.

In practice, the hypothesis that observed responses can aid in classifying and quantifying features that may support, for example, disease detection or discrimination, can be complicated should the response itself depend on other factors such as the presence of common subclinical factors such as arterial vascular disease. Yet another concern is that, while perturbation methods offer flexibility in how they can be imposed, the details of discerning which amplitude, duration, and type should be applied to isolate useful features can require invoking systematic exploration and refinement of methods, and these efforts can require significant computational support. Still another confound is the influence of expected variability in subject compliance should the protocol require this, or in the details of how a target tissue (e.g., breast, arm, leg) may respond owing to inter-subject variability in boundary conditions resulting from varying tissue dimensions.

While perturbation methods are used in many contexts, including in clinical medicine for disease diagnosis (e.g., cardiac stress test), experience shows that there are many circumstances where they are not easily employed, or are otherwise contraindicated, or are simply infeasible.Examples include hospitalized patients who may be immobilized or unconscious, and patients whose participation in a specified maneuver is deemed unsafe (e.g., subjects with severe heart disease), among others. The form of these restrictions does not necessarily depend on invoking perturbations that may require extreme exertions or are potentially otherwise hazardous. For instance, it is obviously challenging to acquire measures of event-related neuroactivation to a mental task from someone whose is unconscious. Nevertheless, there are circumstances in which the state of consciousness can be ambiguous. This is the case in subjects who are minimally conscious due to effects of various diseases.

Separate from perturbation methods are methods intended to explore expected functional relationships that can be defined via physiological models [S. Fantini, "Dynamic model for the tissue concentration and oxygen saturation of hemoglobin in relation to blood volume, flow velocity, and oxygen consumption: Implications for functional neuroimaging and coherent hemodynamics spectroscopy (CHS)," *NeuroImage* 85, 202-221 (2014)]. While the performance of these methods in some cases has shown good promise, it is difficult to quantify the expected influence of disease on the reliability of computed quantities, many of which are not directly observable. Also presenting a challenge for this class of methods is the mismatch in dimensions (several orders of magnitude) between the spatial scale explored by MR-based and optical methods and the spatial scale corresponding to the features of interest involving the microvascular bed.

In summary, while Hb features-of-interest for various tissues can be identified from spatial and temporal regression methods, physiological models, and from application of perturbation methods, a mainly unsolved confound are situations where the latter methods are considered unsuitable.

Solution to Problem of Evaluating Complex Response of Hemoglobin Signal

In cases where adoption of perturbation methods is not feasible, remaining are measures of the resting state or at least those that closely approximate a resting state. A clear advantage of this approach is that it is often easiest to invoke, is well suited for vulnerable populations, and is the most adaptable to different clinical and experimental environments. Indeed, such types of investigation are common, as evidenced by the many forms of continuous monitoring that are employed in hospital settings (e.g., ECG, pulse oximetry, respiratory measures). In addition, this capacity currently extends to assessment of functional features of the brain, including measures of connectivity that can be determined from the resting state, and well as measures of neuroactivation that, while not strictly resting-state protocols, nevertheless are frequently acquired under conditions that constitute substantially low activity.

However, while these capabilities are available, extension of resting-state measures to other tissue classes, such as the breast, initially would seem less appealing because, unlike the brain, the breast and other tissues lack the distinctive anatomical elements that can drive specialized functional responses (e.g., connectivity, localized responses of neurovascular coupling). Nevertheless, the considerable feasibility advantages supported by this class of measures warrant a more thorough consideration of precisely how useful implementations might be achieved.

The principal understanding we considered has been to recognize that closely tied to the influence of a disease is its impact on network behaviors. Simply stated, true networks reflect behaviors that in some way are causally linked. While the strengths of these linkages can vary, disturbances in one part of the network are expected to produce disturbances in other areas. Often viewed as having network properties are feedback mechanisms that modulate various biological functions that exist on cellular, tissue, whole organ and system-wide levels [C. H. Schilling and B. O. Palsson, "The underlying pathway structure of biochemical reaction networks," *Proc. Natl. Acad. Sci.* 95, 4193-4198 (1998); P. R. Somvanshi and K. V. Venkatesh, "A conceptual review on systems biology in health and diseases: From biological networks to modern therapeutics," *Systems and Synthetic Biology* 8, 99-116 (2014)]. Network behaviors can be strongly influenced by functional or structural properties that are in some way linked. Principal examples of structural networks include the peripheral nervous system, the vascular tree, and the elements of brain anatomy that have distinct anatomical neural pathways, mainly through features of white matter. Functional networks involve coordinated behaviors that do not require a fixed pathway to exert their effects, and often have the property of action-at-a-distance. A prime example is the myriad of behaviors produced by the endocrine system. In practice, networks behaviors operating on various spatial scales are influenced by both classes.

Biological networks also exhibit distinct temporal behaviors that operate on different time scales. Rhythmic behaviors include the rapid events of synaptic transmission [K. B. Hengen, A. T. Pacheco, J. N. McGregor, S. D. Van Hooser, and G. G. Turrigiano, "Neuronal firing rate homeostasis is inhibited by sleep and promoted by wake," Cell 165, 180-191 (2016)] and even more rapid electrical signaling mechanisms [A. E. Pereda, S. Curti, G. Hoge, R. Cachope, C. E. Flores, and J. E. Rash, "Gap junction-mediated electrical transmission: Regulatory mechanisms and plasticity," Biochim. Biophys. Acta 1828, 134-146 (2013)], as well as other behaviors that range from the cardiac and respiratory rhythms to circadian and hormonal (menstrual) cycles.

Being confined to the vascular space, network influences that affect that vascular tree can be expected to also influence behaviors of the hemoglobin signal. Thus, for instance, it is well appreciated that vasodilation is accompanied by an increase in totalHb levels. Because this response leads to an influx of more highly oxygenated blood from arterial sources, changes in blood oxygenation frequently accompany the changes in blood volume. These adjustments are the principal actions produced by vascular and tissue feedback mechanisms in response to varying metabolic needs of tissue. As mentioned, this phenomenology, generally referred to as tissue-vascular coupling, of which neurovascular coupling is a special case, is believed to occur in all tissues to varying degrees.

While the preceding is well understood, the common practice of exploring elements of the hemoglobin signal separately overlooks the principal phenomenology of network behaviors, which as mentioned is expected to cause multiple elements of a network to co-vary. That network features are not easily discerned from independent inspection of the individual elements follows because the principal behavior in one part of a network often can be quite different than that of another. Also recognized is that the factors responsible for promoting causative interactions within a network are often not simply a linear sum of behaviors that might be discerned from its individual components.

Another feature closely tied to the time-varying behaviors of networks is their sensitivity to nonlinear influences. One consequence of this, and a common behavior of many time-varying systems (physical and biological), is that these influences can have the effect of driving system behaviors from one preferred state to another. While these transitions arise as a consequence of continuous interactions among state variables, discrete representations of this behavior is easily adopted by simply collapsing details of the time domain. The effect is to represent what otherwise can be complex system behaviors as, instead, a system of discrete states that undergo transitions from one state to another in accordance with an assignable set of probabilities. Putting aside for the moment the details of how such states should best be defined and at what level of granularity, what is achieved by this representation is an explicit description of a network of interconnected states from which, as will be shown, a wide range of coefficients can be determined. While elements of the vascular tree do form a structural network, the properties we consider do not directly follow from this. Instead, the network we consider is a functional one that arises from the actions of feedback mechanisms whose effects can be spatially and temporally distributed in tissue, but share a common dependence on particular features of the Hb signal.

Being responsive to feedback mechanisms, behaviors observed in the resting state modulate about a temporal mean, which in the case of NIRS measures produces five co-varying quantities.

Categorical representations of these (FIG. 1, Table 1), based on their algebraic signs relative to their respective temporal mean values, leads to the assignment of ten distinct classes, each of which contains elements from the five different components of the Hb signal. Referred to hereafter as Hb-states, distinguishing one state from another is a unique combination of the algebraic assignments of the mentioned classes. Also, because the instantaneous amplitude of each Hb-component varies with time, state assignments that follow from their algebraic-sign assignments also will vary. This leads to a description of state transitions wherein a transition from any one state to any other can occur.

Examination of co-varying features of Hb has been considered by our research group [G.W. Wylie, H.L. Graber, G.T. Voelbel, A.D. Kohl, J. DeLuca, Y. Pei, Y. Xu, and R.L. Barbour, "Using co-variations in the Hb signal to detect visual activation: A near infrared spectroscopic imaging study," NeuroImage 47, 473-481 (2009)] and others [K. Yoshino and T. Kato, "Vector-based phase classification of initial dips during word listening using near-infrared spectroscopy", NeuroReport 23, 947-951 (2012); K.S. Hong and N. Naseer, "Reduction of delay in detecting initial dips from functional near-infrared spectroscopy signals using vector-based phase analysis", Int. J. Neur. Sys. 26, 1650012 (2016)] in different contexts. Not recognized by either is the network formalism employed here. The prior art differs from the invention described here in terms of the temporal span of the measures from which coefficient values are determined, and in the underlying theory applied to generate them. In the cited reports (and related work), coefficient values are based on instantaneous measures of a time-evolving process [T. Kato, "Apparatus for evaluating biological function, a method for evaluating biological function, a living body probe, a living body probe mounting device, a living body probe support device and a living body probe mounting accessory," U.S. Pat. No. 8,406,838 B2]. In contrast, because we believe that the underlying processes that drive feedback mechanisms operate as a network with a spatially and temporally varying matrix of transition time-constants, the coefficient values that we compute are based on processes that exhibit varying dwell times. Also different is the fundamental theory governing feature generation. Our methodology is motivated from an understanding of stochastic networks, in recognition that feedback behaviors affect not one, but many factors that interact. Recognizing that instantaneous values of co-varying measures trace a trajectory in (deoxyHb, oxyHb)-space (FIG. 1, or its equivalent in the cited reports), the authors of the prior work have sought to apply principles of the physics of moving bodies as a strategy to explore features of these trajectories. While it is not necessary for applied mathematical formulations to have a strong biological correspondence, arbitrary adoption of laws that are relevant to one field but not applicable to another risks production of reification fallacies.

While the noted understandings support appreciation of how network measures might be accomplished, explicit definition of coefficient values requires invocation of two other strategies. One of these is the method by which state transitions are defined. While the methods considered were motivated by understandings of finite Markov chains (FMC), modifications have been made to this approach. For instance, rather than considering transitions that occur on a fixed-time basis, methods outlined in the preferred embodiment compute them from measures that have variable dwell times, in recognition that feedback mechanisms in bulk tissues likely operate with different time constants. Also important is to appreciate the various classes of coefficients that can be derived. In addition to computing the matrix of transition probabilities among the defined states, as follows from methods based on FMC analysis, we recognize that also available are measures of state transition rates and of flux measures assignable to each individual component in a given state. Also considered are several associated coefficient arrays that appreciate qualitative and quantitative dependences among these features, as well as associated asymmetries that depend on the direction of the transition (e.g., A→B vs. B→A). It is further understood that methods of analysis of network behaviors constitute a broad activity space, for which a wide range of additional coefficient classes can be derived.

In practice, what constitutes suitable conditions for the suggested measures can likely be expanded beyond a strict resting state. While preferred measures involve subjects in the seated or supine position and substantially at rest, it would seem feasible to impose dynamic low-amplitude Trendelenburg maneuvers as a stimulus to the autonomic response. Also feasible should be static repositioning maneuvers having higher amplitudes. Still other protocols could involve slow-speed walking on a treadmill, with target measures involving tissues in the head or upper torso. Alternatively, if cuff inflations are considered, they could be limited to the lower extremities, with target measures involving tissues in the head or upper torso. Other protocols could consider inspiration of different respiratory gas mixtures that could include elevated levels of $CO_2$, or elevated or reduced levels of oxygen. Also having value could be instances where to aim is to appreciate the influences of new drugs or drug interactions. In all of these cases the target tissue response can include, but are not limited to, measures of the head (brain), skeletal muscle, limbs, breast foot or other peripheral tissues, as well as those accessible in endoscopic procedures. In these cases, the preferred measure is CW NIRS arrays. Also considered are the noted instances of disease in the form of cancer, diabetes, autoimmune disorders, and others that are known to influence oxygen homeostasis, as well as the exemplary neuromodulation methods applied to brain, and identified neuroimplants. In cases where it is suspected that the affected tissue has a unilateral presentation, still another strategy would be to acquire substantially bilateral measures (e.g., simultaneous bilateral breast measures), with one region serving as a reference for the other.

In summary, resting state measures are easily applied, suitable to vulnerable populations, and highly adaptable to clinical or subject constraints. This invention introduces the first understanding that co-varying features of the hemoglobin signal can be interpreted as a functional network, which is accessible from such measures.

Alternative Methods to Achieve Solution to Measures Evaluating Representations of Network Dependent Features of the Hemoglobin Signal in Living Tissues Descriptions of network behaviors involving connectivity among the nodes constitute representations that have been adopted by a large number of communities. More formally, such descriptions are an aspect of the field known as Discrete Mathematics, whose methods have touched applications in systems-level biology, multiple areas in computer science, linguistics, economics, chemistry, physics, and other fields. The understanding that network behaviors can be reduced to various graphical representations emphasizes that Graph Theory is a relevant sub-field of discrete mathematics. When system behavior is principally governed by stochastic processes, teachings from the field of Stochastic Network Theory can be informative. Other descriptions are also available. For example, it is understood that in some instances details of network behaviors can be shown to follow defined rules. Basic teachings from the field of linguistics have shown that such rules can be organized in a hierarchy and that rule-based hierarchies provide a formal structure to information transduction. These understandings come from the field of Formal Language Theory (FLT) and were introduced by the distinguished linguist, Noam Chomsky, in the 1950s. Applications of FLT have been advanced in many fields, in particular in the development of computer languages and efforts to decode rules that govern the multiple forms of macromolecular structures (e.g., DNA, RNA, proteins) that provide the molecular templates for transcription of the principal elements of cells.

Experience gained from these fields of study has revealed that information accessible from the applied methods can extend beyond feature descriptions that are directly observable. For instance, methods derived from FLT have aided in the design of new drugs [H. Ikebata, K. Hongo, T. Isomura, R. Maezono, and R. Yoshida, "Bayesian molecular design with a chemical language model," *J. Computer Aided Molecular Design* 31, 379-391 (2017)] based on understandings of languages developed to allow rigorous chemical structure specification by means of a very small and natural grammar (i.e., set of rules) [D. Weininger, "SMILES, a chemical language and information system. 1. Introduction to methodology and encoding rules," *J. Chemical Information and Computer Sciences* 28, 31-36 (1988)]. Also appreciated from understanding of methods used to evaluate Hidden Markov Chains is the potential to discover features that are not directly observable. Listed herein are exemplary strategies wherein the identified feature spaces can be extended in accordance with these understandings.

A principal outcome from the developed approach has been the demonstration that a finite-state network representation of the co-varying elements of the hemoglobin signal provides access to a previously unrecognized dense feature space whose coefficient values appear mainly independent of each other. Potentially representing information having many degrees of freedom, this outcome holds significance for a wide range of applications whose aims can include distinguishing one class of features from another. As outlined more fully below, and previously noted, this can include impact of disease or other injuries, as well as the documenting of desired or undesired responses of tissue to various stimuli or treatments.

Fostering this potential is the experience gained from methods applied to evaluate data generated from other information-rich measures of biological systems. Of note are the strategies applied to the growing class of genomic, proteomic, metabolomic and other information classes (e.g., RNA), generally referred to as "—omics" technologies, which, owing to its discriminatory potential, is the leading approach in the Precision Medicine Initiative. Yielding, in some cases, thousands of coefficient measures, various classes of machine-learning methods (e.g., supervised, unsupervised and reinforcement learning methods), as well as the growing class of deep-learning methods, appear well-positioned for distinguishing features assignable to different diseases, or different responses to treatments, including undesired responses to drugs, and for fostering improved NIRS-based brain-computer applications (e.g., thought-based communication), biofeedback and many other uses.

Compared to the currently available methods employed to explore NIRS measures, most of which are perturbation-based, the new methods described in this application are well-suited for exploring substantially resting-state measures while yielding access to a dense and information-rich feature space. Exploitation of the resting state overcomes intuitive barriers that have hampered development of NIRS-based methods for studying the many disease processes that are known to affect peripheral tissues (e.g., breast cancer). Additionally, by providing access to features that are responsive to a common pathway (i.e., actions of feedback mechanisms through tissue-vascular coupling), the described methodology leverages basic understanding of biological behaviors (i.e., network properties) that have resisted consideration by the NIRS community. In contrast, although perturbation-based methods do offer a level of flexibility, when they are employed the observed responses are likely to prove sensitive to boundary conditions (e.g., small differences in applied force, influence of different body shapes, size, etc.), among other concerns.

Still another advantage of the methods described here, in comparison to existing methods appreciated in the prior art, is that the domain of information considered allows access to multiple well-developed analysis frameworks (e.g., Graph Theory, FLT, Stochastic Network Theory) that are likely to allow access to additional features that are currently unobservable. It is further recognized that, because the described methodology is based on evaluation of the hemoglobin signal, the described methods are expected to apply to other sensing strategies that may be used to capture this information, such as photoacoustic measures ["Photoacoustic Tomography," Chapter 12 in L.-V. Wang and H. Wu, *Biomedical Optics: Principles and Imaging* (Wiley-Interscience, 2007), pp. 283-317], and recently described holographic techniques [E. Strickland, IEEE *Spectrum—The Human OS*].

In summary, by representing co-varying features of Hb signal as a functional network, several well-developed, alternative methods can be applied to evaluate network features in the resting state, in addition to those considered by the preferred embodiment. Generated from these is a dense feature space with many degrees of freedom, emphasizing the likely value of machine learning and related techniques to support specific application development.

Investigative Uses of Network Properties of the Hb Signal in the Resting State:

While various tools have been developed that support measures sensitive to oxygen delivery to tissue, the environment and clinical status that patients encounter as a consequence of the applied treatments or of effects of disease limits the utility of protocols and technologies that otherwise might prove informative for investigative purposes. Contributing to these restrictions are limitations arising from system form factors, technical limits imposed by the likely need for long-duration monitoring, cost, and limits on the class of information currently accessible. What is currently not available, would have significant value, and can be accomplished by the disclosed invention is an easily applied and economical investigative resource for which the uncertainties in its utility are limited to the testing of hypotheses, such as whether the accessible information can serve to yield new understandings regarding the impact that disease and treatment regimens have on tissue function as a consequence of factors affecting oxygen delivery to tissue and its use.

As an example, commonly encountered in clinical situations are variations in blood pressure. Normally, compensatory effects caused by autoregulation in the brain serve to offset the impact that an ensuing decline in blood flow would have absent of this response. While the general features of the autoregulatory response are well appreciated, its details, which are likely situation-dependent, are largely unknown. The understanding that autoregulatory failures can produce states of either hypo—or hyperperfusion, argues for the need to detect such instances and to have effective countermeasures. Having general utility are measures sensitive to blood flow and to the hemoglobin signal. While various methods are available that supply elements of this need including, for example, fMRI, Doppler Ultrasound, Diffuse Correlation Spectroscopy, Photoacoustic Imaging and NIRS measures, in their current forms, all are limited by one of more the above noted restrictions. However, as disclosed in the current invention, the NIRS technique, which is easily adopted to acute-care settings, stands to yield maximum benefit for this exemplary problem.

Separately, the considered novel resource would also have significant value for preclinical uses. Of interest here are the many classes of manipulations intentionally imposed on animal models in pursuit of development of new drugs or other disease treatments, or to extend basic understandings of the systemic dependences that accompany these manipulations. For instance, much effort is devoted to establishing animal models that have specific disturbances in gene expression, immune response, or properties of the microbiome. While a range of toxicity measures and functional measures of principal organ function is currently established, mainly lacking are tools that can evaluate the impacts of these manipulations on the information domain of oxygen delivery to tissue in the intact animal, especially in the form of a non-invasive, high throughput screening method. Appreciation of the importance of this information domain with regard to overall health, and the observation that many classes of drugs that have met the criteria for human trials go on to fail because of unanticipated side effects, suggest that added attention to this basic feature of tissue function is likely warranted. This goal can readily be accomplished with methods described herein, by trans-illuminating nude animals in a confined space that provides easy access and egress while allowing for observations of the animals while they are in the resting state.

In summary, investigative studies, especially those in preclinical stage, stand to gain significantly from novel understandings that are easily generated by methods described herein.

SUMMARY OF THE INVENTION

Described as a first representation are methods and alternatives that cast co-varying features of the Hb signal as a functional network from measures that substantially comprise a resting state. Explored more fully in the preferred embodiment are clinical findings from CW NIRS array measures that explore a representative disease process (breast cancer) and document recovery of a previously unrecognized dense feature space that has many degrees of freedom and promising diagnostic potential, even when limited to univariate measures. Also demonstrated are quantitative understanding consistent with basic chemical theories that give high confidence in the fidelity of described methods.

In one aspect of the invention, the invention is a non-invasive method of detecting breast cancer in a patient. At least two hemoglobin signal components of hemoglobin levels are non-invasively measured in at least one breast of the patient over time. First time varying changes of at least a first of the hemoglobin signal components are measured with respect to at least second time varying changes of a second of the hemoglobin signal components. A co-varying coordinate system of the plurality of time varying changes is generated. Any cancerous tissue in the measured breast is detected from a signature of the measured breast in the co-varying coordinate system which differs from a signature of non-cancerous tissue in the co-varying coordinate system.

Preferably, transitions of the hemoglobin signal components from at least one hemoglobin state to another hemoglobin state are detected. Rates of the transitions are determined. Values of the rates of the transitions are mapped. Patterns are discerned in the values indicative of presence or absence of cancerous tissue. Preferably, five hemoglobin signal components are measured: oxyHb, deoxyHb, total Hb (totalHb =oxyHb +deoxy Hb), Hb oxygen saturation ($HbO_2Sat$ =(oxyHb/totalHb)*100), and tissue-hemoglobin oxygen exchange ($HbO_2Exc$ =deoxyHb −oxyHb).

Optionally, the tissue is measured optically. Optionally, the breast is illuminated with light, and at least one of diffusely transmitted or back-reflected light from the breast is/are measured.

In another aspect of the invention, the invention is a non-invasive method of detecting anomalous tissue in a patient. At least two hemoglobin signal components of hemoglobin levels are non-invasively measured in at least one segment of tissue of the patient over time. First time varying changes of at least a first of the hemoglobin signal components are measured with respect to at least second time varying changes of a second of the hemoglobin signal components. A co-varying coordinate system of the plurality of time varying changes is generated. Any anomalous tissue in the measured segment of tissue is detected from a signature of the measured segment of tissue in the co-varying coordinate system which differs from a signature of non-anomalous tissue in the co-varying coordinate system.

Preferably, transitions of the hemoglobin signal components from at least one hemoglobin state to another hemoglobin state are detected. Rates of the transitions are determined. Values of the rates of the transitions are mapped. Patterns are discerned in the values indicative of presence or absence of anomalous tissue. Preferably, five hemoglobin signal components are measured: oxyHb, deoxyHb, total Hb (totalHb =oxyHb +deoxy Hb), Hb oxygen saturation ($HbO_2Sat$ =(oxyHb/totalHb)*100), and tissue-hemoglobin oxygen exchange ($HbO_2Exc$ =deoxyHb −oxyHb).

Optionally, the tissue is measured optically. Optionally, the segment of tissue is illuminated with light, and at least one of diffusely transmitted or back-reflected light from the segment of tissue is/are measured. The anomalous tissue to be detected includes at least one of cancerous tissue or injured tissue.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 5(a), 5(b), and 5(c) are graphical representations of transition rate constants (units are $s^{-1}$), for subjects with unilateral breast cancer; computed using Eq. (3), in accordance with the invention. FIG. 5(a): data for tumor-bearing breast; FIG. 5(b): difference between tumor-bearing and contralateral, unaffected breast; FIG. 5(c): p-values for (unpaired) t-tests comparing the inter-breast differences for subjects with and without breast cancer, all in accordance with the invention.

FIG. 6(a): data for tumor-bearing breast; FIG. 6(b): difference between tumor-bearing and contralateral, unaffected breast; FIG. 6(c): p-values for (unpaired) t-tests comparing the inter-breast differences for subjects with and without breast cancer, all in accordance with the invention.

FIG. 8(a): each (ΔdeoxyHb,ΔoxyHb) data point (units are moles-$L^{-1}$) is joined to the origin by a line segment, to emphasize the angular discrepancies between T (red) and U (blue) values. FIG. 8(b) plot of the ratio (dimensionless) of each of FIG. 8(a) data point's projections onto the $ΔHbO_2Exc$ and ΔtotalHb axes (see FIG. 1), showing the tendency of the T breast to mount a relatively smaller blood-volume response to changes in tissue oxygen demand, in accordance with the invention.

FIGS. 15(a) and 15(c): transition mass of ΔtotalHb and ΔHbO$_2$Sat (units are moles-L$^{-1}$ and percent, respectively), for the tumor-bearing breast of the breast-cancer subjects; computed using Eq. (7). FIGS. 15(b) and 15(d): relative percent difference (dimensionless) between the transition masses for ΔtotalHb and ΔHbO$_2$Sat, respectively, comparing the affected and unaffected breasts of the same subjects, all in accordance with the invention.

DETAILED DESCRIPTION OF THE INVENTION AND DRAWINGS

Figure 1:
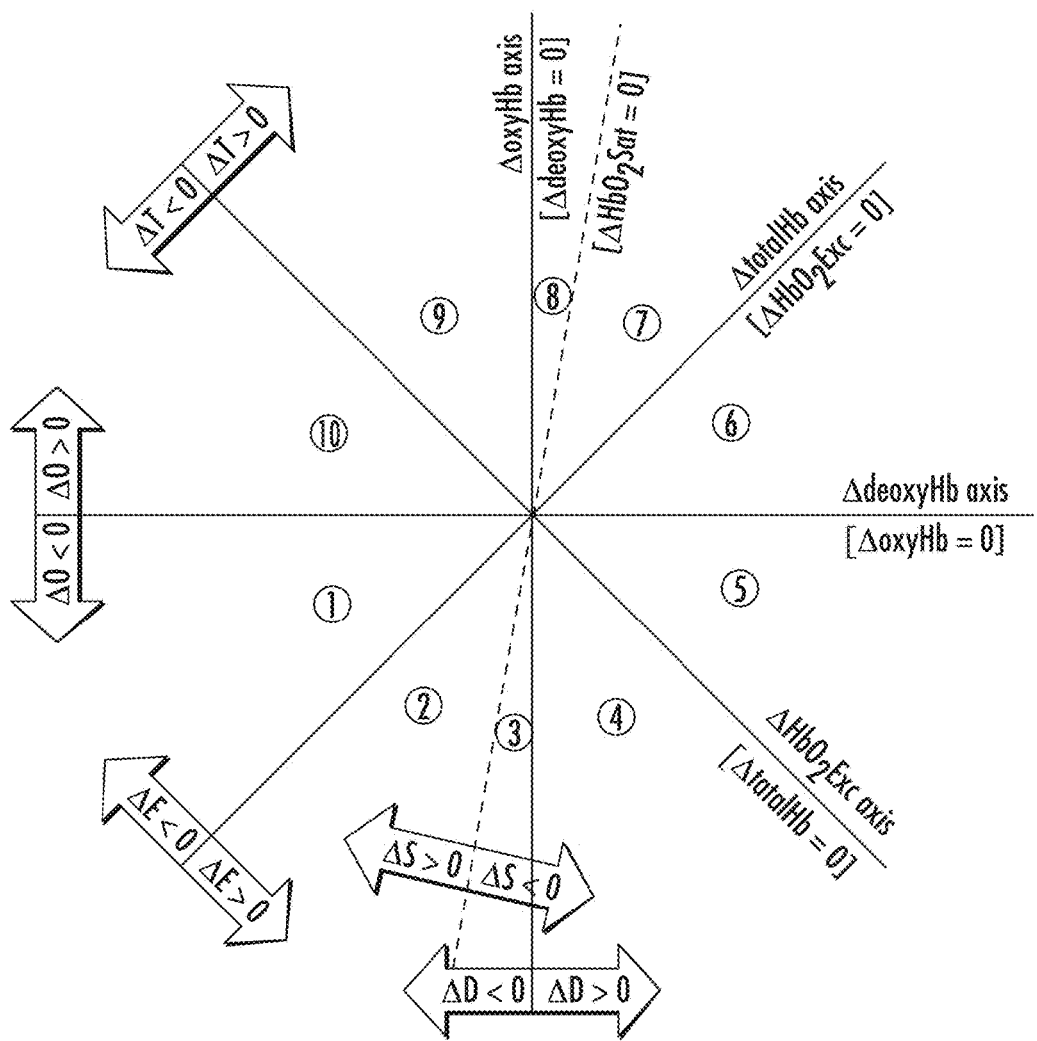
FIG. 1 is a graphic representation depicting Regions in (ΔdeoxyHb, ΔoxyHb) space that correspond to increasing or decreasing values, with respect to temporal mean, for each commonly considered component of the Hb signal, in accordance with the invention.

Description will now be given with reference to the attached FIGS. 1-16. It should be understood that these figures are exemplary in nature and in no way serve to limit the scope of the invention, which is defined by the claims appearing hereinbelow.

Method of Procedure for Acquiring Time-Series Measures of Hb Signal.

Step 1. Target tissue(s), which can include, but are not limited to the breast, limbs, wrist, finger, head, neck, torso, shoulders or feet, is illuminated using either contact or non-contact methods comprising at least one source, and diffusely transmitted or back-reflected light is measured using either contact or non-contact optical sensing elements comprising at least one receiver. When using arrays of discrete sources, source encoding can be accomplished using methods that vary from full time-multiplexing to full frequency encoding methods. Illumination from a given source is achieved using at least two wavelengths of light, which can include discrete or broad area illumination techniques. Optical detection of reemitted light is achieved using receivers operated to recognize the intensity, amplitude and phase, temporal or corresponding structured-spatial properties (e.g., as is employed in spatial frequency domain imaging) of the applied illumination. When appropriate, system gain values are adjusted to the individual to ensure acquired signal values are within the system's operating range.

For contact-based measures, applied sensors (emitters and receivers) can be stabilized with added mechanical supports that can include use of flexible links to form an interconnected lattice which can be made to conform to nonuniform tissue boundaries. Alternatively, these can be introduced within a fabric cap to conform to head geometries of varying sizes (Easycap). Also available are sensing arrays that can be housed within a low-profile pad whose driving electronics can be accomplished through a nearby wireless amplifier or by use of an electronic ribbon cable that serves to transmit power and timing signals. Also, light transmission and collection of reemitted light can be accomplished by use of optical fibers whose contact with the body is stabilized by suitable support structures. Also, the ease by with optical measures can be introduced into an endoscopic format, indicates that tissues accessible by this class of techniques could also be examined.

Step 2. Data collected in (1) is performed on subjects who are either in the seated, supine or prone position, or other body orientation(s) for which the tissue(s) under investigation are substantially stabilized. Should the data-collection protocol impose perturbations, these are employed in ways that do not overtly render target tissue measures unstable.

Step 3. Data collection involves capturing a time-series of measures.

Step 4. Collected wavelength data is transformed to Hb values by applying a modified Beer-Lambert transform to yield values of oxyHb and deoxyHb which are subsequently normalized to their respective temporal mean values. If required, these measures can be further processed to yield computed values of totalHb, $HbO_2Sat$ and $HbO_2Exc$. Also, if desired, acquired wavelength-dependent time series measures can be additionally transformed to form a wavelength-dependent tomographic absorption image time series by applying suitable inverse transforms, followed by subsequent conversions that equate changes in Hb concentration to the product of the wavelength-dependent extinction coefficient and computed change in the position-dependent absorption coefficient.

Method of Procedure for Transforming Time-Varying Measures of Hb Signal to Yield Coefficients of Network-Dependent Features of the Hemoglobin Signal.

1. Time series of deoxyHb, $HbO_2Exc$, $HbO_2Sat$, oxyHb and totalHb, computed via the steps outlined in the preceding section, are loaded into computer memory for post-processing.

2. The Hb-state corresponding to each image voxel (or source-detector channel) and time frame is computed as follows.

a. A three-dimensional temporary data-storage array is created, having the same number of rows (i.e., time frames) and columns (i.e., voxels or channels) as the data arrays loaded in Step 1, and having five layers that correspond to the five components of the Hb signal. The initial value of every array element is 0.

b. Every element of the array created in Step 2.a is assigned a value of either −1 or +1, depending on whether the value for the Hb-signal component corresponding to the layer-index value, at the time frame corresponding to the row-index value, is less than or greater than that same component's mean value at the voxel or channel location corresponding to the column-index value. Ten distinct permutations of '±1' values are logically possible and physiologically plausible. A lookup table, assigning each of these permutations to an integer in the 1-10 range, is generated.

c. A two-dimensional permanent data-storage array is created, having the same number of rows and columns as the data arrays loaded in Step 1. The initial value of every array element is 0. Every element of this array is then assigned an integer value in the range of 1 to 10, by consulting the lookup table described in Step 2.b.

3. Transition-count information is computed as follows.

a. A three-dimensional data-storage array is created, having ten rows, ten columns and a number of layers greater than the expected (based on prior experience) maximum persistence of a channel or voxel in any one Hb-state (e.g., 60 were used for exemplary computations). The initial value of every array element is 0.

b. The Hb-state array generated in Step 2 is scanned, starting from the first row and first column; proceeding through each succeeding row of the first column until the last row is reached; then to the first row and second column; the last row of the first column, then through each succeeding row of the second column until the last row is reached; then to the first row and third column; and continuing in this manner until the last row, final column is reached.

c. At the start of each transition-count operation, the Hb-state value at the current row-and-column position (by definition, row i and column j) is compared to the Hb-state value in row i+1, column j. If the two Hb-state values are different, then (by definition) a transition has occurred. If not, the row i+1, column j Hb-state value is compared to the row i+2, column j value, then to the row i+3, column j value, etc., until either a transition is observed or the end of the row is reached.

d. If, in Step 3.c, a transition is observed between the row i+1, column j and row i+1, column j+k Hb-state values, the value of an element in the $k^{th}$ layer of the array created in Step 3.a is increased by 1. The column coordinate of the selected array element is equal to the Hb-state value at the pre-transition time frame, and the row coordinate is equal to the Hb-state value at the post-transition time frame.

e. After the entire array of Hb-state values is scanned, transition probabilities are computed by applying Eq. (1) of the preferred embodiment to the transition-count array. Mean time-lag values and average transition rates are likewise computed by applying Eqs. (2) and (3) of the preferred embodiment to the transition-count array.

4. Transition-flux information is computed as follows.

a. At the same time that the array described in Step 3.a is created, an additional five arrays with the same dimensions as it has, and having initial values of 0 in every element, also are created.

b. Every time the value of an element of the transition-count array is incremented, as described in Step 3.d, the corresponding elements of the arrays created in Step 4.a also have their values modified. The changes in the current array-element values are computed via Eq. (5) of the preferred embodiment.

c. After the entire array of Hb-state values is scanned, transition fluxes are computed by applying Eq. (6) of the preferred embodiment to the arrays created in Steps 3.a and 4.a.

5. After the entire array of Hb-state values is scanned (Step 3), transition masses are computed by applying Eq. (7) of the preferred embodiment to the arrays created in Steps 3.a and 4.a.

6. After the entire array of Hb-state values is scanned (Step 3), transition-rate-weighted transition fluxes and transition-rate-weighted transition masses are computed by applying Eqs. (8) and (9) of the preferred embodiment to the arrays created in Steps 3.a and 4.a.

Effects of the Invention:

Having the goal of appreciating abnormal or normal tissue states under a wide range of environmental situations and subject status conditions for which prior art uses of perturbation methods are likely to prove impractical or even harmful, and in recognition that the physiology of feedback mechanisms that sustain oxygen homeostasis in tissue can impart features that are not observable from application of feature extraction methods to the individual components of the Hb signal, the inventive methods described herein, which are favorably applied under a substantially resting state condition, serve to greatly expand the environments and subject status conditions wherein noninvasive Hb time-series of tissues can be acquired and from which a previously unrecognized dense feature space of coefficients can accessed from use of methods disclosed herein that apply understandings of Stochastic Network Theory and related capabilities described herein to the co-varying components of the Hb signal. As is documented by measures described in the Preferred Embodiment, and applied to a representative tissue class (breast) and representative disease type (cancer), derived coefficients have the character of substantial independence across a wide range of coefficient types whose amplitudes appear strongly sensitive to the presence of cancer.

Also, having recognized that disturbances in oxygen homeostasis affect a wide range of disease types as well as tissue responses to differing classes of stimulation imposed by external stimuli, drugs, and interaction with tissue implants, the methods described here are deemed to significantly facilitate assessment of these behaviors and in doing so can support the following capabilities:

1. Improved detection of breast cancer without the need for exposure to ionizing sources or painful breast compression. Prior art techniques are limited in one or more of the following: dependence of applied force or Valsalva maneuvers; reliance on static sensing methods that significantly reduce the range of features that could be determined; employment of methods that explore individual hemoglobin components from a time series measure, which also has the effect of limiting the range of features that can be identified by methods motivated from understandings of tumor features. Also, the demonstration that multiple substantially independent features are accessible makes it likely that extension of applied univariate statistical measures for disease detection will have improved performance when multivariate techniques that can include machine learning or deep learning methods are used for the evaluation.

These capabilities also make it likely that the disclosed methods can serve to improve assessment of treatment responses, for example, the effectiveness of neoadjuvant chemotherapy. These are facilitated by the ease and improved patient compliance that accompanies a resting state measure and from the expectation that positive responses to chemotherapy will modify oxygen homeostasis as a consequence of reducing tumor load.

Figure 3:
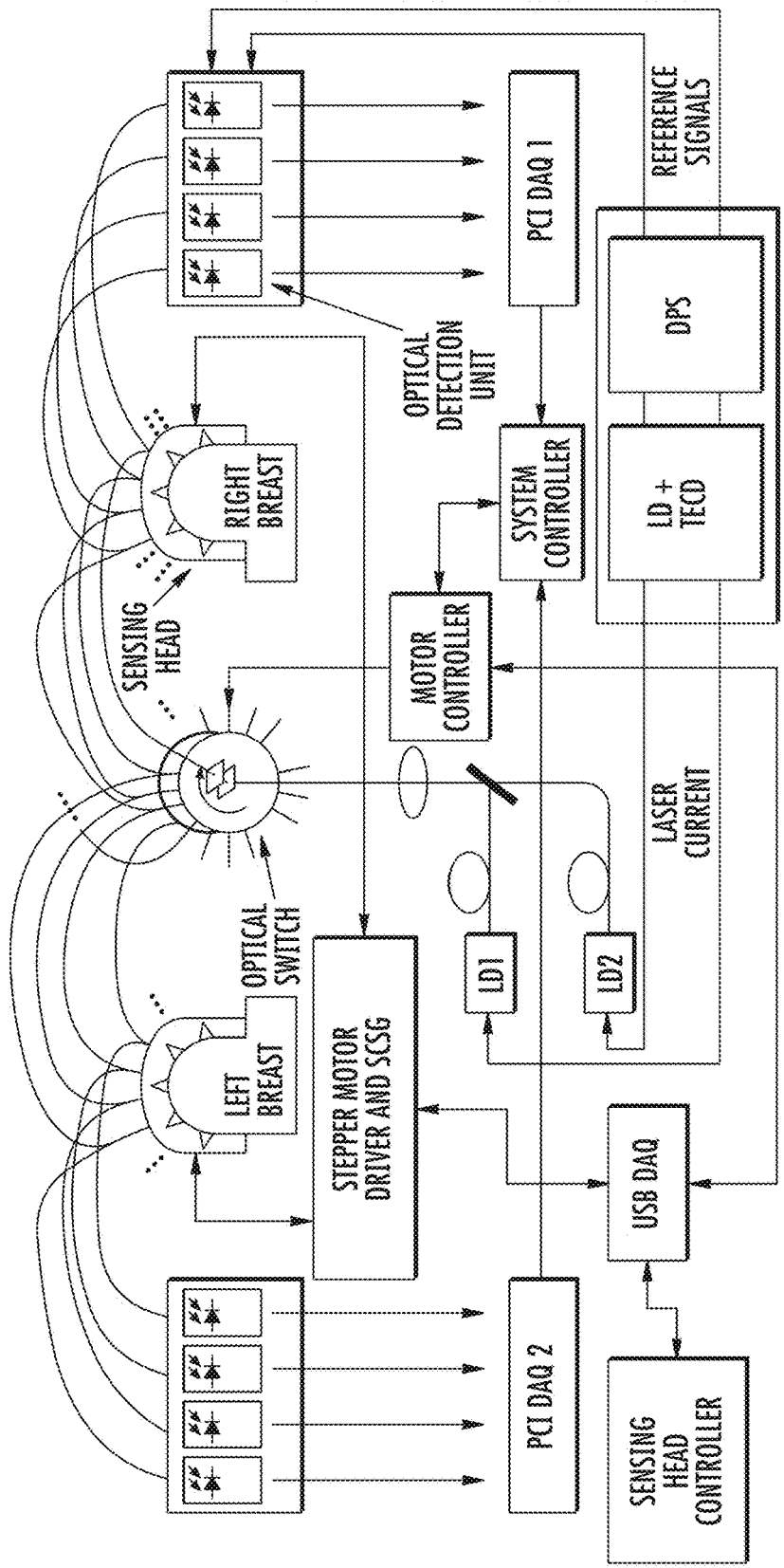
FIG. 3 is a block diagram of the breast imager as used in accordance with the invention. System operates by driving two sensing head simultaneously, each effecting a 32-source x 64-detector array per breast. DAQ=Data acquisition board, DPS=Digital Phase Shifter, LD=Laser diode, SGSC=Strain gauge semiconductor, TECD=Thermo-electric cooler driver.

It is further recognized that the mechanical support members shown in FIG. 3, employed as an investigative tool to acquire Hb time series measures from the breast, can be replaced by soft contact sensors positioned within a brassiere-like housing, which will likely further extend patient acceptance of optical sensing methods. Such formats, which can allow for measures while subjects are comfortably seated, also are deemed to improve patient compliance that likely facilitates more frequent screening, thereby enabling earlier disease detection.

2. Improved detection of other forms of cancer that are accessible within the limits of optical penetration. Included in this class are head and neck cancers, skin cancers including malignant melanomas, and tumors in tissues accessible from endoscopic formats. Because enhanced tumor angiogenesis is commonly seen in many forms of cancer, the methods and coefficient classes identified herein are expected to translate to these disease states as well.

3. Improved monitoring of wound-healing. Current methods, which can employ the techniques of hyperspectral imaging, NIRS, OCT, laser Doppler imaging, laser speckle imaging, spatial frequency domain imaging and digital camera imaging [M. Jayachandran et al., *Adv. Wound Care*] all share the common goal of producing information of individual features (e.g., individual Hb components, wound size and area, burn depth, burn scar perfusion, and collagen denaturation) and not from co-varying properties common to functional networks that modulate the bulk of physiological phenomena in living beings. The presence of an expected inflammatory response, reduced perfusion in affected regions and neovascuarization as a consequence of wound recovery, strongly indicate that the normal oxygen homeostasis supply-demands present in healthy, unaffected tissues should be strongly affected. As a consequence, we anticipate that several of the identified coefficient classes listed in the preferred embodiment will likely be affected. As each of these constitutes a dense array of mainly independent behaviors, the likely discriminatory power accessible from these measures as a basis for clinical guidance and characterization is significantly improved compared to existing assessments. Also recognized is that because several of the listed methods can be adapted to provide time-series measures of the Hb signal, it is expected that more than one class of system capabilities are likely to benefit from the inventive matter disclosed herein.

4. Improved monitoring of the progression, or of the response to therapeutic interventions, of chronic pathologies that have vascular manifestations. This class would include peripheral artery disease (PAD) and diabetic vasculopathy. The methods of the invention allow for greater ability to acquire relevant data with minimal disruption to subjects' activities of daily living.

5. Improved monitoring of the progression, or of the response to therapeutic interventions, of pathologies that produce skin ulcers or other dermatological lesions. This class includes the mentioned cases of PAD and diabetes, and also some cases of autoimmune diseases such as lupus and psoriasis. A related class of applications is detection of incipient bedsores, in individuals who are comatose or are conscious but bedridden.

6. The methods of the invention are potentially applicable for clinical or research environment in which the target population consists of or includes individuals who are unconscious or paralyzed. The latter category would include cases of temporary (e.g., because the subject is immobilized by a cast) as well as permanent (e.g., owing to spinal-cord injury) paralysis.

7. Recording of hemodynamic data, of the brain, peripheral tissue structures, or both, during sleep studies. These applications have the potential to yield improved insight into the physiological stresses induced by conditions such as sleep apnea, as well as the effectiveness of interventions such as positive airway pressure.

8. Earlier and more reliable detection of inflammatory states, in tissues lying within the limits of optical penetration, whether these states are of acute (e.g., bacterial infection, medication side effects) or chronic (e.g., incipient arthritis, autoimmune disease, arteriosclerosis) origin.

9. Improved ability to include infants and children and other vulnerable subject classes within the population of subjects that can be evaluated using NIRS-based technologies. These are individuals for who some perturbation-based strategies may be physically impossible (e.g., Valsalva maneuver for neonatal subjects), while others may be deemed to pose unacceptable risk or would be likely to meet with poor compliance (e.g., 12-hour fasting for pediatric subjects).

10. Improved ability to monitoring the mental status, or the peripheral-tissue oxygenation status, of people engaged in activities that involve relatively low levels of physical activity, although frequently over an extended time period, coupled with high levels of mental effort. Examples of applications in this area would include examining long-haul truck drivers, operators of commercial or military aircraft or ships or members of surgical teams (or airplane, ship, or submarine crews), for early indications of fatigue.

11. Better performance and extended range of capabilities, for brain-computer interface (BCI) applications. These are likely consequences of the invention making a set of previously unappreciated hemodynamic features available for analysis. Some or many of the latter may prove to correlate better, or more consistently or reliably, with subject intent than do the perturbation-based responses that are the current focus of most BCI effort. Alternatively, in recognition that the goal of BCI is to infer information on a relative short time scale, and in recognition that coordinated behaviors of the brain are not static, the considered measures may serve to identify which of several likely functional states is operational. It follows that applied training methods can be fine-tuned to recognize when these are present thereby improving the interpretation of individual subject responses.

12. For of the mentioned capabilities and those related as a consequence of their impacting oxygen homeostasis, it is also appreciated that the metrics outlined by Eqs. 1-3, 6-9, 12, 13, others listed in the section on Description of Alternative Embodiments and those described, but not expressly listed (e.g., measures of asymmetry), including the goal to determine various "hidden" coefficients that are normally accessible from solutions to inverse problems that follow from methods suitable to explore network problems and their associated rules (e.g., use of FLT), as well as features identified from findings listed in the included Figures, can be expressed to appreciate trends in these measures from repeat measures that, when compared to group-level measures of healthy subjects, or to themselves, can serve to indicate the presence of anomalous behaviors. It is also recognized that these trends can be acquired from wireless wearable devices equipped to perform time-series Hb measures that are linked to cloud computing environments. This arrangement can serve to identify if detected anomalous trends warrant immediate attention (e.g., call to emergency services) or additional follow-up.

Method of Implementing Preferred Embodiment

1. Relationships Among Co-Varying Elements of the Hb Signal

Covariation among state variables in a dynamical system can be appreciated by examining state-space plots. This may be accomplished in the case of Hb time series measures by plotting the time-varying changes in oxyHb against concurrent variations in deoxyHb (i.e., ΔoxyHb vs. ΔdeoxyHb). For simplicity, here we limit our attention to the quasi steady-state changes in component values relative to their respective temporal means.

We can additionally represent relative changes in the dependent Hb-signal components (i.e., totalHb, $HbO_2Sat$, $HbO_2Exc$) within the ΔHb state-space plot, by introducing associated axes whose orientations with respect to the primary axes follows directly from their definitions. Thus, concurrent changes in totalHb levels (i.e., ΔtotalHb) can be appreciated by introducing an axis rotated 45 degrees counterclockwise about the origin with respect to the ΔdeoxyHb axis. Appreciation of co-variations in $\Delta HbO_2Exc$ can be gained by introducing a fourth axis orthogonal to the ΔtotalHb axis. By adding a line demarcating (ΔdeoxyHb, ΔoxyHb) pairs that correspond to hemoglobin oxygen saturations above and below the temporal mean value, $\Delta HbO_2Sat$ values can also be determined from the plot.

The resulting co-varying coordinate system is depicted in FIG. 1 and Table 1. The regions of the plane corresponding to positive and negative changes relative to the temporal mean value for each signal component are indicated in FIG. 1, while Table 1 lists the specific permutations of algebraic signs present in each sector of the plane, leading to the assignment of ten distinct 'states'. [It can be shown that the correct inclination angle for the $\Delta HbO_2Sat$ demarcation line with respect to the ΔdeoxyHb axis is $\tan^{-1}(S/(100-S))$, where S is the temporal mean value (in percentage) of $HbO_2Sat$. The inclination angle depicted in FIG. 1 corresponds to S=85% [P. Taroni, G. Quarto, A. Pifferi, F. Abbate, N. Balestreri, S. Menna, E. Cassano, R. Cubeddu, "Breast tissue composition and its dependence on demographic risk factors for breast cancer: Non-invasive assessment by time domain diffuse optical spectroscopy," *PLoS ONE* 10, e0128941 (2015)]].] The identified coordinate system represents an extension of the 6-state co-varying system originally considered by our group [G. W. Wylie et al., *NeuroImage*; R. L. Barbour, Y. Pei, M. Farber, H. L. Graber, Y. Xu, and D. Sreedharan, "Functional imaging of autoregulation," Poster No. 219 M-AM at Human Brain Mapping 2007 (Chicago, Ill., Jun. 10-14, 2007). Available online at http://otg.downstate.edu/Publication/BarbourHBM0.7.pdf]. It also represents an extension of subsequent reports that recognized added information accessible from a co-varying representation of the hemoglobin components [K. Yoshino and T. Kato, *NeuroReport*; K.S. Hong and N. Naseer, *Int. J. Neur. Sys.*].

TABLE 1

Definitions of the ten co-variational states, in terms of the algebraic signs of the five Hb signal components in comparison to their respective temporal mean values.

| State | Algebraic sign of Component[a] o d t e s | Additional Constraints[b] |
|---|---|---|
| 1 | - - - - + | e: \|o\| < \|d\|<br>s: \|o\|/O < \|t\|/T |
| 2 | - - - + + | e: \|o\| > \|d\|<br>s: \|o\|/O < \|t\|/T |
| 3 | - - - + - | e: \|o\| > \|d\|<br>s: \|o\|/O > \|t\|/T |
| 4 | - + - + - | s: \|o\|/O > \|t\|/T<br>t: \|o\| > \|d\| |
| 5 | - + + + - | t: \|o\| < \|d\| |
| 6 | + + + + - | e: \|o\| < \|d\|<br>s: \|o\|/O < \|t\|/T |
| 7 | + + + - - | e: \|o\| > \|d\|<br>s: \|o\|/O < \|t\|/T |
| 8 | + + + - + | e: \|o\| > \|d\|<br>s: \|o\|/O > \|t\|/T |
| 9 | + - + - + | s: \|o\|/O > \|t\|/T<br>t: \|o\| > \|d\| |
| 10 | + - - - + | t: \|o\| < \|d\| |

[a]Upper-case letters denote the temporal mean mean value; lower-case letters denote differences with respect to the temporal mean value. 'O','o' = oxyHb; 'd' = deoxyHb; 'T','t' = totalHb; 'e' = $HbO_2Exc$; 's' = $HbO_2Sat$.
[b]In addition to the algebraic-sign constraints inherent in the state definitions: when 'd' and 'o' have the same sign, the sign of 'e' supplies a constraint; when 'd' and 'o' have opposite signs, the sign of 't' supplies a constraint; and, when 'o' and 't' have the same sign, the sign of 's' supplies a constraint.

2. Quantification of Inter-State Hb-Transition Coefficients

Every image voxel occupies exactly one of the ten Hb-states at each measurement time frame. Using v and t for the space and time variables, respectively, and Δt for the reciprocal of the data sampling rate, s(v,t) denotes the state of the $v^{th}$ voxel in the $t^{th}$ time frame and s(v,t+nΔt) is the state of the same voxel n time frames later. The approach we take counts only the direct transitions from one state into a different one, and excludes all instances of s(v,t)→s(v,t+nΔt) that have intervening transitions within the n-time-frame lag. Thus, we count all one-step transitions of a specified type, irrespective of the time interval over which those transitions occur. Also excluded is any consideration of distance from the origin of the (ΔdeoxyHb, ΔoxyHb) coordinate system, even though we recognize the possibility that, for example, the portion of the State-1 sector (FIG. 1) preferentially transitioned into could be a function of which of the other states was the predecessor. This postulated history dependence would distinguish the network dynamics from those of a true FMC.

a. Computation of State Transition Probability

At the start of a transition-probability computation, a 10×10×N array of integer variables, where N is the largest value of the time lag that will be considered, is initialized to all zeros. Each element of the three-dimensional array will accumulate a count of the number of transitions of a given type: position in the first dimension ("row") encodes the Hb-states that voxels transition into, in the second dimension ("column") the state that they transition from, and in the third dimension ("layer") the time lag for the transitions.

Starting with v=t=n=1, the values of s(v,t) and s(v,t+nΔt) are ascertained. If s(v,t+nΔt)≠s(v,t) the value in the [s(v,t+nΔt),s(v,t),n]$^{th}$ element of the accumulator array is increased by 1; otherwise, n is incremented until the inequality criterion is met. Each time the inequality criterion is met (thereby indicating that a transition to a different state has occurred), the current value of t is increased to t+nΔt (i.e., the previous post-transition time frame becomes the new pre-transition time frame), and the procedure described in the previous paragraph is repeated. The process of accumulating and incrementing t continues until the end of the time series is reached, at which point the value of v is incremented, t and n reset to 1, and the preceding sequence of operations is repeated until the maximum values of v and t are reached.

We use the symbol A to denote the accumulator array, and f (for "final state") and i ("initial state") for the row and column indices, respectively. For f≠i, (the f=i elements are superfluous in this analysis) the sum $\Sigma_{n=1}^{N} A_{fi}(n)$ is the total number of transitions directly from state i to state f, irrespective of the number of intervening time frames. The sum of accumulated values in every layer of the array is proportional to the subject-specific time-series duration and voxel count. Accordingly, to allow for computation of average transition matrices across subjects, we normalize the sum of transition counts to 100, including only the 90 f≠i elements in the normalization. Thus $$P_{fi} = \frac{100 \sum_{n=1}^{N} A_{fi}(n)}{\sum_{f=1}^{10} \sum_{i=1}^{10} (1-\delta_{fi}) \sum_{n=1}^{N} A_{fi}(n)}, \quad (1)$$

where $\delta_{fi}$ is the Kronecker delta.

b. Computation of State Transition Rate

The approach taken here also allows for extraction of a mean time-lag value for each transition type:

$$\tau_{fi} = \frac{\sum_{n=1}^{N} n \cdot A_{fi}(n)}{\sum_{n=1}^{N} A_{fi}(n)}, \quad (2)$$

For f≠i, the computed $\tau_{fi}$ value is the average number of time frames associated with transitions from state i into state f The mean time can be transformed to an equivalent rate constant for i→f transitions (f≠i case) where $$k_{fi} = \frac{1}{\tau_{fi}}. \quad (3)$$

In Eq. (3), $k_{fi}$ has nominal units of (time frame)$^{-1}$ which is easily converted to seconds$^{-1}$ by multiplying by the data sampling rate.

3. Quantification of Transition-Linked Hemoglobin-Concentration and -Saturation Changes A small modification to the accumulation scheme allows us to determine the average amounts by which levels of the five components of the Hb signal change during each of the $$90 \to f(f \neq i)$$

transition types. In place of the single previously considered accumulator array, we now define six such arrays, $$A_{TC}, A_D, A_E, A_O, A_S, A_T, \quad (1)$$

each having the dimensionality and size as the accumulator considered in the preceding section and each initialized to all-zeros, and where the subscripts denote: TC =transition count, D =ΔdeoxyHb, E =ΔHbO$_2$Exc, O =ΔoxyHb, S =ΔHbO$_2$Sat, T =ΔtotalHb. For each transition, values stored in appropriate elements of the accumulators are incremented as follows:

$A_{TC}$(s(v,t +nΔt),s(v,t),n)→$A_{TC}$(s(v,t +nΔt),s(v,t),n)+ 1, $A_D$(s(v,t+nΔt),s(v,t),n)→$A_D$(s(v,t+nΔt),s(v,t), n) +deoxyHb(v,t+nΔt)−deoxyHb(v,t), $A_E$(s(v,t+ nΔt),s(v,t),n)→$A_E$(s(v,t+nΔt),s(v,t),n) +HbO$_2$Eff (v,t +nΔt)−HbO$_2$Eff(v,t), +oxyHb(v,t+nΔt)− oxyHb(v,t), $A_s$(s(v,t +nΔt),s(v,t),n)→$A_s$(s(v,t+ nΔt),s(v,t),n) +HbO$_2$Sat(v,t+nΔt)−HbO$_2$Sat(v,t), $A_T$(s(v,t+nΔt),s(v,t),n)→$A_T$(s(v,t+nΔt),s(v,t), n) +totalHb(v,t +nΔt)−totalHb(v, t).

$A_{TC}$(s(v,t +nΔt),s(v,t),n)→$A_{TC}$(s(v,t+nΔt),s(v,t), n)+1, $A_D$(s(v,t +nΔt),s(v,t),n)→$A_D$(s(v,t+nΔt),s (v,t),n) +deoxyHb(v,t +nΔt)−deoxyHb(v,t), $A_E$(s (v,t +nΔt),s(v,t),n)→$A_{E(s(v,t+nΔt),s(v,t),n)}$ +HbO2Exc (v,t+nΔt)−HbO$_2$Exc(v,t), $A_O$(s(v,t+Δt), s(v,t),n)→$A_O$(s(v,t +nΔt),s(v,t),n) +oxyHb(v,t+ nΔt )−oxyHb(v,t), $A_S$(s(v,t+nΔt ),s(v,t),n)→$A_S$(s (v,t+nΔt),s(v,t),n) +HbO$_2$Sat(v,t+nΔt )−HbO$_2$Sat (v,t), $A_T$(s(v,t+nΔt),s(v,t),n)→$A_T$(s(v,t+nΔt),s(v, t),n) +totalHb(v,t+nΔt)−totalHb(v,t) (5)

a. Transition "flux" Computation

The transition flux for a given hemodynamic-signal component is equal to the average change in concentration or saturation, per transition of a specified type. Mathematically, the flux for transitions from state i to state f is equal to $$\phi_X(f, i) = \frac{\sum_{n=1}^{N} A_X(f, i, n)}{\sum_{n=1}^{N} A_{TC}(f, i, n)}, \quad (6)$$

where the generic symbol X is used to denote any of the five hemoglobin-signal components D, E, O, S or T.

b. Computation of Weighted Transition Fluxes

Inspection of the coefficient array maps for $P_{fi}$, $k_{fi}$ and $\phi_X$(f,i) reveal qualitative differences among their dependences on the transition type (i.e., on which Hb-states correspond to f and i in Eqs. (1), (3) and (6)). This suggests the possibility that additional information (e.g., greater discriminatory power between healthy and diseased tissues) might be obtained by considering two-parameter products. Thus, combinations that includes a transition flux (φ) as one of the factors can be conceptualized as a 'weighted flux', with the remaining factor (k or P) constituting the weighting term.

The $P_{fi}\phi_X$(f,i) product for a given hemodynamic-signal component is a quantity that we call the transition "mass"

[$m_X(f,i)$] and is equal to the average concentration or saturation change that actually occurs during the time required for a set number of transitions to happen. Proceeding from Eqs. (1) and (6), we see that the mass for transitions from state i to state f for signal component X, is $$m_X(f, i) = P_{fi}\phi_X(f, i) = \frac{100\sum_{n=1}^{N} A_{TC}(f, i, n)}{\sum_{f=1}^{10}\sum_{i=1}^{10}(1 - \delta_{fi})\sum_{n=1}^{N} A_{TC}(f, i, n)} \cdot \frac{\sum_{n=1}^{N} A_X(f, i, n)}{\sum_{n=1}^{N} A_{TC}(f, i, n)} \quad (7)$$

$$= 100\frac{\sum_{n=1}^{N} A_X(f, i, n)}{\sum_{f=1}^{10}\sum_{i=1}^{10}(1 - \delta_{fi})\sum_{n=1}^{N} A_{TC}(f, i, n)}.$$

The quantity $m_X(f,i)$ defined in Eq. (7) can be conceptualized as the average quantity of material that is transferred from State i to State f whenever 100 transitions overall (i.e., including all types) occur. Multiplying either $\phi_X(f,i)$ or $m_X(f,i)$ by $k_{fi}$ produces a quantity in which the concentration or saturation changes are given per unit time rather than on a per-transition basis. The corresponding mathematical formulations are $$k_{fi}\phi_X(f, i) = \frac{\sum_{n=1}^{N} A_{TC}(f, i, n)}{\sum_{n=1}^{N} n \cdot A_{TC}(f, i, n)} \cdot \frac{\sum_{n=1}^{N} A_X(f, i, n)}{\sum_{n=1}^{N} A_{TC}(f, i, n)} = \frac{\sum_{n=1}^{N} A_X(f, i, n)}{\sum_{n=1}^{N} n \cdot A_{TC}(f, i, n)} \quad (8)$$

and $$k_{fi}m_X(f, i) = \quad (9)$$

$$100\frac{\sum_{n=1}^{N} A_{TC}(f, i, n)}{\sum_{n=1}^{N} n \cdot A_{TC}(f, i, n)} \cdot \frac{\sum_{n=1}^{N} A_X(f, i, n)}{\sum_{f=1}^{10}\sum_{i=1}^{10}(1 - \delta_{fi})\sum_{n=1}^{N} A_{TC}(f, i, n)}.$$

To distinguish the influence of this rescaling process, going forward we refer to unweight coefficients [i.e., Eq. (6)] as intrinsic coefficient values, while those listed in Eqs. (7)-(9) are called weighted coefficient values.

4. Influence of Algebraic Sign of Hb-Component on Transition Flux Amplitude.

In Eq. (5), the increments for all of the A arrays except $A_{TC}$ are defined as a difference between the concentration or saturation values at two identified time frames. From the way the Hb-states are defined (see FIG. 1, Table 1), it follows that for each component of the Hb signal some transition types produce only positive increments, others only negative ones, and others a mixture of positive and negative increments. This mixture produces different feature characteristics whose interpretation is aided by the following understandings.

Figure 2:
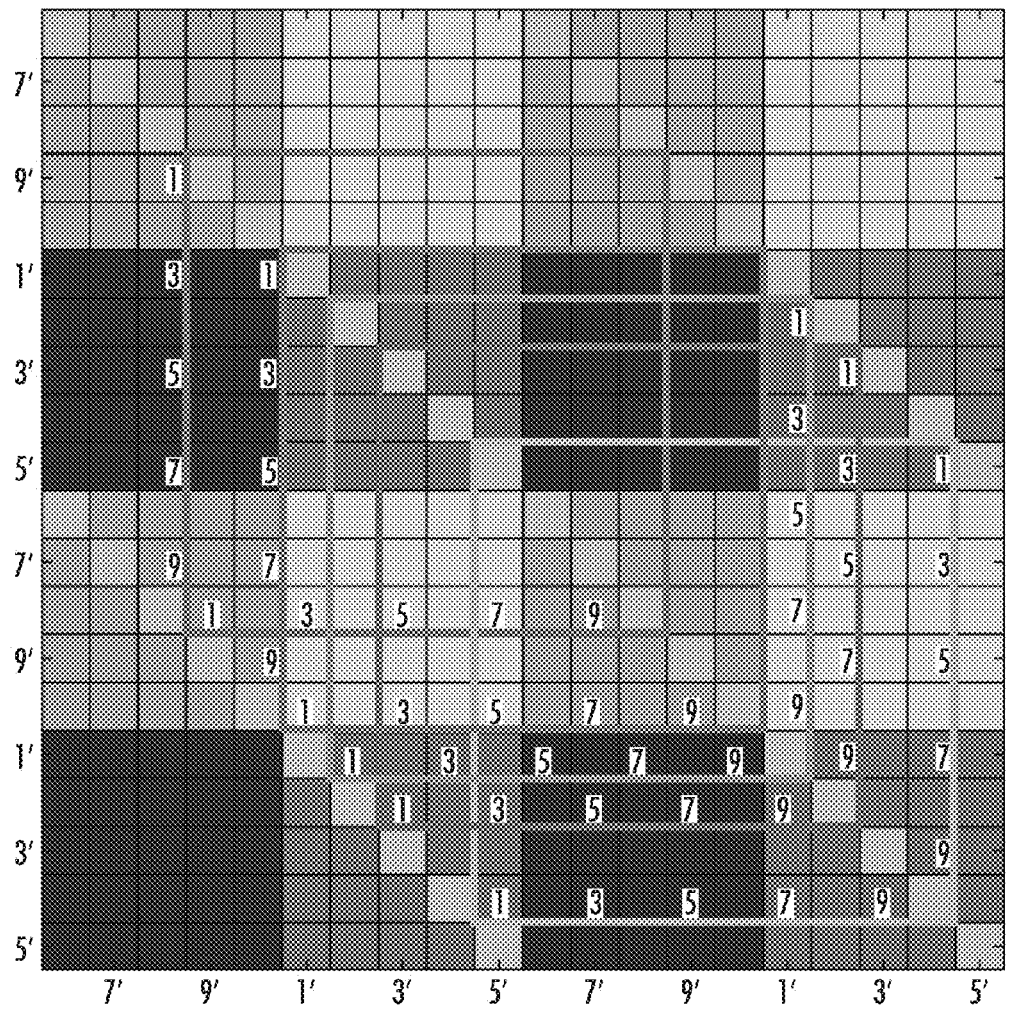
FIG. 2 is a graphical representation of the identification of the relation between algebraic signs of pre- and post-transition ΔHb values, for each component of the Hb signal, in accordance with the invention. Numbering along figure edges reflects the periodicity of the Hb-state sequence (see FIG. 1). Numbers along edges of colored bounding boxes indicate the pre- and post-transition states (along the horizontal and vertical axes, respectively), for each component: red=ΔoxyHb ('o'), blue=ΔdeoxyHb ('d'), green=ΔtotalHb ('t'), cyan=$ΔHbO_2Exc$ ('e'), magenta=$ΔHbO_2Sat$ ('s'). Solid-block colors indicate: cyan=(−)→(−) transitions, blue=(+)→(−), olive=(+)→(+), yellow=(−)→(+).

The algebraic signs associated with different transition types are coded as colored regions in FIG. 2. The navy-blue color indicates transitions from a positive (i.e., greater than the temporal mean value) to a negative value, in which case the concentration or saturation must decrease; while yellow indicates transitions from negative to positive values, so that concentration or saturation must increase. The light-blue color corresponds to transitions from one negative value to another, in which case the Hb-component value will increase in some transitions and decrease in others; and the same is true for the olive-colored regions, which correspond to transitions from one positive value to another. The color-coded boundary squares in FIG. 2 show which portions of the checkerboard pattern correspond to the algebraic-sign distributions for each Hb component. Note that the region inside each colored boundary square has the same row and column assignments. Thus, the cell in the upper right corner of each bounded square corresponds to State 10→1 transitions. As is shown in Results, there are features in the associated coefficient-flux maps that are spatially correlated with those in FIG. 2.

Separate from these feature characteristics, it is helpful to appreciate the influence that changes in state-dependent flux amplitudes for the various Hb components will have on the appearance of transition-parameter maps. For instance, transitions that must entail a change in algebraic sign will identify the net amplitude of the concentration or saturation change, but not the magnitude of the hemoglobin signal relative to its temporal mean value. In contrast, transitions in which the algebraic sign does not change will produce net values that constitute the sum of cancelations. As a result, these values may be either positive or negative, and the observed algebraic sign will indicate whether the pre- or post-transition value is farther from the temporal mean.

While the mathematical treatments described in previous sections do not require assignment of any given sequence to the defined state numbering system, we nevertheless have arranged these to reflect a gradient of successively greater degrees of metabolic demand in relation to blood supply with vascular compensation. Depicting extreme examples of this response are the transitions between states 5 and 10 and between 3 and 8. For instance, the 10→5 transition identifies a hyperemic response, but one that is insufficient to meet demand, causing the levels of $\Delta oxyHb$ and $\Delta HbO_2Sat$ to fall below their temporal mean values while the levels of $\Delta HbO_2Eff$ and $\Delta deoxyHb$ rise. Conversely, the 3→8 transition principally reflects a similar response, but one that more than meets metabolic demand, causing $\Delta HbO_2Sat$ and $\Delta HbO_2Exc$ values to fall while $\Delta oxyHb$, $\Delta deoxyHb$ and $\Delta totalHb$ levels rise. The associated reciprocal transitions reflect responses in compensation from hyperemia. As noted, not specifically reflected in this representation are explicit sensitivities of these parameters to changes in blood flow separate from variations in tissue metabolic oxygen demand [S. Fantini, NeuroImage].

Exemplary Data for the Preferred Embodiment

Here we report group-average findings obtained from subject groups, comprising women who are and are not affected with unilateral breast cancer, that identify the coefficient types defined above. To assist comprehension of these data, we begin by describing subject-preparation and data-collection and-processing methods used, although these are not essential parts of the invention.

1. Diffuse Optical Tomography: Optical time series measures of the breast were acquired using a custom-made, high density tomography system [R. Al abdi et al. JOSA-A], shown in FIG. 3. Notable capabilities of this unit include the capacity to examine both breasts simultaneously while, if desired, exposing the breast to concurrent defined viscoelastic deformations. Illumination was achieved by employing a dual-wavelength laser source (760, 830 nm) that is time-multiplexed to allow for simultaneous recording of light intensities from all elements of the sensing array. In all, each sensing head contains 64 dual-wavelength sources and 32 detector elements that are evenly divided within a two-stage arrangement.

2. Subject Preparation: System operation supports examination of the breast while the subject is comfortably seated. Having a hinged arrangement, the top portion of the sensing array can be adjusted to allow for controlled contact in an anatomically conforming manner. In all, sensing elements are arranged to support essentially a full circumferential measurement. Prior to enrollment, inform consent was obtained from all subjects in accordance with SUNY IRB #99-093. In all, data from 63 subjects were explored, 18 with confirmed breast cancer (6-right breast, 12-left breast, average tumor size ~2.7 cm, range 0.5-6 cm) and 45 non-cancer subjects, 23 of whom had evidence of various types of non-malignant pathologies in either breast. A more detailed description of enrolled subjects is given in [H. L. Graber et al., *Medical Physics*]. It deserves mention that findings reported here involve the same subject groups as in [H. L. Graber et al., *Medical Physics*] and exploration of the same data. Different are the methodologies applied for data analysis.

3. Data Collection: Following initial setup, automated system calibration was performed to identify optimal gain settings. Subsequently, resting-state measures were acquired for a period lasting ~5-10 minutes.

4. Data Preprocessing: Data were screened for evidence of degradation of signal quality caused by excessive signal attenuation by very large breasts or by poor skin-contact for very small breasts, using methods previously described [H. L. Graber et al., *Medical Physics*]. To avoid introducing bilateral signal bias, channels excluded from one breast were also excluded from the other, resulting in symmetric data sets. Also, to avoid biases from undersampling, only measures from women that included at least 60% of all data channels were considered. Experience showed that operating limits are breasts having cup sizes varying from B to DD.

5. 3D Image Reconstruction: Tomographic reconstructions were achieved by first normalizing measured signal intensities to the respective temporal mean values of each data channel, then solving a system of linear equations using a modified perturbation formulation based on solutions to the diffusion equation [H. L. Graber, Y. Pei, and R. L. Barbour, "Imaging of spatiotemporal coincident states by DC optical tomography," *IEEE Transactions on Medical Imaging* 21, 852-866 (2002); Y. Pei, H. L. Graber, and R. L. Barbour, "Influence of systematic errors in reference states on image quality and on stability of derived information for DC optical imaging," *Applied Optics* 40, 5755-5769 (2001)]. Computed wavelength-dependent absorption coefficient values were subsequently transformed to yield spatial maps of the time-varying components of the hemoglobin signal. This produced five sets of maps for each breast, corresponding to spatiotemporal variations in the independent and dependent Hb components.

Figure 4A:
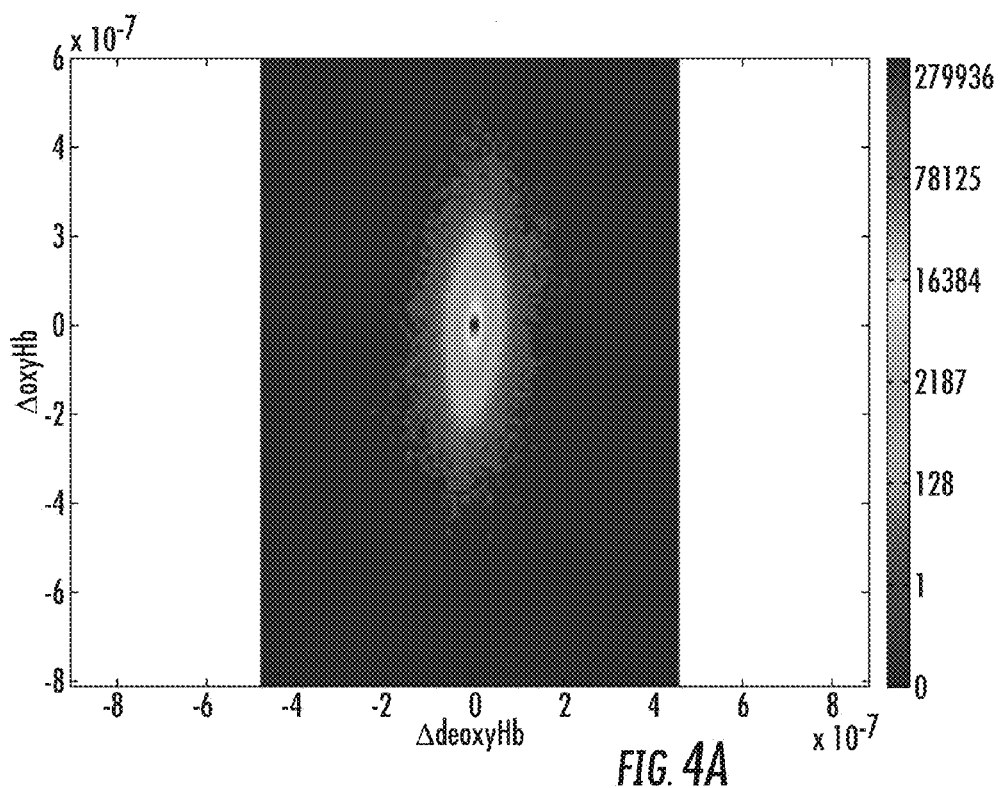
FIGS. 4(a) and 4(b) are plots of temporally coincident resting-state ΔoxyHb and ΔdeoxyHb ('o' and 'd') values obtained from time-series tomographic image values, for FIG. 4(a) unaffected and 4(b) cancerous breasts of a representative clinical-study subject, respectively, in accordance with the invention.
Figure 4B:
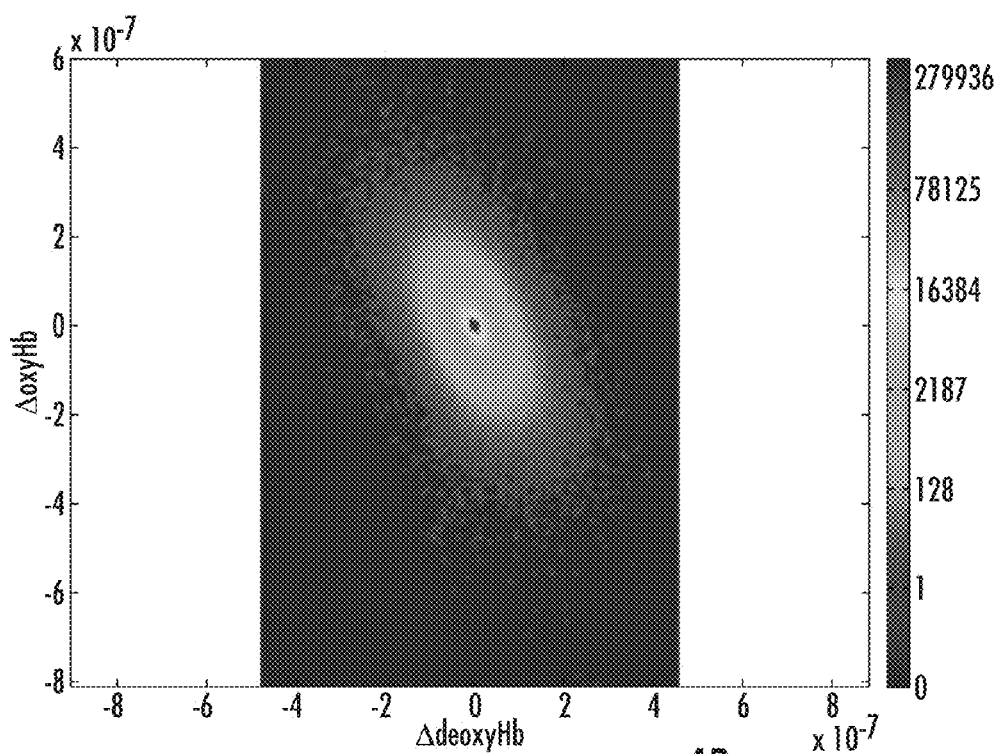

In FIG. 4 we plot representative measures acquired from an affected and unaffected breast, of a woman in the breast-cancer subject group, represented in the FIG. 1 coordinate system. Inspection reveals a cloud of points, with the frequency of occurrence of each paired ΔdeoxyHb, ΔoxyHb combination indicated by the color scale. Inspection also reveals distinct ellipsoidal distributions whose details strongly suggests sensitivity to the presence of disease. While the overall patterns seen might suggest ways to quantify the shape of the distribution, our focus is instead directed to the expectation that temporal variability in the actions of the feedback mechanisms will serve to drive Hb-component values from one functional state to another. Accordingly, our attention is directed to quantifying features associated with such transitions.

6. Evaluation of diagnostic potential of transition-associated parameters: Here we use the generic symbol $Y_{fi}$ to denote any of the transition-related quantities—$P_{fi}$, $k_{fi}$, $\phi_X(f,i)$, $m_X(f,i)$, or the related products $k_{fi}\phi_X(f,i)$, $k_{fi}m_X(f,i)$—that are subsequently evaluated as diagnostic indicators for breast cancer. For any transition type, each study subject has distinct values of $Y_{fi}$ for the left and right breast (i.e., $Y_{fi}^l$ and $Y_{fi}^r$, respectively). To minimize contributions to inter-subject variability by factors unrelated to the presence of disease, we consider the relative percent differences between $Y_{fi}^l$ and $Y_{fi}^r$ as diagnostic-metric candidates.

In view of the demonstrational nature of the diagnostic-potential computations reported here, and the small number of subjects in the breast-cancer group (N=18), we do not consider multiple-category or multiple-factor analyses such as would be appropriate for a large clinical trial. Instead, data for all breast-cancer subjects are combined to form one group. Because the 18 subjects with cancer comprise 12 with a tumor of the left breast and 6 who have it in the right, combining them necessitates performing an adjustment to minimize confounding of tumor effects with any intrinsic left-right asymmetries that may be present. Accordingly, the diagnostic metrics are generated in the following manner. For subjects known to have left-breast tumors (and for subjects in the non-cancer group):

$$Z_{fi}(j) = 100 \frac{Y_{fi}^l(j) - Y_{fi}^r(j)}{y_{fi}^r(j)}, \qquad (10)$$

where j is the subject index. For subjects known to have right-breast tumors, $$Z_{fi}(j) = 100 \frac{[Y_{fi}^r(j) - \overline{Y_{fi}^r}_{NC} + \overline{Y_{fi}^l}_{NC}] - [Y_{fi}^l(j) - \overline{Y_{fi}^l}_{NC} + \overline{Y_{fi}^r}_{NC}]}{Y_{fi}^l(j) - \overline{Y_{fi}^l}_{NC} + \overline{Y_{fi}^r}_{NC}}, \qquad (11)$$

where $\overline{Y_{fi}^l}_{NC}$ and $\overline{Y_{fi}^r}_{NC}$ denote quantities averaged over all subjects in the non-cancer group. The linear adjustment operations in Eq. (11) have the effect of correcting the difference between parameter values in the tumor-bearing and unaffected breasts for left-right biases that are not related to the presence of disease. As such, they are based on a plausible assumption that, to first order, the net inter-breast difference is the linear sum of background-asymmetry and tumor-related contributions, and that the magnitude of the former is not itself strongly disease-dependent.

For each combination of transition-related parameter and transition type, the sets of $Z_{fi}$ values for breast-cancer and non-cancer subjects were the input to a receiver operator characteristic (ROC) analysis [H. L. Graber et al., *Medical Physics*], with the area-under-curve (AUC) parameter taken as our index of overall diagnostic accuracy [C. E. Metz, "Basic principles of ROC analysis," *Semin. Nucl. Med.* 8, 283-298 (1978)].

7. Organization of Exemplary Data: These are divided into two sections: findings from analysis of State-transitions and those from Hb-dependent component transitions. Finally, we report selected findings from ROC analysis, which support the conclusion that the derived coefficients may serve as useful markers for disease.

8. Hb State-Transition Coefficients a. Coefficient Maps of State Transition Rate Values FIG. 5 shows the group-mean values of the rate constants for inter-state transitions [Eq. (3)] for women with breast cancer. Each square cell's column assignment identifies the Hb-state that is transitioned from while the row assignment denotes the state that is transitioned to. FIG. 5(a) shows the rate-constant values obtained from tumor-bearing breasts (T), 5(b) the difference in values between affected and unaffected (U) breasts (T-U) and 5(c) p-values obtained from Student t-tests comparing the 5(b) data to the corresponding inter-breast differences (left-minus-right (L-R)) for the subjects without breast cancer (i.e., unpaired tests comparing L-R vs. T-U). As indicated by the color contrast, FIG. 5(a) shows that transition rate constants for affected breasts vary over a range of ~1.20-1.75 second$^{-1}$, depending on the transition pair. Closer examination reveals that the rate constants are preferentially elevated for transitions originating from States 3 and 8, and preferentially suppressed for those originating from States 4 and 9. Also seen is the apparent absence of an equivalent bias involving transitions into a given state (i.e., row features), indicating that rate constants involving reciprocal pairs of transitions are asymmetric.

A more careful inspection of FIG. 5(a) reveals a distinct influence of the presence or absence of hyperemia on transition rate constants. The largest values are transitions from State 3 into States 5-9, and from State 8 into States 10 and 1-4. Common to these state transitions is a change in the level of ΔtotalHb, suggesting sensitivity to hyperemia. Different from this are transitions from States 4 and 9. Here we find that those which do not involve an associated hyperemia (i.e., from State 4 into States 10 and 1-4, and from State 9 into States 5-8), have the smallest rate constant values overall.

Shown in FIG. 5(b) are the differences between rate constant values for affected and unaffected breasts. Inspection reveals coefficient values that are preferentially elevated by the presence of disease and others that are suppressed. Among the former, and most evident, are all transitions from States 2 and 7 into the others. Transition rates that are reduced in affected breasts principally include those originating from States 5 and 10. In FIG. 5(c), which identifies the transitions for which the inter-breast rate-constant difference is significantly different between the two subject groups, we see that group differences are mainly clustered among transitions from States 1-3 and from States 6-8.

Taken together, these findings reveal two principal disease-dependent contrast features. First is the finding of elevated overall transition rates in affected breasts. We interpret that as consistent with the general observation that metabolic rates in a tumor bearing breast are also elevated. Second, this behavior appears preferentially biased towards specific classes of transitions, in a manner suggestive of a compensatory response. In support of the latter is the finding that whereas transitions from States 3 and 8 have the largest values for either T or U breasts, the impact of disease appears greatest on either side of these transitions (i.e., largest positive and negative bias for transitions from States 2 and 7 and from 5 and 10, respectively). We also recognize that because measures were obtained under substantially steady-state conditions, a bias in one direction requires an opposing bias to not disturb the temporal mean value. However, given the many degrees of freedom associated with a ten-state model, it would seem evident that there are multiple ways that such a balance could be achieved, suggesting that a 'salt-and-pepper' pattern might be preferred in the absence of specific driving factors. The finding of distinctive patterns suggests that the disease-dependent influences are present.

The transition-rate patterns for the L, R and U breast groupings are not explicitly shown, owing to space limitations and to their qualitative similarity to FIG. 5(a). As an alternative, in Table 2 below, we have computed two quantitative indices of dissimilarity and have applied these to highlight group-level differences among the overall amplitudes and patterns of the measured coefficients. The first is a normalized root mean squared difference (nRMSD; a value of 0 indicates exact equality) between the coefficient amplitudes in the transition rate-constant maps (excluding the main diagonal), comparing either T and U or various pairings of unaffected breasts (i.e., L and R, L and U, R and U). The second is a measure of the spatial correlation of patterns observed between the rate-constant maps for the same pairings. To obtain a quantitative measure of the overall impact of breast cancer on rate constants, we have compared the mean value of the nRMSD and correlation for the three control group pairings (i.e., L and R, L and U, R and U) to the corresponding indices for T-U, in both cases using the t-score as a convenient indicator of group difference. This is intended to aid interpretation by presenting the contrast between tumor-unaffected and unaffected-unaffected values in terms of a familiar dimensionless unit, and not for the purpose of statistical testing.

TABLE 2

Normalized root mean squared difference (nRMSD) and Pearson correlation coefficient, between transition-parameter data for different subject-breast pairings. Exact equality would produce nRMSD = 0 and correlation = 1. nRMSD is defined as: nRMSD(α, β) = $\sqrt{\Sigma(\alpha-\beta)^2}/[(\sqrt{\Sigma\alpha^2} + \sqrt{\Sigma\beta^2})/2]$, where 'α' and 'β' are the sets of 90 coefficient values in the (main-diagonal-excluded) 10 × 10 maps for two selected subject-breast groups.

| Dissimilarity Index | Transition Parameter | x: T, U | y: mean(L, R; L, U; R, U) | z: SD(L, R; L, U; R, U) | (x − y)/z[a] |
|---|---|---|---|---|---|
| nRMSD | k | 0.063 | 0.029 | 0.012 | 2.81 |
|  | P | 0.630 | 0.264 | 0.123 | 2.96 |
|  | φ | 0.479-0.710 | 0.187-0.316 | 0.098-0.148 | 2.61-2.96 |
|  | m | 0.778-0.924 | 0.343-0.438 | 0.166-0.210 | 2.28-2.62 |

TABLE 2-continued

Normalized root mean squared difference (nRMSD) and Pearson correlation coefficient, between transition-parameter data for different subject-breast pairings. Exact equality would produce nRMSD = 0 and correlation = 1. nRMSD is defined as: nRMSD($\alpha$, $\beta$) = $\sqrt{\Sigma(\alpha-\beta)^2/[(\sqrt{\Sigma\alpha^2} + \sqrt{\Sigma\beta^2})/2]}$, where '$\alpha$' and '$\beta$' are the sets of 90 coefficient values in the (main-diagonal-excluded) 10 × 10 maps for two selected subject-breast groups.

| Dissimilarity Index | Transition Parameter | x: T, U | y: mean(L, R; L, U; R, U) | z: SD(L, R; L, U; R, U) | (x − y)/z[a] |
|---|---|---|---|---|---|
| Correlation | k | 0.853 | 0.965 | 0.026 | −4.27 |
|  | P | 0.897 | 0.978 | 0.018 | −4.46 |
|  | φ | 0.988-0.996 | 0.997-0.999 | 0.00086-0.0028 | −2.78--5.81 |
|  | m | 0.952-0.975 | 0.983-0.993 | 0.0050-0.012 | −2.61--4.29 |

[a]This dimensionless index is the t-score of the nRMSD or correlation value for the T, U pairing, in comparison to the mean and standard deviation of all the pairings of non-tumor breasts.

The correlation values obtained for measures of k are r=0.853 for the T-U comparison, and r=0.965 for the mean of the control pairings (SD=0.026). While the former is notably reduced compared to the latter, indicating disease sensitivity, the amplitude patterns of transition rates over all state pairings among the breasts in either subject group is, nevertheless, strongly correlated. This is not overly surprising as in these instances the tabulated values are derived from data that was concurrently acquired from both breasts of the same subjects. Consequently, it is noteworthy that the L-U and R-U comparisons, involving data for two separate groups of subjects, also yield higher correlations than does the T-U case. The same pattern of results was found in the nRMSD values, which is larger (i.e., farther from zero, indicating less similarity) for the T-U case than for any of the control pairings, whether these involved comparisons of data from the same subjects (L-R) or from two distinct subject groups (L-U and R-U). The t-score values for nRMSD and correlation are 2.81 and −4.27, respectively, indicating that the impact of breast tumors is several times larger than the other sources of variance.

b. Coefficient Maps of State Transition Probability Values

Shown in FIG. 6 are findings having the same format as identified in FIG. 5, but for measures of State transition probability [Eq. (1)]. A brief comparison of these to the corresponding parameter maps in FIG. 5 reveals that the transition-probability and transition rate-constant patterns seen are weakly correlated and hence substantially independent. This finding is not surprising, as the prevalence and rate of change of behavior are independent in many systems. While many feature particulars are present, here we limit our consideration to only a few.

Most striking is evidence of substantial symmetry among reciprocal pairs of transitions, over a larger range of values than is observed for the transition rate constants. Regions having the lowest probabilities correspond to transitions to and from States 1-3 and 6-8. Also seen is evidence of biases in the probabilities of transitions between Hb-states. For example, transitions either to or from States 3 and 8 are uniformly less probable than those involving adjacent states on either side (2 and 4, 7 and 9), producing a striped appearance. Having significantly higher, but also less uniform, probabilities are transitions to or from States 4, 5 and 9, 10. The net result of these biases is to produce a transition probability map that bears some similarity to the pattern of algebraic signs for transition-associated changes in $\Delta$deoxyHb concentration depicted in FIG. 2. More specifically, it is seen that those transitions having the largest and smallest amplitudes mainly coincide with the regions that undergo a change in their algebraic sign of $\Delta$deoxyHb (yellow and navy-blue regions of FIG. 2).

Figures 6A, 6B, 6C:
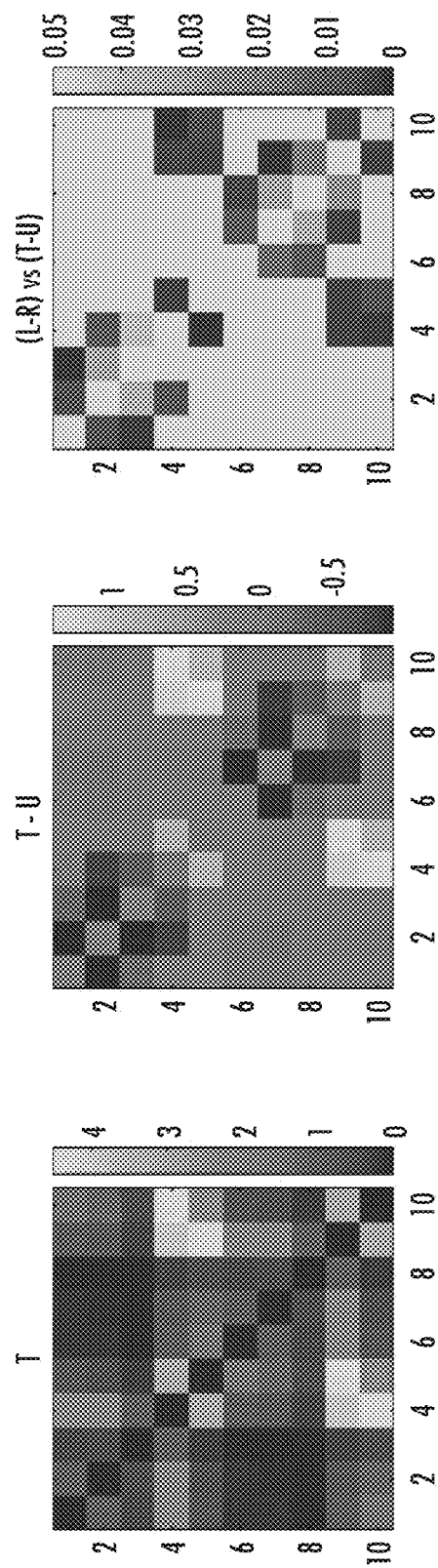
FIGS. 6(a), 6(b), and 6(c) are graphical representations of transition probabilities (units are percent), for subjects with unilateral breast cancer; computed using Eq. (1), in accordance with the invention.

Similar to the difference between State-transition rate constants for affected and unaffected breasts (FIG. 5(b)), results in FIG. 6(b) shows that the probabilities of particular transitions can be either elevated or reduced in the T breast in comparison to U. One interesting difference between the rate and probability T-U maps is that the pattern of the latter appears clustered about three groups of transitions. Having reduced amplitudes are transitions involving State 2 with either 1 or 3 and those involving State 7 with either 6 or 8, while those having elevated amplitudes involve the transition between either State 4 or 5 and either 9 or 10, as well as directly between 4 and 5 or 9 and 10.

Included in Table 2 are values for the two inter-group similarity metrics described in the preceding section, computed for the transition-probability maps. The overall trends in these findings are similar to those for the rate constant measures. That only modest reductions in these quantities are observed for either k or P is not surprising, given that the average partial volume of tumor in affected breasts is on the order of 3% or less. Even so, the T-U nRMSD is appreciably larger than the mean value for the unaffected-breast pairings (t=2.96 (P) and 2.81 (k)), and the correlation substantially lower (t=−4.46 (P) and −4.27 (k)) for both types of coefficients.

While these findings indicate that the presence of disease does not grossly distort the mentioned coefficient values, evidence obtained from group difference measures for the T-U pairings (FIGS. 5(b) and 6(b)) does reveal distinct biases in coefficient values among selected transition types. Notable here is the evidence the response to disease on the amplitude of selected values of k are substantially independent of its corresponding impact on P.

Figure 7:
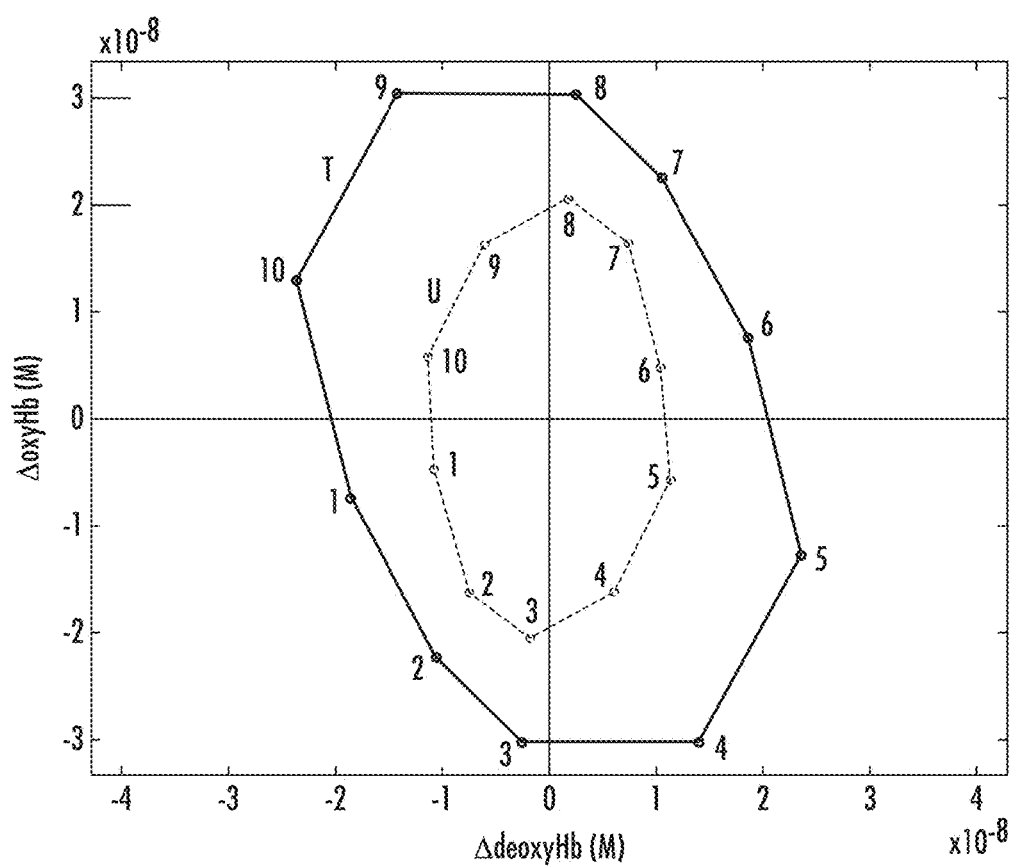
FIG. 7 is a plot of Concentration of ΔoxyHb vs. ΔdeoxyHb concentration, in each of the ten Hb-states, averaged across all time frames in each subject's volumetric image time series and across all subjects in the breast-cancer group. T=tumor-bearing breast; U=contralateral, unaffected breast, in accordance with the invention.

Figure 6(c) identifies those transitions for which the inter-breast probability difference is significant (p <0.05) between the subject groups, using the same criterion applied in FIG. 5(c). Inspection reveals that features that are significant are also those that mainly have the largest group-amplitude difference.

c. Hb-State Amplitude and Partial Volume Values i. Hb-State Mean Amplitude Values Additional state-dependent quantities that can be accessed via the applied methodology are measures of the mean Hb-component values for a given state, for the different subject groups. An example of these finding is shown in FIG. 7, where the group-mean $\Delta$oxyHb and $\Delta$deoxyHb values are plotted, for the affected (red) and unaffected (blue) breasts of affected women. Most evident is the shape of the distributions (mainly elliptical) and the obvious difference in their amplitudes. The latter being greater for affected breasts is consistent with general finding of enhanced angiogenesis in tumors [P. Vaupel, "Tumor blood flow," in *Blood Perfusion and Microenviron-* ment of Human Tumors: Implications for Clinical Radioon-cology*, edited by M. Molls and P. Vaupel (Springer, Berlin, 2000), pp. 41-45]. Also, as noted, the elongated trend in the direction close to that of the HbO$_2$Exc axis for affected breasts indicates a disease bias that reflects the known degraded ability of the vasculature of tumors to maintain supply-demand balanced by modulating blood volume to match changes in tissue oxygen consumption [P. Vaupel and M. Hockel, "Oxygenation of Human Tumors," in *Blood Perfusion and Microenvironment of Human Tumors: Implications for Clinical Radiooncology*, edited by M. Molls and P. Vaupel (Springer, Berlin, 2000), pp. 63-72]. This trend is also consistent with the general finding of a greater degree of desaturation of Hb in tumors [P. Vaupel and M. Hockel].

Figure 8B:
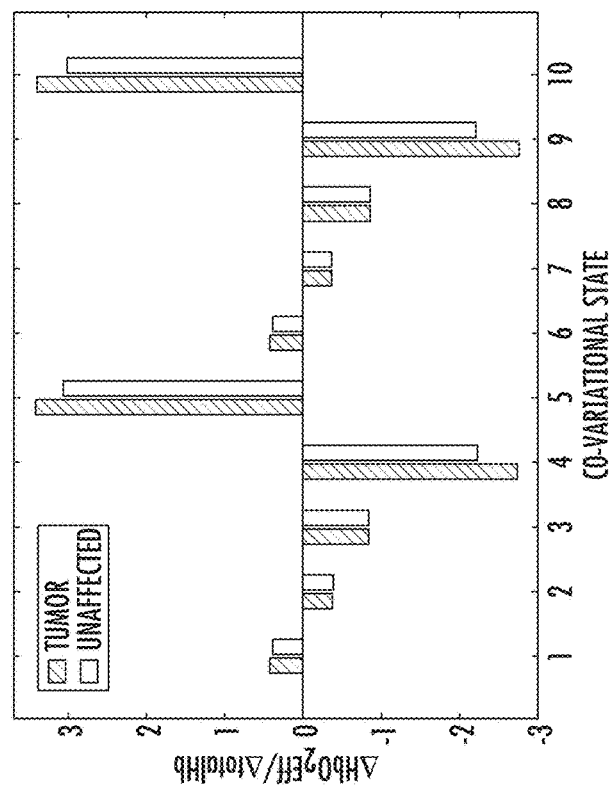
FIGS. 8(a) and 8(b) are Replots of group-mean ΔoxyHb vs. ΔdeoxyHb data (see FIG. 7) for the T and U breasts of the subjects with breast cancer, in accordance with the invention.
Figure 8A:
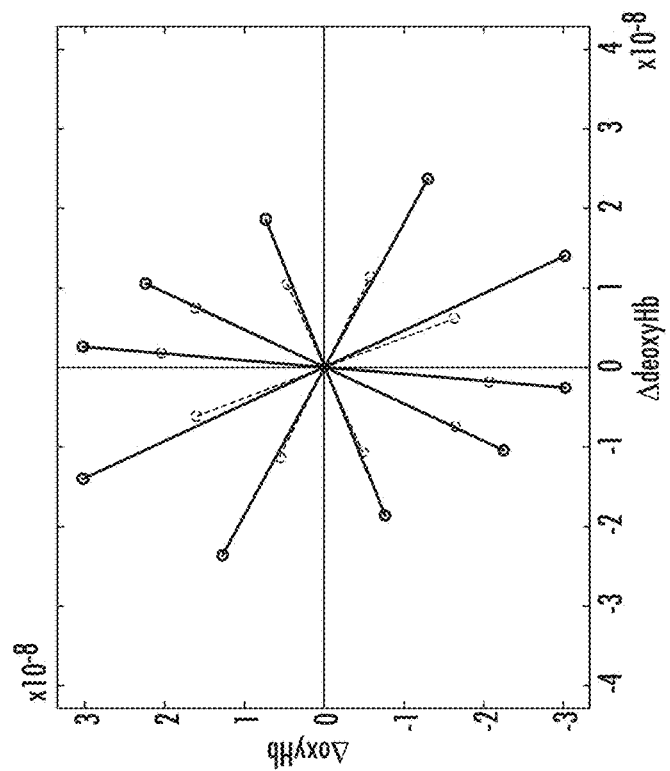

A more quantitative examination of the phenomena revealed by the FIG. 7 plot is presented in FIG. 8 Here we begin [FIG. 8(*a*)] by replotting the FIG. 7 data points but, instead of connecting adjacent points with line segments to emphasize the elliptical patterns, we add line segments connecting each data point to the origin of the coordinate system. In this way, a property not obvious by inspection of FIG. 7 is revealed: the angles between the red and blue line segments are close to zero for States 2, 3 ,7 and 8, larger for States 1, 5, 6 and 10, and largest of all for States 4 and 9.

To evaluate this trend, we have investigated the values of the plotted points' other Hb-signal components (i.e., their projections onto the other axes shown in FIG. 1). The most informative result, plotted in FIG. 8(*b*), is obtained by computing the ratio of ΔHbO$_2$Exc to ΔtotalHb for each of the states (as previously noted, these are the components that are the most directly affected by the presence of a tumor: modulation of ΔtotalHb occurs to a proportionally greater extent in the unaffected breast, and of ΔHbO$_2$Exc in the affected one). It is seen that for every state that has an angle discrepancy noticeable by inspection in FIG. 8(*a*) (i.e., States 1, 4, 5, 6, 9 and 10), the absolute value of the ratio is larger for the tumor breast, which is to say that the magnitude of ΔtotalHb "response" relative to the magnitude of ΔHbO$_2$Exc "stimulus" is smaller in the affected than in the unaffected breast (p <1×10$^{-4}$, for all listed states [paired t-tests]). This finding is fully consistent with the known behavior that tumors have a reduced capacity to regulate their blood supply to match changes in ambient oxygen demand [P. Vaupel]. We find it noteworthy that this effect is largest for States 4 and 9, which most closely agree with the condition wherein supply is less(more) than adequate to meet demand, so that ΔoxyHb, ΔtotalHb and ΔHbO$_2$Sat all have the same algebraic sign, and ΔdeoxyHb and ΔHbO$_2$Exc have the opposite sign. Consequently, these states are the ones in which reduced capability of tumor-breast vasculature to match changes in blood supply to changes in oxygen demand would be most apparent, which is what we observe.

ii. Hb-State Partial Volume Values

Figure 9:
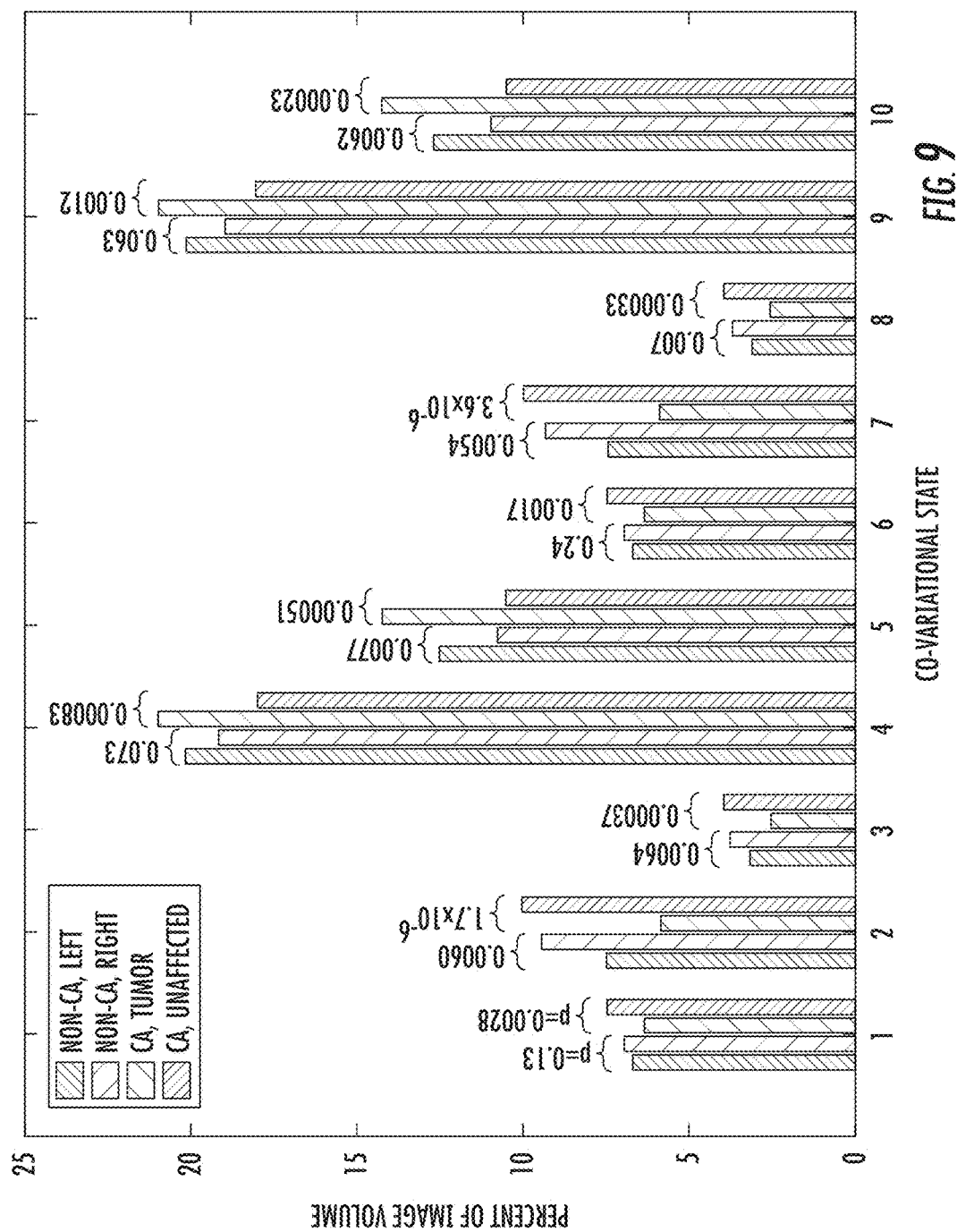
FIG. 9 is a graph depicting percentage of image volume in each of the ten Hb-states, averaged across all time frames in each subject's volumetric image time series and across all subjects in the indicated groups. Annotations are t-test p-values for comparisons of mean values for the left (L) and right (R) breasts (non-cancer subjects) and of the tumor (T) and unaffected (U) breasts (breast-cancer subjects), in accordance with the invention.

A simple measure of state dependence is the time-average volume fraction of tissue that is occupied by a given state. This can be determined by simply counting the number of image voxels that exist in one state or another and expressing these quantities as the relative fraction (percentage) of the total volume, averaged over time. FIG. 9 shows the ten states' volume fractions (in units of percent) for the different groupings of study subject and breast-cancer status. Here we have separately plotted group-mean values for the L and R breasts of control subjects (N=45), and for the T and U breasts of affected subjects (N=18). Inspection reveals that the volume fraction for States 1-3 and 6-8 are reduced in T, and increased in States 4, 5 and 9, 10. We also note that while there is evidence of an intrinsic left-right bias in unaffected subjects, the p-values associated with this trend are consistently higher (i.e., lower statistical significance) than the findings obtained from corresponding inter-breast comparison for the affected subjects, even though the latter group contains less than half the number of subjects. We also note the diverse composition of the control group, which includes women who have no history of any breast pathology (N=22) and a similar number of aged-matched subjects who have a variety of documented breast pathologies other than overt malignancy. This suggests that the observed bias exhibits disease specificity.

Separate from appreciation of the feature space of the volume fraction measures is a more quantitative understanding of relationships between these measures and the previously described State transition parameters (i.e., transition rates and probability). For instance, comparing the FIG. 9 volume-fraction distribution to the pattern of transition probabilities in FIG. 6 reveals that trends in the former appear to determine some of the features of the latter; e.g., that the lowest probability is found for transitions from/to States 3 and 8, and the largest is seen for transitions from/to States 4 and 9. However, there also are features of FIG. 6 that would not be easily predicted from inspection of FIG. 9, such as the greater probability for transitions between 4 and 10 or between 5 and 9 than for ones directly between 4 and 9. It is worth considering what may be the form of the function that transforms the 2D probability map into the 1D volume fractions, and how consistent it is across the four subject-breast pairings.

The simplest assumption is direct proportionality between transition probability and volume fraction, with the rate constants serving also as the constants of proportionality. Thus, the volume fraction for State j would be equal to $$V_j = K \sum_{i=1}^{10} \frac{P_{ij}}{k_{ij}}, \quad K \equiv \frac{100}{\sum_{j=1}^{10} \sum_{i=1}^{10} \frac{P_{ij}}{k_{ij}}}, \quad (12)$$

where the normalization constant K ensures that the quantity on the right-hand side of Eq. (12) is equal to 100 when summed over all j (as is the sum of the V$_j$s, by definition). It is found (not shown) that there is excellent agreement between the true and computed volume fractions (i.e., left- and right-hand sides of Eq. (12), with a mean relative percent discrepancy $$\left(\text{i.e., } 100\left(V_j - K\sum_{i=1}^{10} \frac{P_{ij}}{k_{ij}}\right) \middle/ V_j\right),$$

of just over 1% across the four subject-breast groups. This finding of consistency across data sets demonstrates the stability of the data transformations used to derive the state-transition coefficients.

In addition, the observed accuracy of the Eq. (12) model shows that transitions between Hb-states are first-order processes, as kinetics of any other order would lead to a different mathematical relationship among k, P and V. In view of the mathematical relationship between rate constant and mean lifetime [Eq. (3)], the 1/k$_{ij}$ factor in Eq. (12) can be replaced by τ$_{ij}$, which leads to a compact formula relating the volume fractions of all states to the transition-probability and mean-lifetime coefficients:

$$V = K \cdot \text{diag}(P^T \tau) \qquad (13)$$

where K is the same as in Eq. (12), diag(X) is a vector consisting of the main-diagonal elements of the matrix X, and $P_{ij}$ and $\tau_{ij}$ are the $ij^{th}$ elements of P and $\tau$, respectively.

These relationships noted, nevertheless the added dimensions of transition rate and probability spaces relative to the volume fraction provides an opportunity to appreciate other disease-dependent biases. Of interest is the noted substantial independence of disease impact on specific features of these transition spaces (e.g., different particular transitions are most strongly affected in the k and P results). We contrast this finding with our previous report that explored the same imaging data and demonstrated a prominent temporal feature from affected breasts that is consistent with the existence of a persistent inflammatory response in tumors in response to upregulation of nitric oxide formation [H. L. Graber et al., *Medical Physics*]. While the data treatment strategy pursued here does not support independent assessment of behaviors originating from the tissue and vascular spaces, it is difficult to reconcile the evidence of differential influences on the State spaces on the sole basis of known effects of nitric oxide on the vascular space. We interpret this behavior as consistent with the known added actions that nitric oxide has on the tissue space (e.g., nitric oxide is a known competitive inhibitor of oxygen binding to cytochrome c-oxidase [P. Sarti, E. Forte, D. Mastronicola, A. Giuffrè, and M. Arese, "Cytochrome c oxidase and nitric oxide in action: Molecular mechanisms and pathophysiological implications," *Biochimica et Biophysica Acta—Bioenergetics* 1817, 610-619 (2012)]), combined with expected compensatory effects.

To briefly summarize, in this section we have identified the principal parameters accessible from measures of the Hb State-transitions. Comprising 2D spaces are the transition rate and probability coefficients, whose details appear mainly independent of each other and also appear disease-sensitive in a manner consistent with the several prominent cancer phenotypes. An additional finding is evidence of good feature recovery (i.e., computed volume fraction) from first order behavior in the kinetics of the rate-weighted transition probabilities.

Figure 10:
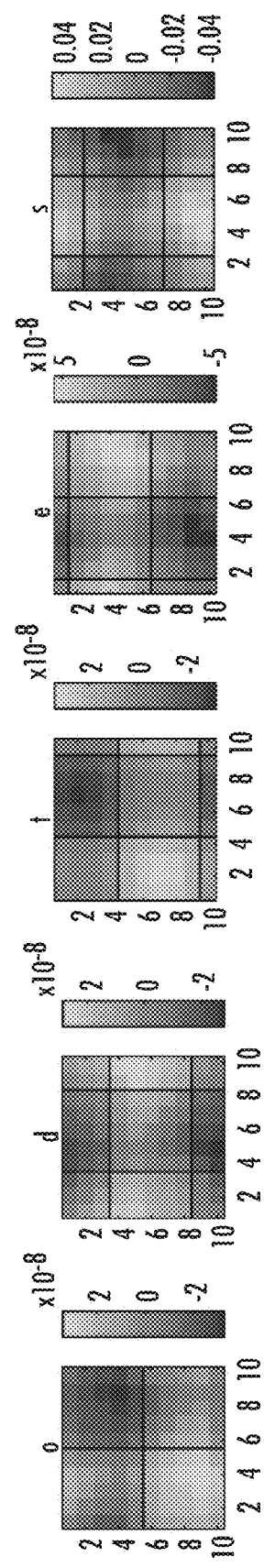
FIG. 10 is a series of graphs depicting intrinsic transition flux [i.e., average change, per transition, in concentration (units are moles-L$^{-1}$) or saturation (units are %); computed using Eq. (6)] results for the control-group subjects. Graphed data are averages over the left and right breasts. Letters 'o', 'd', 't', 'e', 's' denote the Hb components as indicated in Table 1. Thin solid lines separate regions according to the algebraic signs of the pre-and post-transition Hb-component values (see FIG. 2), in accordance with the invention.

2. Hb-Component Transition Coefficients a. Coefficient Maps of Hb-Component Flux Amplitude Values Shown in FIG. 10 are the state-dependent amplitudes of intrinsic transition flux [Eq. (6)] for the different components of the hemoglobin signal, computed from image time series of the breasts of control subjects (N=45). These quantities correspond to the average difference between the transition-dependent component values in the initial time frames of pre- and post-transition time intervals. Note that the scale for $\Delta HbO_2Sat$ is expressed as change in relative percent, while the values for the other components are molar quantities. Also, recall that these quantities are computed on a per-transition basis and not over a defined time interval, and that the plotted quantities are obtained by averaging over the full volume of the breast, the 5-10 minute period of observation and all control-group subjects. Inspection of the figure reveals several prominent features.

One feature clearly present is the tendency of the amplitude changes to appear spatially correlated with the component-dependent algebraic sign pattern that accompany given transition types (see FIG. 2). This is especially evident for the $\Delta$totalHb component. While application of a simple differencing scheme can be expected to produce a pattern whose deviation from the temporal mean is sensitive to the pattern of algebraic signs corresponding to specific state transitions, this is not sufficient to guarantee a smoothly varying pattern for any given component.

The counter consideration is one where the amplitudes within a specified sector [e.g., all transitions in which the algebraic sign of the component amplitude change from positive to negative (i.e., navy blue regions in FIG. 2)], would be mainly independent of the amplitudes of neighboring transition types, thus producing a "salt-and-pepper" appearance. This outcome would have important consequences for our postulated relationships between a sequence of state transitions and their sensitivity to intrinsic biological factors. As noted, the numbering sequence we have assigned to the state reflects a belief that passing through them in order traces out the compensatory hyperemic response to a hypothetical supply-demand imbalance. Thus, transitions between adjacent states (e.g., transition 2→3) are expected to reflect a more reduced state of imbalance than are transitions involving reciprocals (e.g., transition 1→6). It follows that if the transition-flux pattern were to have more of the conjectured salt-and-pepper appearance, it would suggest that either the assigned sequence of state transitions does not reflect the stated interpretation, or that our findings are strongly biased by unanticipated driving factors. Conversely, we interpret the smoothly varying patterns that were obtained as evidence that the assigned state transition sequence does roughly coincide with expected gradients in supply-demand imbalance. We further note that this understanding also holds in cases where measures of flux are alternatively expressed on fixed-time basis ($sec^{-1}$), which is a finding that expectedly follows from appreciation that the amplitude range for transition rates (FIG. 5) is many-fold smaller than that seen for intrinsic flux (FIG. 10).

Before proceeding, however, for completeness we provide a quantitative summary of comparisons between the intrinsic-flux measures for different pairings of breast and subject group, similar to those already considered for the rate constant and transition probability findings. Data in flux-related nRMSD and correlation rows of Table 2 indicate that while gross trends across all parameter transitions are highly correlated among the different groups, the range of intrinsic-flux correlations for Hb components is notably lower for the T-U pairing than for any of the others, and the nRMSD is notably larger.

Returning to FIG. 10, a more granular examination of the contrast features reveals that while amplitudes do smoothly vary, there also is evidence that different components of the hemoglobin signal exhibit preferred transition types.

To gain a better understanding as to the factors that might serve to facilitate these preferences, we have made separate examinations of the amplitudes of each component during the pre-transition and post-transition time frames, for measures obtained from control subjects. These results are shown in FIG. 11.

Figure 11A:
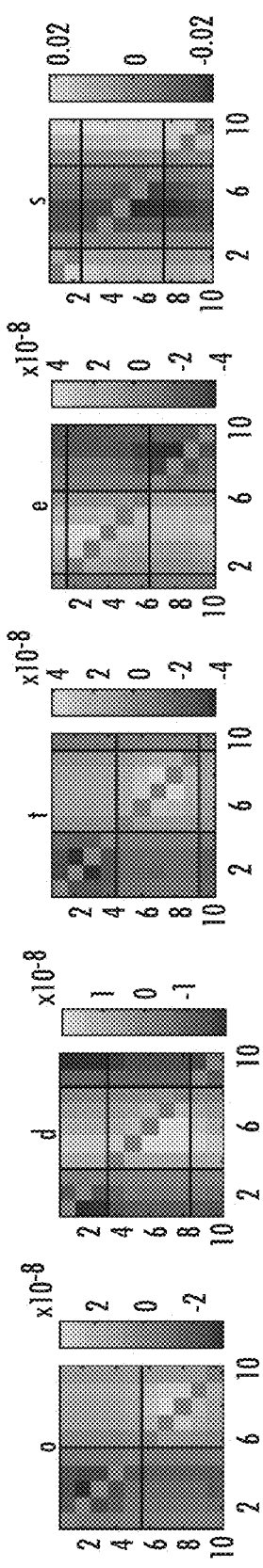
FIGS. 11(a) and 11(b) are two series of graphs depicting, in FIG. 11(a), average ΔHb amplitude in the pre-transition State encoded by the column index, given that the transition that ultimately occurs is to the State encoded by the row index; and, in FIG. 11(b), average ΔHb amplitude in the post-transition State encoded by the row index, given that the transition that ultimately occurs is from the State encoded by the column index. Letters 'o', 'd', 'e', 's' denote the Hb components as indicated in Table 1; units are percent for 's' and moles-L$^{-1}$ for all others. Thin solid lines separate regions according to the algebraic signs of the pre-and post-transition Hb-component values (see FIG. 2), in accordance with the invention.
Figure 11B:
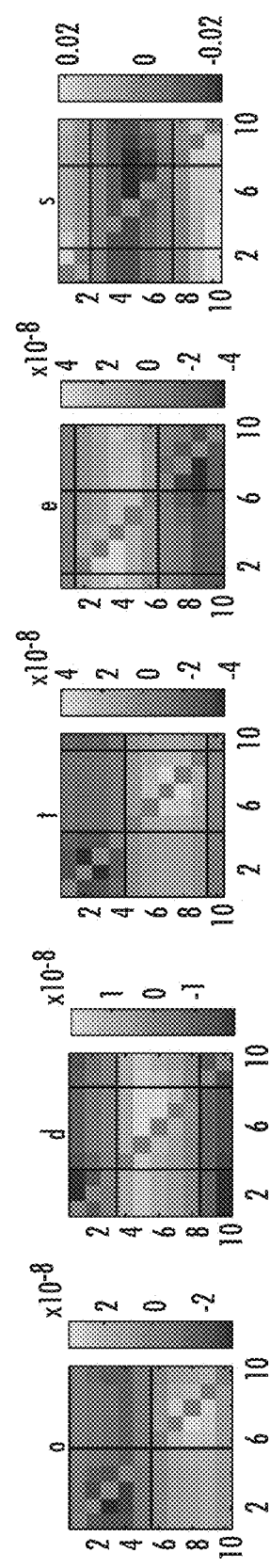

Plotted in FIG. 11(a) is the average amplitude, relative to the temporal mean, of the concentration or saturation at the beginning of the pre-transition time interval, while FIG. 11(b) shows the corresponding values at the start of the post-transition interval. Inspection reveals two prominent features. First, the pattern of amplitudes differs for the different components. Also evident is that, while the corresponding pre- and post-transition state amplitude maps appear mainly as conjugate pairs (i.e., each is nearly the transpose of the other), there is a notable relationship between regions in the coefficient maps having the greatest deviation from the mean, and the associated flux amplitude identified in FIG. 10. In particular, we observe that features in the former category are, in every instance, roughly spatially correlated with regions in the latter that have reduced flux amplitudes.

The noted relationship between fluxes and the pre- and post-transition amplitudes invites a comparison to a body of well-established theory on factors influencing thermodynamics and kinetics of chemical reactions, and, in particular, the influence of enzymatic transformations. For instance, reactions that have low potential energy barriers tend to occur more often than those with higher barriers. It follows that the patterns of high and low flux regions seen in FIG. 10 exist because the pre- and post-transition amplitudes are proportional to "intrinsic energy barriers" that serve to produce these patterns. We present this interpretation in the context of an analogy, with the understanding that the true mechanism is likely complex and dependent on a host of factors that may or may not explicitly depend on the suggested mechanism. Continuing with the chemical reaction analogy, the relation considered here (between intrinsic fluxes and the pre- and post-transition concentrations) calls to mind yet another phenomenon relevant to chemical reactions, the property of mass action.

Figure 12:
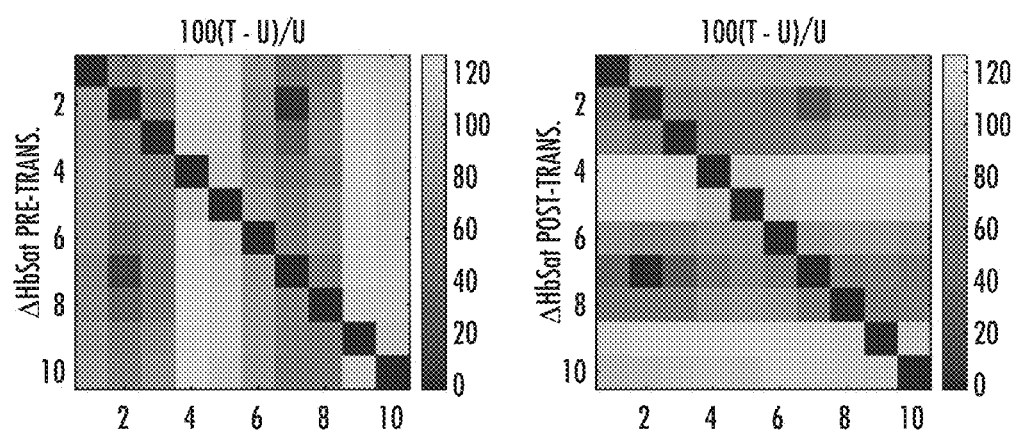
FIG. 12 is a pair of graphical representations depicting relative percent difference (dimensionless) between the (left) pre-transition and (right) post-transition ΔHbO$_2$Sat amplitudes, comparing the tumor-bearing and unaffected breasts of subjects in the breast-cancer group, in accordance with the invention.

The Law of Mass Action states that the rate of a chemical reaction is directly proportional to the product of the concentrations (activity) of its reactants. Extension of this understanding to the current study suggests that the observed rates of transition flux are in some way proportional to the amplitude patterns shown in FIG. 11. This hypothesis can be evaluated by regressing the intrinsic transition flux against the corresponding change in average amplitude (i.e., concentration or saturation) between the pre-transition and post-transition states. These results are in shown in Table 3 below. Inspection shows that these quantities are strongly correlated, but differ in their slopes (ranges for the corresponding intercepts are $10^{-6}$–$10^{-5}$ for $\Delta HbO_2Sat$ and $10^{-12}$–$10^{-10}$ for the others, and in no case, is the intercept significantly different from zero).

indicates a disease bias. The observation that the $\Delta HbO_2Sat$ intrinsic flux is most sensitive to the gradient (i.e., slope is closest to unity) suggests that changes in blood oxygenation are favored over changes in blood volume to achieve steady-state supply-demand balance.

b. Influence of Disease on the Distribution of Pre- and Post-Transition Component Amplitudes To gain additional understanding of the observed disease bias on what appears as a mass action effect, we have computed the inter-breast relative differences in both the pre- and post-transition component amplitudes, and have compared these relative differences across subject groups. The full comparison generates two parameter maps (one for the pre- and one for the post-transition amplitudes) for each component and subject group, and for brevity we limit our presentation of findings to only the $\Delta HbO_2Sat$ component. These results are shown in FIG. 12. Inspection reveals several prominent findings.

The pattern of features in FIG. 12 differs qualitatively from those seen in any of the other feature maps. At the grossest level of inspection, we find that each of the identified parameter spaces [(i.e., State transition rate constants (FIG. 5) and probabilities (FIG. 6), intrinsic flux (FIG. 10), pre- and post-transition component amplitudes (FIG. 11) and its associated sensitivity to disease (FIG. 12)] appear mainly independent of each other, especially at the level of individual State-component transitions. This finding is striking and strongly suggests that the composite of intrinsic driving factors that serve to maintain steady-state supply-demand balance in tissue exhibits differential sensitivity to each of the elements of the hemoglobin signal. However, the fact that three of these components, namely $\Delta HbO_2Sat$, $\Delta totalHb$ and $\Delta HbO_2Exc$, are not independent of the amplitudes of $\Delta deoxyHb$ and $\Delta oxyHb$, suggests a degree of fine tuning that, while grossly evident from the understanding that modulation of blood delivery to tissue is continuous, has nevertheless been difficult to quantify in the context of specifically observable parameters.

TABLE 3

Linear regression parameters obtained from fitting values for intrinsic flux to the average differences between the $\Delta Hb$ levels in the pre-transition and post-transition states, for each Hb component.

| | | Intrinsic flux vs. Average concentration (or saturation) difference | | | | | | |
|---|---|---|---|---|---|---|---|---|
| | | L | R | T | U | x: mean(L, R, U) | y: std(L, R, U) | (T − x)/y |
| correlation | e | 0.969 | 0.969 | 0.981 | 0.968 | 0.968 | 0.00065 | 19.5 |
| | d | 0.965 | 0.966 | 0.977 | 0.970 | 0.967 | 0.0028 | 3.5 |
| | t | 0.994 | 0.994 | 0.996 | 0.993 | 0.994 | 0.00070 | 3.9 |
| | s | 0.980 | 0.981 | 0.986 | 0.983 | 0.981 | 0.0016 | 3.02 |
| | o | 0.953 | 0.959 | 0.965 | 0.965 | 0.959 | 0.0063 | 1.03 |
| slope | e | 0.86 | 0.84 | 0.92 | 0.82 | 0.84 | 0.022 | 3.7 |
| | d | 0.85 | 0.83 | 0.90 | 0.83 | 0.84 | 0.011 | 5.3 |
| | t | 0.54 | 0.54 | 0.60 | 0.56 | 0.55 | 0.014 | 4.1 |
| | s | 0.93 | 0.91 | 0.95 | 0.91 | 0.91 | 0.010 | 3.9 |
| | o | 0.65 | 0.64 | 0.73 | 0.63 | 0.64 | 0.0086 | 10.9 |

The existence of a linear dependence identifies that the factor driving flux rates is a first-order process. Nevertheless, as noted, because the applied methodology does not distinguish behaviors among the principal tissue spaces, it seems likely that the identified order is an amalgam of more complex behaviors that actually do occur in these spaces. While this trend is seen in both subject groups, the finding of elevated slope values across all components of the hemoglobin signal for the affected breast of the cancer group Returning to the details of the parameter maps in FIG. 12, inspection reveals additional features that warrant comment. In the results for the breast-cancer subjects, we observe that transitions to and from States 4, 5 and 9, 10 are most affected and are the ones exhibiting the largest inter-breast relative difference. This shows that the pre- and post-transition amplitudes of these quantities have the greatest sensitivity to the presence of disease. Having the lowest disease sensitivity are transitions between States 2 and 7. Not shown are grossly similar findings involving patterns seen for the other Hb components. Thus we find instances where the response to disease varies from a more general influence on a class of transitions to one where the absence of influence is mainly limited to a single type of transition.

c. Hb-Flux Coefficient Trends Among Hb-Components:

Whereas the above findings serve to identify a relative independence of responses across the different feature spaces for individual Hb components or States, the high dimensionality makes it is difficult to appreciate specific trends among the various classes of information. This dependence is shown in FIGS. 13 and 14.

Figure 13:
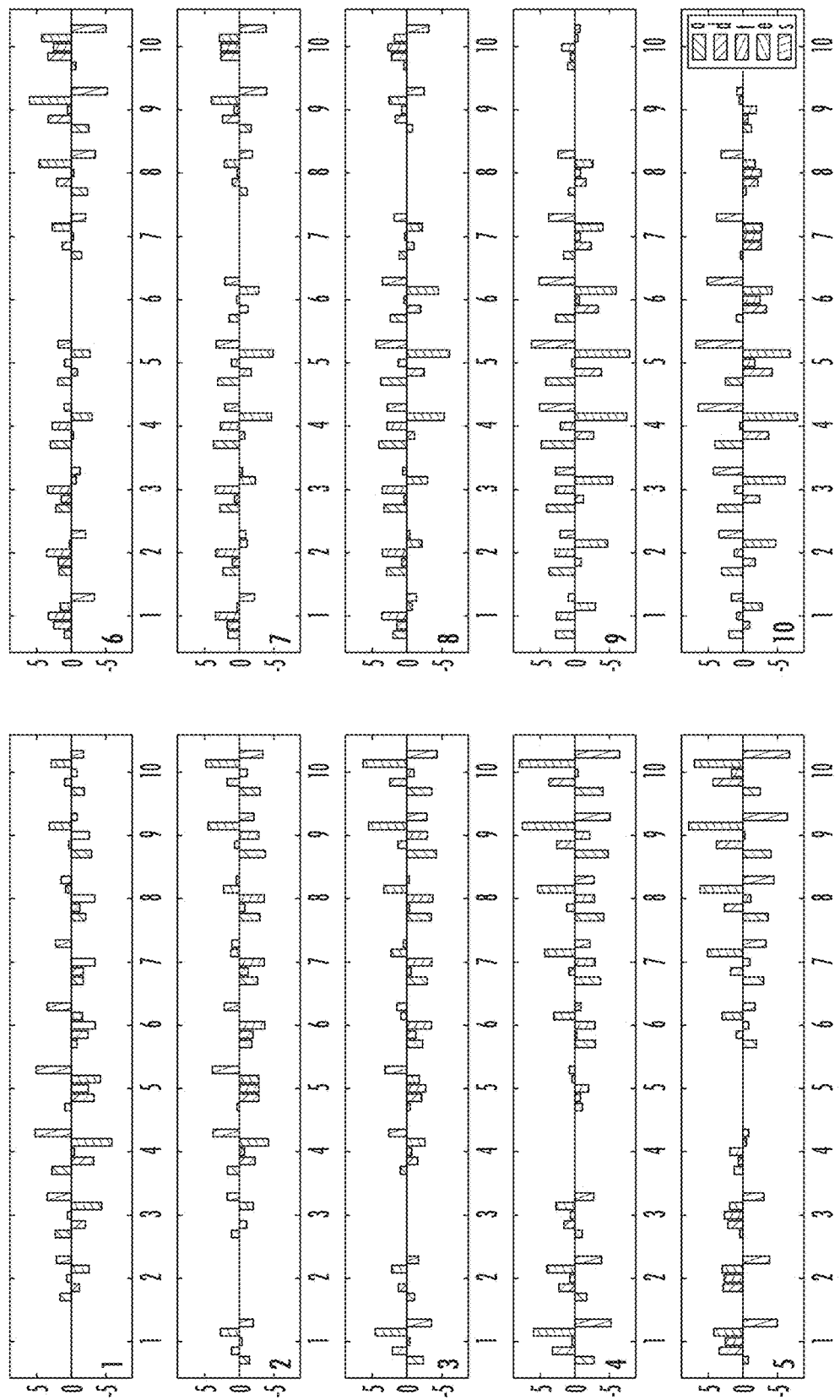
FIG. 13 is a series of plots of intrinsic transition-flux data [computed using Eq. (6)], for the affected breasts of the breast-cancer subject group, formatted as bar graphs to facilitate quantitative comparison, in accordance with the invention. A common vertical scale (dimensionless) is achieved by multiplying 'o', 'd', 't' and 'e' fluxes by 10$^8$, and 's' by 10$^2$. Each panel corresponds to one row (explicitly identified by a number in the lower left corner) from the set of five maps analogous to those in FIG. 10 (control group), all in accordance with the invention.

Data represented in FIG. 13 is a replot of ΔHb intrinsic fluxes, similar to those plotted in FIG. 10, but obtained from the affected breast of the breast-cancer group, with the intrinsic-flux amplitudes presented in the form of bar graphs. As in the 10×10 plots already considered, the column index encodes the state that the transitions proceed from and the row index indicated the state that is transitioned into. Inspection reveals that the amplitude for each component smoothly varies when we compare values that correspond to a clockwise or counter-clockwise progression among the states identified in FIG. 1. Also seen is that the maximum amplitude that a given component has is associated with preferred states, as would be expected from the orientation of the various axes to each other (see FIG. 1). For instance, we find that the largest amplitude for $\Delta HbO_2Sat$ occurs in transitions between States 5 and 10. A largely similar response, but broadened to include transitions involving States 4 and 9, is seen for $\Delta HbO_2Exc$, ΔdeoxyHb and ΔoxyHb. A notably different trend is seen for ΔtotalHb, where the highest-flux transitions are those between one of States 1-3 and one of States 6-8.

While these general trends are not overly surprising in view of the orientations of the component axes, the observation that there are subject-group differences in the mean amplitudes of each component (e.g., different orientations of elliptical patterns seen in FIGS. 4 and 7) facilitates appreciation of these trends. To highlight this effect, in FIG. 14 we replot the amplitudes shown in FIG. 13, pairing the flux values of the two independent quantities, ΔdeoxyHb and ΔoxyHb. Additionally, we have color-coded the pairing to indicate which state each transition type proceeds from. Note that data presented in FIG. 14 differs from that shown in FIGS. 7, 8, in that the former are derived from only the combinations of voxel and time frame that participate in transitions, while the latter consider the entire image volume and all the measurement time frames.

Figure 14A:
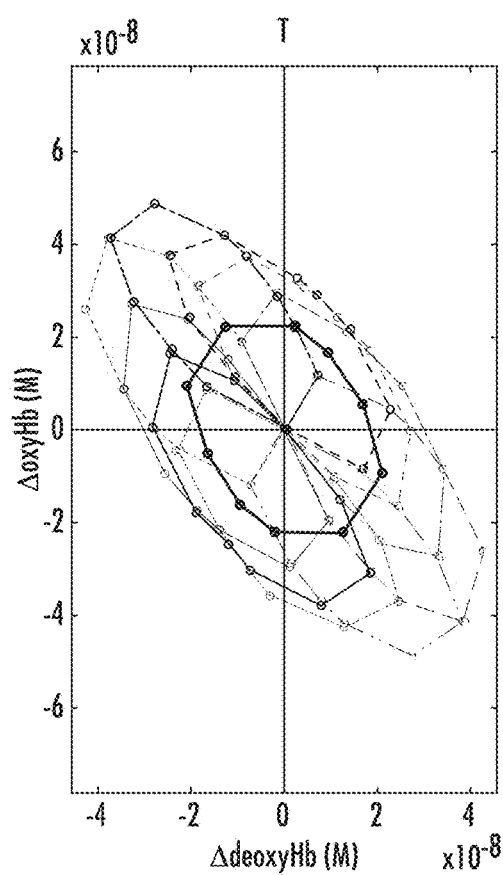
FIGS. 14(a) and 14(b) are a pair of plots of ΔoxyHb transition flux vs. ΔdeoxyHb transition flux, for the (FIG. 14(a)) tumor-bearing and (FIG. 14(b)) unaffected breast of the breast-cancer subjects, in accordance with the invention. Each closed curve contains data for transitions into one of the ten Hb- states, in accordance with the invention. For the solid curves and symbols: red=transitions into State 1, blue=State 2, green=State 3, cyan=State 4, magenta=State 5. For the dashed curves with open symbols: red=transitions into State 6, blue=State 7, green=State 8, cyan=State 9, magenta=State 10. Gray curves: Average difference between post- and pre-transition ΔoxyHb vs. average difference between post- and pre-transition ΔdeoxyHb, for each of the ten states, all in accordance with the invention.
Figure 14B:
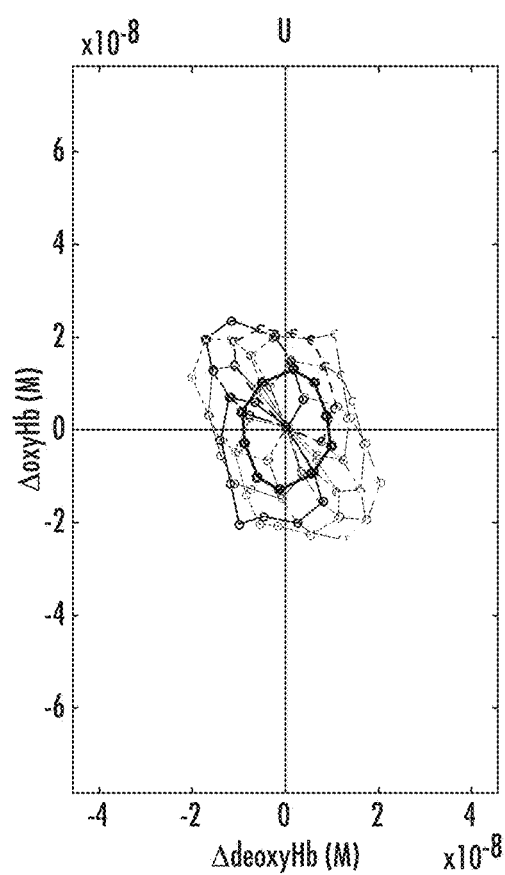

Shown in FIGS. 14(a) and 14(b) are the group-level responses for tumor-bearing breasts and for the unaffected contralateral breasts, respectively. Seen are two classes of information; paired transition-flux amplitudes (colored solid and dashed lines), and paired mean-amplitude values for a given state (gray lines); both information classes are extracted from time-series image data for only the combinations of voxel and time-steps that participated in transitions (Note that the similarity between gray curves and the colored curves plotted in FIG. 7. However, consistent with the smaller-than-unity regression slopes reported in Table 2, the former do not extend as far along the coordinate axes as the latter do). Also evident is that the former constitute a set that have a common intersection at the origin. This intersection follows from the definition that voxels that have not undergone a transition between the previous time step and the current one (so that the "from" state is the same as the "to" state) have a transition flux of zero. Each line color corresponds to transitions into a common state. Thus, the red color identifies transitions into State 1 from all other states. Successive transitions into the common state are identified by proceeding from the origin in the counter-clockwise direction. It follows that the point on the red curve that is connected to the origin and located in the second Cartesian quadrant corresponds to the transitions from State 2 into State 1. Similarly, the point connected to the latter and proceeding in the counter-clockwise direction corresponds to transitions from State 3 into State 1. A similar process assigns points on the solid blue, green, cyan and magenta curves to transitions into States 2, 3, 4 and 5, respectively. Thus, the blue point one counter-clockwise position removed from the origin corresponds to transitions from State 3 into State 2. Data for transitions into States 6-10 are identified by the colored dotted lines. Note that, because the transition fluxes among a given pair of states is substantially antisymmetric (i.e., if Φ is the flux for the A→B transition, then that for the B→A transition will be close to -Φ), data values plotted for transitions into States 6-10 amounts to a 180° rotation about the origin of those plotted for States 1-5.

Comparison of FIGS. 14(a) and 14(b) reveals two prominent observations. Most evident is the greater dispersion of values about the origin, with a distinct ellipsoidal elongation along the $\Delta HbO_2Exc$ axis (Cartesian quadrants II and IV) in the result obtained from affected breasts [FIG. 14(a)]. The corresponding trends for unaffected breasts [FIG. 14(b)] have reduced dispersion about the origin and a relative clockwise rotation of points. These differences are similar to the orientations seen in the FIG. 4 scatterplots and reflect a bias in the ability of the affected breast to maintain steady-state supply-demand balance. Different, however, is the amplitude for each set of transitions into a common state compared to the mean amplitudes within the state. Taking a larger view, the plots provide a significantly more granular appreciation of qualitative and quantitative differences among the different subject-breasts pairings than could be appreciated without considering the transition-flux amplitudes. Overall, these and the amplitudes of the other identified coefficients reveal a dense matrix of values that become available only from examination of the co-varying elements of the hemoglobin signal using the described finite-state transition representation.

d. Amplitude Maps of Weighted Transition Mass Values

As noted in Methods, we recognize that composites of coefficient amplitude values [Eqs. 7-9] have the potential to reveal other features not readily revealed from examination of the intrinsic coefficients values. One feature of interest is the quantity we refer to as the 'transition mass', which is the product of the intrinsic flux amplitude for a given component and the transition probability. This quantity holds significance, as it best describes the overall quantity of Hb component that participates in transitions of a particular type. Because the transition probability (FIG. 6) varies significantly over the set of transition types and is weakly correlated with the patterns seen in the component flux maps (FIG. 10), it can be expected that the corresponding weighted-flux coefficient map will also differ significantly from its unweighted counterpart. Shown in FIG. 15 are selected plots of this coefficient space for ΔtotalHb and $\Delta HbO_2Sat$.

Figure 15A:
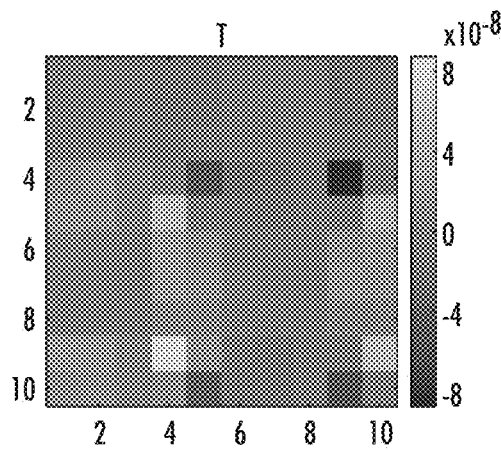
FIGS. 15(a)-15(d) are graphical representations of some of the methods in accordance with the invention.
Figure 15B:
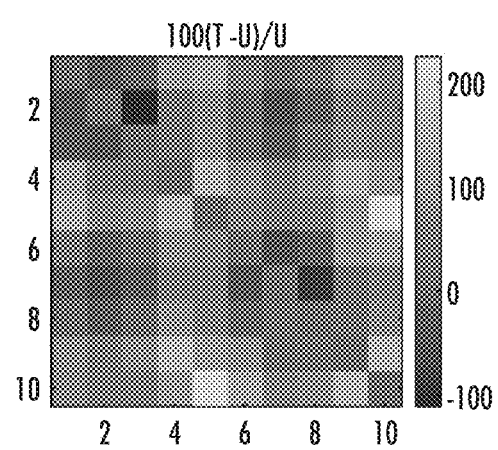
Figure 15C:
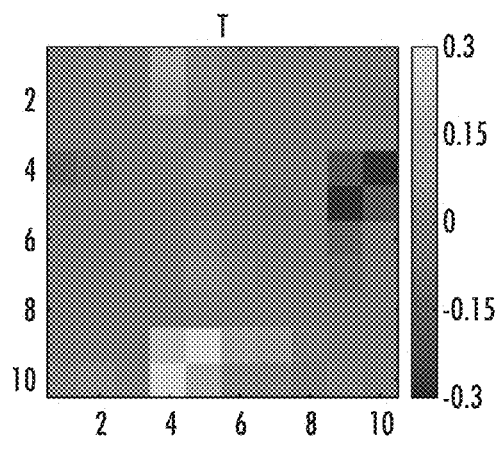
Figure 15D:
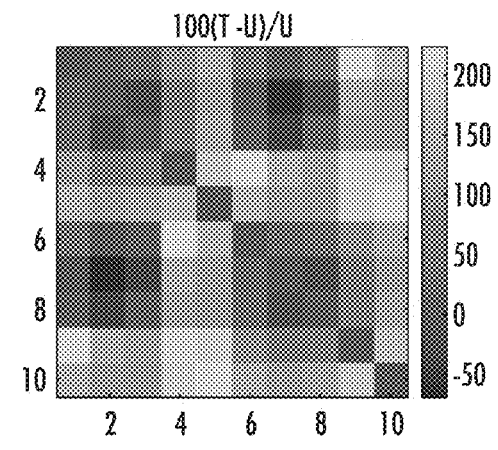

Plotted are 10×10 maps of the transition-mass amplitude for tumor-bearing breasts, and the relative difference in amplitude when this is compared to the corresponding data for the contralateral unaffected breast. Findings for ΔtotalHb and $\Delta HbO_2Sat$ are shown in FIG. 15(a),(b) and 15(c),(d) respectively. Inspection of these weighted flux maps reveals a transition dependence that differs substantially from those for the intrinsic-flux amplitudes (FIGS. 10 and 13). Here we find that only a selected few transition types appear to dominate the overall pattern. It is also apparent that the distribution of these among the various transition types differs between the two Hb components. Favored for ΔtotalHb [FIG. 15(a)] are transitions mainly among States 4, 5, and 9 and 10. In contrast, the pattern seen for Δnb 0₂Sat [FIG. 15(c)] strongly favors transitions between either 4 or 5 with either 9 or 10, with reduced amplitudes for adjacent transition types. Patterns grossly similar to the latter are found for the other Hb components (not shown). Also shown in FIG. 15 is the pattern of relative changes in transition mass when the affected and unaffected breast patterns are compared [15(b),(d)]. Inspection reveals that the dependence on transition type obtained is qualitatively different from similar comparisons presented above (cf., FIG. 12). Common to both Hb components are regions where the relative difference value is depressed in the affected individuals and others where it is notably increased.

As measures of m constitute a composite quantity that includes P, it is not overly surprising that the finding that trends in bilateral breast comparisons of affected subjects are grossly similar to that seen for seen for P. Nevertheless, the details of these trends differ among the different coefficient classes (cf, FIG. 6c), indicating that the influence of disease varies across the various coefficient spaces.

Data in mass-related nRMSD and correlation rows of Table 2 indicate that, similar to the previously considered intrinsic fluxes, the transition-mass correlations for all Hb components are notably lower for the T-U pairing than for any of the others, and the nRMSD is notably larger.

3. ROC Findings

Figure 16A:
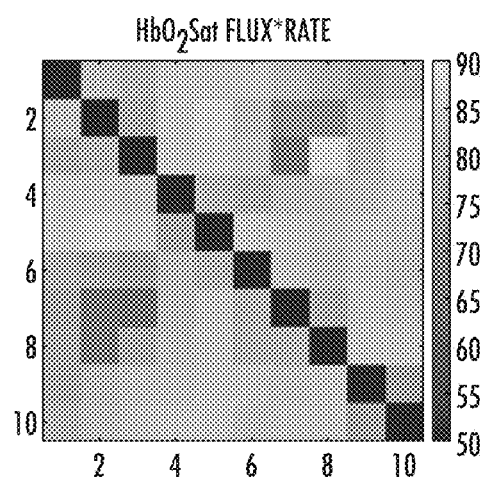
FIGS. 16(a) and 16(b) are plots of area-under-curve values from ROC analyses (units are percent) comparing the inter-breast differences for subjects in the non-cancer and breast-cancer groups, in accordance with the invention. The transition-based coefficients used as input to the ROC analysis computations are the product of intrinsic flux and either transition rate constant as shown in FIG. 16(a) or transition probability as shown in FIG. 16(b), all in accordance with the invention.
Figure 16B:
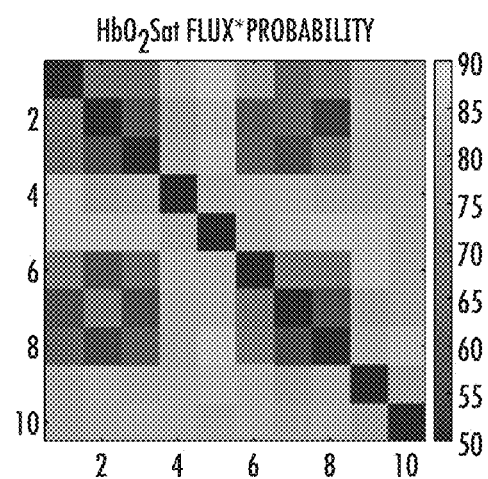

Finally, shown in FIG. 16 are results from ROC analyses (univariate AUC measures) applied to two classes of weighted coefficient values for ΔHbO₂Sat: flux amplitude weighted by the rate constant [Eq. (8), FIG. 16(a)], and the transition mass [Eq. (7), FIG. 16(b)]. Inspection reveals that for the former most of transition coefficients exhibit AUC values in the 80-90% range. Different from this is a distinct checkerboard pattern seen in the transition-mass case. We consider this finding as additional evidence that the various elements of the coefficient space examined carry qualitatively different information.

Description of Alternative Embodiments

1. Extensions and Generalizations of Specific Preferred-Embodiment Features

The invention is not dependent on the specific values assigned to any of the parameters, and can be modified in any of the following ways.

(The three following alternative embodiments are in reference to "Relationships among co-varying elements of the Hb signal")

A1. The number of Hb-states defined can be either less than or greater than 10, and a state corresponding to any specifiable angular sector of the space depicted in FIG. 1 can be defined (e.g., State A is defined as the set of all points lying between rays inclined at angles of B degrees and C degrees with respect to the horizontal axis).

A2. The definition of a Hb-state can take distances of points from the coordinate-system origin into account, in one or more coordinate directions, in addition to the angular information (e.g., State A is defined as the set of all points lying between rays inclined at angles of B degrees and C degrees with respect to the horizontal axis, with values for ΔdeoxyHb of at least D mol·L⁻¹ and at most E mol·L⁻¹, and with values for ΔoxyHb of at least F mol·L⁻¹ and at most G mol·L⁻¹).

A3. A reference point other than the resting-state temporal mean value can be used for defining temporal fluctuation values (e.g., ΔtotalHb), i.e., for defining the origin of the coordinate system. Different reference points may be chosen for different components of the Hb signal.

(The three following alternative embodiments are in reference to "Quantification of inter-state Hb-transition coefficients")

B 1. Transition counts may be based on the Hb-state of the $v^{th}$ voxel in the $t^{th}$ time frame and at a fixed number n of time frames later. In this case the time interval nΔt may be taken as an additional control parameter, and a count-vs.-n function generated [R. L. Barbour and H. L. Graber, "Characterization of hemoglobin dynamics as a co-varying system in the resting state: Evidence of functional bias of preferred states and sensitivity to disease," Poster #220 at 2016 Biennial Meeting of The Society for Functional Near Infrared Spectroscopy (Paris, October 13-16, 2016)].

B2. The transition counts for each post-transition Hb-state can take into account not only the immediately preceding state but also the one before that. Generalizing, for any positive number k, k=1, 2, 3, . . . , the k states prior to the immediate predecessor may be taken into account. As an example, instead of a single count of all transitions from State 1 into State 2, an alternative embodiment could perform nine separate counts, corresponding to the nine states that may have preceded State 1:2→1→2,3→1→2,4→1→2, etc.

B3. Transition counts need not be evaluated at the level of individual voxels, but may consider 2 or more voxels defining a region on either an anatomical (e.g., physically contiguous) or functional (e.g., all have initial values of ΔtotalHb and ΔHbO₂Exc within specified ranges) basis. As multiple voxels need not all be in the same Hb-state, rules would be specified for determining which pre- and post-transition states to count (e.g., the median state-value for all voxels in the defined cluster) and for when to count them (e.g., after one or more fixed values of n, or after a majority of voxels in the cluster have undergone a single direct transition).

(The seven following alternative embodiments are in reference to "Computation of State Transition Probability")

C1. As mentioned in A1, the number of defined Hb-states, $N_S$, may be different from 10. In general, the sizes of the first and second dimensions of the accumulator array will be $N_S$.

C2. As mentioned in B 1, a fixed time-interval rule for counting transitions may be adopted. If this is done, then the f=i elements of the accumulator array will not be superfluous. A corollary is that the corresponding definition of $P_{fi}$ would not contain a factor of $1-\delta_{fi}$ in denominator.

C3. As mentioned in B 1, a fixed time-interval rule for counting transitions may be adopted. If this is done, then it is appropriate to compute transition probabilities for individual values of the time lag n, rather than to sum over them. Thus, the transition-probability formula becomes (taking into account the modifications described in C2 and C3)

$$P_{fi}(n) = 100 A_{fi}(n) \bigg/ \sum_{f=1}^{10} \sum_{i=1}^{10} A_{fi}(n).$$

C4. The rule for incrementing the values stored in elements of the accumulator array will be determined by the manner in which transitions are defined. If a fixed time-interval method is adopted, then the value in the [s(v,t+nΔt), $s(v,t),n]^{th}$ element of the accumulator array is increased by 1 whether or not $s(v,t+n\Delta t) \neq s(v,t)$ (and this would result in positive counts accumulating in the f=i elements). In addition, when the n-frame time lag is considered, all but the final n time frames serve as pre-transition frames and all but the initial n time frames serve as post-transition frames.

C5. In the place of constant increments, the increment added to the current value of an accumulator-array element can be a function of the current value. For example, incrementing by an amount directly proportional to the current value would be the temporal analogue of the procedure that produces "scale-free nets" [A.-L. Barabási and R. Albert, "Emergence of scaling in random networks," *Science* 286, 509-512 (1999)] when it is used to assign links between new network nodes and currently existing ones. (In contrast, assigning links with a probability that is independent of the current link number, which is the analogue of the preferred-embodiment procedure, generates "exponential nets" [R. Albert, H. Jeong, and A.-L. Barabási, "Error and attack tolerance of complex networks," *Nature* 406, 378-382 (2000)].) Use of non-constant increments may be contraindicated under all-resting-state conditions, if the start time for data collection is arbitrary. However, it could prove informative in, for example, the analysis of evolution to the steady state following an experimental perturbation.

C6. Multiple accumulator arrays may be employed, to enable separate counts of transitions occurring in different segments of the measurement time period instead of a single integration over all time. This ability could be important for studies not performed under resting-state conditions. Even in the case of resting-state studies, it would, for example, allow for the evaluation of the hypothesis that the tissue under study was not in a physiological steady state during the measurement time course.

C7. The number of dimensions of the accumulator array may be increased beyond 3, in order to allow for simultaneous consideration of more than one scheme for defining the accumulation increments. Another example where inclusion of additional array dimensions would be appropriate would be the case, described in B2, where transition counts take account of more than one predecessor Hb-state. Adoption of that approach would allow for computation of transition joint-probabilities (e.g., the probability that a voxel transitions first from State 2 to State 3, and then to State 5).

(The two following alternative embodiments are in reference to "Computation of State Transition Rate")

D1. While the demonstrations of concept explicitly consider only the mean time lag, the entire spectrum of statistical moments (standard deviation, skewness, kurtosis, etc.) can be defined and evaluated for differences among subject populations or, within a single population or single individual, among different tissue locations or among different segments of the measurement time period.

D2. The presented mean-time and rate formulas are specific for the case where direct transitions are counted, independently of the residence time in the "from" Hb-state. If a fixed time-interval rule for counting transitions is used, these parameters would be evaluated using methods known in the art for evaluating the mean time spent in transient states of a finite Markov chain [J. Komáthy and Y. Peres, "Lecture notes for Markov chains: Mixing times, hitting times, and cover times." Available online at http://www.win.tue.nl/~jkomjath/SPBlecturenotes.pdf] or other types of autoregressive model [K. Sheppard, "Analysis of a single time series." Available online at https://www.kevinsheppard.com/images/c/cf/Chapter4.pdf].

(The three following alternative embodiments are in reference to "Quantification transition-linked hemoglobin-concentration and-saturation changes")

E1. The rules for accumulating changes in Hb-signal component levels are tied to the rule adopted for counting transitions, in the sense that the latter determines which time frames are used for determining the increments of concentration (or percent change in saturation). However, the mathematical form of the equation is the same in all cases.

E2. If a transition-counting method is adopted that is based on spatial regions containing more than a single voxel (for example, the approach outlined in B3), then a corresponding modification would be made to the method used to compute the concentration and percent change increments. As an example, suppose a counting method mentioned in B3 is implemented: a transition is counted when a majority of voxels in the region have undergone a single direct transition, and the regional median Hb-state-values are taken as the "from" and "to" states. Then the pre-transition and post-transition concentrations (percent saturations) would be averaged over the same subsets of voxels that determined the identities of the "from" and "to" states. Other potentially useful information could be obtained by simultaneously accumulating [in a second set of arrays maintained in parallel with those defined in Eqs. (4),(5)] the complementary changes averaged over the subsets of voxels that were in states different from those determined by the regional medians.

E3. Results of the $A_D$, $A_E$, $A_O$, $A_S$ and $A_T$ (but not $A_{TC}$) calculations could be affected by changing the specific time frames in the pre- and post-transition intervals that are used for determining the concentration (percent saturation) increments. These effects can be quantified by calculating changes in signal levels for multiple specific pairs of pre- and post-transition time frames, or by calculating the means and standard deviations of the signal-level changes across all pairings of pre- and post-transition time frames. Implementation of either alternative would entail definition of additional accumulator arrays or of additional dimensions in the original set, with the statistical moments option having the advantage that the exact number of additional array elements required is knowable a priori.

(The following alternative embodiment is in reference to "Transition 'flux' computation")

F1. Summation over all values of n is specifically appropriate for the case where direct transitions are counted, independently of the residence time in the "from" Hb-state. For other transition-counting schemes, for example a fixed time-interval rule, it may be preferable to instead compute the full range of $\phi_X(f,i,n)$ values for the different time lags. Thus $\phi_X(f,i,n) = A_X(f,i,n)/A_{TC}(f,i,n)$. If desired, averages across ranges of n can be computed subsequently.

(The following alternative embodiment is in reference to "Computation of weighted transition fluxes")

G1. The same modifications are appropriate for Eqs. (7)-(9) as were already described in reference to Eq. (1) and Eq. (6). Thus the formulas for the time lag-dependent transition mass, rate-weighted flux and rate-weighted mass are $$m_X(f, i, n) = P_{fi}\phi_X(f, i, n) = 100 A_X(f, i, n) \bigg/ \sum_{f=1}^{10} \sum_{i=1}^{10} A_{TC}(f, i, n),$$

$$k_{fi}\phi_X(f,i,n) = A_X(f,i,n)/\tau_{fi}, \text{ and}$$

$$k_{fi}m_X(f,i,n) = 100A_X(f,i,n) \Big/ \left[\tau_{fi}\sum_{f=1}^{10}\sum_{i=1}^{10}A_{TC}(f,i,n)\right],$$

respectively. As indicated in D2, the method appropriate for computing the mean value for the time lag depends on the transition-counting rule adopted.

2. Additional Alternative-Embodiment Considerations a. Applicability of Formal Language Theory We believe that access to a dense feature space of substantially independent coefficients may support development of new approaches to computational modeling or new analysis strategies. This brings to mind a more basic understanding of factors contributing to information transduction. For instance, discrete-valued information such as sequences of Hb-states can be formally regarded as arbitrary-length "words" in a language having a 10-"letter" alphabet. The same concept applies equally well to sequences of transitions between the current state and its predecessor (for a 90-letter language), the current state and last two predecessors (810 letters), etc. The structures and constraints that may be concealed in these sequences are unknown a priori, and it is prudent to adopt analysis strategies that can handle arbitrary degrees and types of complexity. Work in other fields has shown that formal language theory (FLT) is well-suited for the type of situations that we are faced with [M. Gheorghe and V. Mitrana, "A formal language-based approach in biology," *Comparative and Functional Genomics* 5, 91-94 (2004)]. As an example of a goal that is conceptually straightforward, one might seek to use FLT to characterize the level in the Chomsky hierarchy that corresponds to a state- or transition-derived language, or to determine a set of grammatical rules from which the sequences can be derived [W. T. Fitch and A. D. Friederici, "Artificial grammar learning meets formal language theory: An overview," *Phil. Trans. R. Soc. B* 367, 1933-1955 (2012)]. Such information could then be used for evaluating a research goal such as whether the hierarchy level or the number or specific content of grammatical rules differs among different subject groups. Examples of criteria that may be used for differentiating these groups include: the presence or absence of pathology, different levels of distraction (brain studies), or fatigue or stress in cases where the aim is to appreciate factors affecting overall performance in high stress environments.

However, the type of undertaking suggested here is more challenging than the sorts of biological questions that typically are addressed using FLT-based methods [W. T. Fitch and A. D. Friederici, *Phil. Trans. R. Soc. B*]. The reason is that at least two considerations render the solution non-unique: first, when the information one has about a language consists of a finite number of letter sequences, then grammatical structures able to derive them all can be found at any hierarchical level, provided that no limit is placed on the number of rules [W. T. Fitch and A. D. Friederici, *Phil. Trans. R. Soc. B*; G. Jäger and J. Rogers, "Formal language theory: Refining the Chomsky hierarchy," *Phil. Trans. R. Soc. B* 367, 1956-1970 (2012)]; second, even if the hierarchical level is specified in advance, typically it is possible to determine multiple sets of grammatical rules that can derive all of the available sequences [G. Jäger and J. Rogers, *Phil. Trans. R. Soc. B*]. Accordingly, a strategy that incorporates multiple criteria is required to decide which, among many combinations of hierarchy level and grammatical-rule sets, is optimal. At minimum, the idea would be to simultaneously minimize the required hierarchical level and the required number of grammatical rules. (This approach is suggested in analogy to what is done in dynamic causal modeling computations to select the "best" model of effective connectivity from among many hypotheses: there, the algorithm strikes a balance between high goodness-of-fit to experimental data and low model complexity [K. E. Stephan, W. D. Penny, J. Daunizeau, R. J. Moran, and K. J. Friston, "Bayesian model selection for group studies," *NeuroImage* 46, 1004-1017 (2009)].) We also would anticipate making extensive use of cross-validation techniques [S. Arlot and A. Celisse, "A survey of cross-validation procedures for model selection," *Statistical Surveys* 4, 40-79 (2010)], to test for overfitting and to evaluate the sensitivity of different combinations of hierarchical level and grammatical rules to the order of data presentation.

b. Electrical Network Analogies

While the noted understandings from FLT constitute a particular alternative approach to increasing the type and quantity of information that could be extracted from fNIRS time-series data, methods for expressing features in terms of other quantities that have biological relevance but are not directly observable are also available. Thus we acknowledge the potential to extend the network representation considered here into one where the goal is to derive coefficients from a hidden network of coefficients that reflect features corresponding to details of feedback mechanisms. In particular, we consider the framework of a DC electrical network [K. S. Suresh Kumar, *Electrical Circuits and Networks*. Pearson Education Canada (2009). ISBN 978-8131713907], in recognition of the analogies that can be drawn between $P_{fi}$ (or $P_{fi}\phi_X(f,i)=m_{fi}$) and $k_{fi}$ to the electrical current and conductance (i.e., 1/resistance) represented in Ohm's Law. Connection to the physiological processes underlying observed patterns of state transition coefficients comes from an understanding that real-world electric-circuit networks are typically based on a distribution of power sources required to drive various specialized functionalities. As our State-flux representation considers behaviors that originate on a macroscopic scale within inhomogeneous underlying tissue architecture, it seems likely that the factors that modulate the Hb signal will also influence features of the state network in a distributed manner. Consequently, our attention in formulating a network representation has been to devise a scheme that allows for derivation of coefficients that correspond to such distributions.

The definitions of $k_{fi}$, $P_{fi}$ and $\phi_X(f,i)$ suggest a correspondence between $k_{fi}$ and electrical conductance, and likewise between either $P_{fi}$ or $P_{fi}\phi_X(f,i)$ and current. (The $P_{fi}$ values are "transition currents" if transitions are analogized to a type of particle, while $P_{fi}\phi_X(f,i)$ values are concentration-change currents or saturation-change currents.) The different co-variational states can be likened to nodes in an electrical network, and the quantity $1/k_{fi}$ to value of a resistor that conducts current from the $i^{th}$ node to the $j^{th}$ (more strictly, a resistor in series with an ideal diode, to allow for $k_{fi} \neq k_1$). These correspondences bring to mind at least two additional analogies to properties of electrical circuits.

1) A new quantity corresponding to voltage can be defined, by applying an analogue of Ohm's law to the transition-probability and rate values:

$$V_{TC}(f,i) = \frac{k_{fi}}{P_{fi}}, \quad V_X(f,i) = \frac{k_{fi}\phi_X(f,i)}{P_{fi}}, \tag{14}$$

where X is any of the Hb-signal components D, E, 0, S or T in Eq. (5).

2) In the typical framing of electrical-network analysis problems [T. R. Kuphaldt, "DC Network Analysis," Chapter 10 in *Lessons in Electrical Circuits*, Volume I—DC, $5^{th}$ Ed. Open Book Project (2006). Available online at https://www.allaboutcircuits.com/textbook/direct-current/], the resistances and applied electromotive forces (EMFs) are known quantities and the voltages and currents are the unknowns that are solved for. A different, inverse, version of the problem is suggested here, in that the currents and resistances are known quantities, and what must be found is an EMF or combination of EMFs that would produce the known currents, given the known structural (connectivity and resistances) and dynamic (currents) properties of the network. Assuming these quantities can be identified with a degree of confidence, then the considered approach would seem capable of amplifying our understanding of the actions of feedback mechanisms whose influences can be directly observed but whose details remain hidden.

c. Applicability of Hb-State Concepts to Enhancing Capabilities of Other fNIRS Analysis Strategies The potential to express properties of the defined states in terms of their sensitivities to more primitive behaviors is one that we have previously recognized. Here we refer to a methodology recently described by our group, which demonstrated that cross-domain moments of spatiotemporal behaviors (i.e., mean, variance) can be distinguished in terms of their sensitivity to these primitive behaviors [H. L. Graber et al., *Medical Physics*]. While here our emphasis is on exploration of data features that undergo specific Hb-state transitions, we also recognize that the cloud of points corresponding to each state (e.g., see FIG. 4), can be represented as a time series. In fact, because each state is a composite of the five elements of the Hb signal, five time series can be defined for each state. For each of these it can be shown that there are fourteen nontrivial cross-domain (space-time) moments that can be defined (i.e., the eight that are considered in Ref. Graber et al. plus an additional six, five of which would be trivial (because always exactly zero) should the Hb signal not be separated into Hb-states). Our interest in these quantities is motivated by the expectation that as the underlying drivers of tissue-vascular coupling vary (e.g., as they are influenced by actions of disease), they can imprint different spatiotemporal behaviors that are sensitive to the indicated primitives. Thus we acknowledge that in addition to the above-described transition-dependent network properties, representations of bulk features of the network may add to the differential information that is accessible.

d. Extension to Other Conceptual Domains in Graph Theory

As a separate avenue for potential future developments, it has been noted above that the range of network indices herein described spans a subset of the broader field of graph theory (which is, in turn, a subset of the even broader field of discrete mathematics). In particular, strong analogies can be drawn between the network features emphasized in the preferred embodiment (e.g., transition probabilities, rates, fluxes, masses) and graph-theory methods developed for analysis of substrate concentrations and fluxes (i.e., rates of substrate production and consumption) as determined by the actions of enzymes linked together in functional networks (i.e., for metabolomics) [C. H. Schilling and B. O. Palsson, *Proc. Natl. Acad. Sci.*]. Consequently, these parallels bring the expectation that algorithms used to analyze the functioning of networks into elementary flux modes [S. Schuster, T. Dandekar, and D. A. Fell, "Detection of elementary flux modes in biochemical networks: A promising tool for pathway analysis and metabolic engineering," *Trends in Biotechnology* 17, 53-60 (1999] can also be applied to the network of Hb-flux states, to determine whether pathway preferences exist and, if so, if there are informative differences between the dominant pathways for different subject populations, or among individuals within a population.

Further, the preceding can be extended by recognizing that the mathematically defined network of states that is subjected to the analysis may include other nodes in addition to the Hb-flux states. For example, a goal of the analysis may be to evaluate one or more hypotheses regarding the role of known biochemical or physiological processes in determining the observed transition probabilities, rates, etc. Typically these processes are the entities of ultimate scientific interest, but they are not directly observable, at least not under the same experimental or clinical conditions as the hemodynamic signal. Thus the Hb-flux states constitute the "visible units" of the enlarged network, while states of the physiological processes (e.g., levels of specific metabolites, presence/absence of induced isoenzymes, levels of regulatory species) are the "hidden units" [L. R. Rabiner, "A tutorial on hidden Markov models and selected applications in speech recognition," *Proceedings of the IEEE* 77, 257-286 (1989)]. Connecting the network nodes would be two types of "edges": those that, on the basis of either observation or fundamental biological understandings, are known to exist between pairs of visible or pairs of hidden nodes; and those that are hypothesized to exist between a hidden node and a visible one. One goal of the analysis considered here could be to determine, for each hypothetical pattern of edges connecting the node classes, values of edge weights [S. Umeyama, "An eigendecomposition approach to weighted graph matching problems," *IEEE Transactions on Pattern Analysis and Machine Intelligence* 10, 695-703 (1988)] that would allow the hidden fluxes to drive the observed ones while maintaining hidden fluxes that are plausible physically (i.e., all irreversible reactions proceed in the correct direction) and biologically (i.e., all flux magnitudes fall between established lower and upper limits) [C. H. Schilling, D. Letscher, and B. O. Palsson, "Theory for the systemic definition of metabolic pathways and their use in interpreting metabolic function from a pathway-oriented perspective," *J. Theoretical Biology* 203, 229-248 (2000)]. A related goal could be to select among different hypotheses, based on the sensitivities of network fluxes to perturbations of the computed edge weights. The latter application is conceptually similar to established strategies used to analyze fMRI and fNIRS data for the purpose of selecting among models of effective connectivity between brain regions [K. E. Stephan et al., *NeuroImage* 46].

Also understood is that other complementary set of indices for characterizing networks—e.g., average path length, diameter, average clustering coefficient, centralization, various centrality measures (degree, closeness, betweenness, eigenvector, and subgraph centrality), matching index [G. A. Pavlopoulos, M. Secrier, C. N. Moschopoulos, T. G. Soldatos, S. Kossida, J. Aerts, R. Schneider, and P. G. Bagos, "Using graph theory to analyze biological networks," *BioData Mining* 4 (2011)]—is available. The preferred embodiment does not explicitly consider these, for the reason that the functional network if Hb-flux states constitutes a complete graph [G. A. Pavlopoulos et al., *BioData Mining*], which is to say that every element in its adjacency matrix [G. A. Pavlopoulos et al., *BioData Mining*] is equal to 1. As such, none of the mentioned network indices would have non-trivial values. However, meaningful network-index values can be obtained by substituting a weighted adjacency matrix [S. Umeyama, *IEEE Transactions on Pattern Analysis and Machine Intelligence*] for the more familiar type in which each element simply indicates the presence (1) or absence (0) of a direct connection. The preferred embodiment generates a set of quantities that can be taken as adjacency weight values: transition probability, rate, flux, mass, rate-weighted flux, and rate-weighted mass. Index values thus generated could be interpreted as features of the underlying networks, and evaluated to test for the presence of informative differences between subject populations, or among individuals within a population.

The preceding discussion has used the concept of networks in a qualitatively different manner that which is considered in the field of machine learning using artificial neural networks [A. K. Jain, J. Mao, and K. M. Mohiuddin, "Artificial neural networks: A tutorial," *IEEE Computer Magazine*, March 1996, 31-44; L. J. Lancashire, C. Lemetre, and G. R. Bal, "An introduction to artificial neural networks in bioinformatics—application to complex microarray and mass spectrometry datasets in cancer studies," *Briefings in Bioinformatics* 10, 315-329 (2009]. We are aware that some of the data analysis efforts suggested by the above enlarged networks can become computationally challenging. It is of course plausible to use network-based (in the machine-learning sense) techniques to use network-based (in the machine-learning sense) techniques to search for plausible, or even optimal, solutions to problems such as the previously described analysis of connectivity between the visible and hidden parts of a composite functional network.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

What is claimed is:

1. A non-invasive method of detecting breast cancer in a patient via time series measures of the hemoglobin signal, acquired under conditions of a substantially resting state, from at least one breast by comparing the values of coefficients obtained from a functional finite-state transition network representation of said signal, comprising the steps of:
   non-invasively measuring at least two measured hemoglobin signal components of hemoglobin levels in at least one breast of the patient in a substantially resting state over time, the at least two measured hemoglobin signal components comprising oxygenated hemoglobin and deoxygenated hemoglobin;
   transforming the measured hemoglobin signal components to yield relative changes in the levels of oxygenated and deoxygenated forms of hemoglobin and to compute at least three derived hemoglobin signal components;
   specifying a multiaxis representation of the two measured hemoglobin signal components and the three derived hemoglobin signal components and determining the algebraic sign of each hemoglobin signal component based on their measured relative amplitudes;
   defining the composite of these algebraic sign assignments as a hemoglobin state, of which ten such composites are uniquely defined;
   determining when in time at least one hemoglobin signal component undergoes a change in its algebraic sign and identifying such occurrence as a State transition;
   computing coefficient values for at least one of i) State transition rates, ii) State transition probabilities from the tabulation of unique transition types, or iii) State-dependent component flux of a given State; and
   detecting any cancerous tissue in the measured breast from a signature of said State transitions of the measured breast which differs from a signature of State transitions of non-cancerous tissue.

2. A non-invasive method of detecting breast cancer in a patient according to claim 1, wherein said at least two measured hemoglobin signal components comprise oxyHb and deoxyHb, and wherein said at least three derived hemoglobin signal components comprise total Hb (totalHb=oxyHb+deoxy Hb), Hb oxygen saturation ($HbO_2Sat$=(oxyHb/totalHb)*100), and tissue-hemoglobin oxygen exchange ($HbO_2Exc$=deoxyHb−oxyHb).

3. A non-invasive method of detecting breast cancer in a patient according to claim 1, wherein said first measuring step further comprises the step of measuring the tissue optically.

4. A non-invasive method of detecting breast cancer in a patient according to claim 3, wherein said optical measuring step further comprises the steps of:
   illuminating the breast with light; and
   measuring at least one of diffusely transmitted or back-reflected light from the breast.

5. A non-invasive method of detecting breast cancer in a patient according to claim 1, wherein said first measuring step further comprises the step of measuring the tissue at least one of photoacoustically, holographically, via structured illumination, or via OCT.

6. A non-invasive method of detecting anomalous tissue in a patient via time series measures of the hemoglobin signal, acquired under conditions of a substantially resting state, by comparing the values of coefficients obtained from a functional finite-state transition network representation of said signal, comprising the steps of:
   non-invasively measuring at least two measured hemoglobin signal components of hemoglobin levels in at least one segment of tissue of the patient in a substantially resting state over time, the at least two measured hemoglobin signal components comprising oxygenated hemoglobin and deoxygenated hemoglobin;
   transforming the measured hemoglobin signal components to yield relative changes in the levels of oxygenated and deoxygenated forms of hemoglobin and to compute at least three derived hemoglobin signal components;
   specifying a multiaxis representation of the two measured hemoglobin signal components and the three derived hemoglobin signal components and determining the algebraic sign of each hemoglobin signal component based on their measured relative amplitudes;
   defining the composite of these algebraic sign assignments as a hemoglobin state, of which ten such composites are uniquely defined;
   determining when in time at least one hemoglobin signal component undergoes a change in its algebraic sign and identifying such occurrence as a State transition;
   computing coefficient values for at least one of i) State transition rates, ii) State transition probabilities from the tabulation of unique transition types, or iii) State-dependent component flux of a given State; and
   detecting any anomalous tissue in the measured segment of tissue from a signature of said State transitions of the measured segment of tissue which differs from a signature of State transitions of non-anomalous tissue.

7. A non-invasive method of detecting anomalous tissue in a patient according to claim 6, wherein said at least two measured hemoglobin signal components comprise oxyHb and deoxyHb, and wherein said at least three derived hemoglobin signal components comprise total Hb (totalHb=oxyHb+deoxy Hb), Hb oxygen saturation (HbO$_2$Sat=(oxyHb/totalHb)*100), and tissue-hemoglobin oxygen exchange (HbO$_2$Exc=deoxyHb−oxyHb).

8. A non-invasive method of detecting anomalous tissue in a patient according to claim 6, wherein said first measuring step further comprises the step of measuring the tissue optically.

9. A non-invasive method of detecting anomalous tissue in a patient according to claim 8, wherein said optical measuring step further comprises the steps of:
  illuminating the segment of tissue with light; and
  measuring at least one of diffusely transmitted or back-reflected light from the segment of tissue.

10. A non-invasive method of detecting anomalous tissue in a patient according to claim 6, wherein the anomalous tissue to be detected comprises at least one of cancerous tissue or injured tissue.

11. A non-invasive method of detecting anomalous tissue in a patient according to claim 6, wherein said first measuring step further comprises the step of measuring the tissue at least one of photoacoustically, holographically, via structured illumination, or via OCT.

12. A non-invasive method of detecting changes in tissue in a living subject in response to physical and/or chemical stimuli patient via time series measures of the hemoglobin signal, acquired under conditions of a substantially resting state, by comparing the values of coefficients obtained from a functional finite-state transition network representation of said signal, comprising the steps of:
  applying at least one physical or chemical stimulus to the living subject;
  non-invasively measuring at least two hemoglobin signal components of hemoglobin levels in at least one segment of tissue of the living subject in a substantially resting state over time, the at least two measured hemoglobin signal components comprising oxygenated hemoglobin and deoxygenated hemoglobin;
  transforming the measured hemoglobin signal components to yield relative changes in the levels of oxygenated and deoxygenated forms of hemoglobin and to compute at least three derived hemoglobin signal components;
  specifying a multiaxis representation of the two measured hemoglobin signal components and the three derived hemoglobin signal components and determining the algebraic sign of each hemoglobin signal component based on their measured relative amplitudes;
  defining the composite of these algebraic sign assignments as a hemoglobin state, of which ten such composites are uniquely defined;
  determining when in time at least one hemoglobin signal component undergoes a change in its algebraic sign and identifying such occurrence as a State transition;
  computing coefficient values for at least one of i) State transition rates, ii) State transition probabilities from the tabulation of unique transition types, or iii) State-dependent component flux of a given State; and
  detecting any changes in the measured segment of tissue from a signature of said State transitions of the measured segment of tissue after the at least one stimulus is applied with respect to a signature of State transitions of the measured segment of tissue before the at least one stimulus is applied.

13. A non-invasive method of detecting changes in tissue in a living subject in response to physical and/or chemical stimuli according to claim 12, wherein said at least two measured hemoglobin signal components comprise oxyHb and deoxyHb, and wherein said at least three derived hemoglobin signal components comprise total Hb (totalHb=oxyHb+deoxy Hb), Hb oxygen saturation (HbO$_2$Sat=(oxyHb/totalHb)*100), and tissue-hemoglobin oxygen exchange (HbO$_2$Exc=deoxyHb−oxyHb).

14. A non-invasive method of detecting changes in tissue in a living subject in response to physical and/or chemical stimuli according to claim 12, wherein said first measuring step further comprises the step of measuring the tissue optically.

15. A non-invasive method of detecting changes in tissue in a living subject in response to physical and/or chemical stimuli according to claim 14, wherein said optical measuring step further comprises the steps of:
  illuminating the segment of tissue with light; and
  measuring at least one of diffusely transmitted or back-reflected light from the segment of tissue.

16. A non-invasive method of detecting changes in tissue in a living subject in response to physical and/or chemical stimuli according to claim 12, wherein said first measuring step further comprises the step of measuring the tissue at least one of photoacoustically, holographically, via structured illumination, or via OCT.

* * * * *